(12) United States Patent
Yu

(10) Patent No.: US 9,023,338 B2
(45) Date of Patent: May 5, 2015

(54) CANCER STEM CELL ANTIGEN VACCINES AND METHODS

(75) Inventor: John S. Yu, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 363 days.

(21) Appl. No.: 13/365,666

(22) Filed: Feb. 3, 2012

(65) Prior Publication Data

US 2012/0189664 A1    Jul. 26, 2012

Related U.S. Application Data

(63) Continuation of application No. 11/862,135, filed on Sep. 26, 2007, now Pat. No. 8,129,184.

(60) Provisional application No. 60/826,955, filed on Sep. 26, 2006.

(51) Int. Cl.
    A61K 39/00     (2006.01)
    C12N 5/095     (2010.01)

(52) U.S. Cl.
    CPC ..... *A61K 39/0011* (2013.01); *A61K 2039/5154* (2013.01); *C12N 5/0695* (2013.01)

(58) Field of Classification Search
    None
    See application file for complete search history.

(56) References Cited

U.S. PATENT DOCUMENTS

| | | | |
|---|---|---|---|
| 4,690,915 A | 9/1987 | Rosenberg | |
| 4,844,893 A | 7/1989 | Honsik et al. | |
| 5,635,363 A | 6/1997 | Altman et al. | |
| 5,643,786 A | 7/1997 | Cohen et al. | |
| 5,788,963 A | 8/1998 | Murphy et al. | |
| 5,831,016 A | 11/1998 | Wang et al. | |
| 5,843,448 A | 12/1998 | Chen et al. | |
| 5,843,633 A | 12/1998 | Yin et al. | |
| 5,844,075 A | 12/1998 | Kawakami et al. | |
| 5,846,538 A | 12/1998 | Cheever et al. | |
| 5,849,589 A | 12/1998 | Tedder et al. | |
| 5,851,756 A | 12/1998 | Steinman et al. | |
| 5,869,445 A | 2/1999 | Cheever et al. | |
| 5,876,712 A | 3/1999 | Cheever et al. | |
| 5,925,729 A | 7/1999 | Boon et al. | |
| 5,994,126 A | 11/1999 | Steinman et al. | |
| 6,010,905 A | 1/2000 | Cohen et al. | |
| 6,015,567 A | 1/2000 | Hudziak et al. | |
| 6,037,135 A | 3/2000 | Kubo et al. | |
| 6,077,519 A | 6/2000 | Storkus et al. | |
| 6,248,329 B1 | 6/2001 | Chandrashekar et al. | |
| 6,300,090 B1 | 10/2001 | Steinman et al. | |
| 6,455,678 B1 | 9/2002 | Yin et al. | |
| 6,458,585 B1 | 10/2002 | Vachula et al. | |
| 6,479,286 B1 | 11/2002 | Nelson et al. | |
| 6,482,405 B1 | 11/2002 | Tahara et al. | |
| 6,514,942 B1 | 2/2003 | Ioannides et al. | |
| 6,537,560 B1 | 3/2003 | Kawakami et al. | |
| 6,566,395 B1 | 5/2003 | Moran | |
| 6,632,459 B2 | 10/2003 | Graus et al. | |
| 6,984,522 B2 | 1/2006 | Clarke et al. | |
| 7,115,360 B2 | 10/2006 | Clarke et al. | |
| 7,186,409 B2 | 3/2007 | Snyder et al. | |
| 7,204,982 B2 | 4/2007 | Liau | |
| 7,247,480 B2 | 7/2007 | Waldmann et al. | |
| 7,311,916 B2 | 12/2007 | Wild et al. | |
| 7,338,929 B2 | 3/2008 | Debinski et al. | |
| 7,368,531 B2 | 5/2008 | Rosen et al. | |
| 7,402,314 B2 | 7/2008 | Sherman et al. | |
| 7,504,490 B1 | 3/2009 | Weinstock et al. | |
| 7,842,466 B1 | 11/2010 | Kim et al. | |
| 8,097,256 B2 | 1/2012 | Yu et al. | |
| 8,129,184 B2 | 3/2012 | Yu | |
| 8,168,586 B1 | 5/2012 | Fang et al. | |
| 8,383,768 B2 | 2/2013 | Singh et al. | |
| 8,604,167 B2 | 12/2013 | Singh et al. | |
| 2002/0034819 A1 | 3/2002 | Smith et al. | |
| 2002/0045261 A1 | 4/2002 | Snyder et al. | |
| 2002/0076707 A1 | 6/2002 | Mack et al. | |
| 2002/0115213 A1 | 8/2002 | Snyder et al. | |
| 2002/0119121 A1 | 8/2002 | Vitiello et al. | |
| 2002/0182194 A1 | 12/2002 | Ju et al. | |
| 2002/0192211 A1 | 12/2002 | Hudziak et al. | |
| 2003/0064916 A1 | 4/2003 | Sherman | |
| 2003/0095955 A1 | 5/2003 | Noessner et al. | |
| 2003/0185823 A1 | 10/2003 | Lum et al. | |
| 2003/0190682 A1 | 10/2003 | Law et al. | |
| 2003/0202963 A1 | 10/2003 | Crystal et al. | |
| 2003/0204052 A1 | 10/2003 | Herrmann et al. | |
| 2003/0204071 A1 | 10/2003 | Moore et al. | |
| 2004/0057935 A1 | 3/2004 | Yu et al. | |
| 2004/0072246 A1 | 4/2004 | Martin et al. | |

(Continued)

FOREIGN PATENT DOCUMENTS

| | | |
|---|---|---|
| WO | WO 89/06692 | 7/1989 |
| WO | WO 92/20356 | 11/1992 |
| WO | WO 94/26293 | 11/1994 |
| WO | WO 95/21862 | 8/1995 |
| WO | WO 96/18409 | 6/1996 |
| WO | WO 00/24778 | 5/2000 |
| WO | WO 00/38730 | 7/2000 |
| WO | WO 00/66713 | 11/2000 |
| WO | WO 01/08636 | 2/2001 |

(Continued)

OTHER PUBLICATIONS

Yamanaka et al., 2003, British J. Can. vol. 89: 1172-79.*

(Continued)

*Primary Examiner* — Amy Juedes

(74) *Attorney, Agent, or Firm* — Fish & Richardson P.C.

(57) ABSTRACT

Method of stimulating an immune response (e.g., to treat cancer) include administering to a patient a composition including dendritic cells that present cancer stem cell antigens. Compositions including cancer stem cell antigens are also provided herein.

30 Claims, 17 Drawing Sheets

(56) References Cited

U.S. PATENT DOCUMENTS

| | | | |
|---|---|---|---|
| 2004/0121946 A9 | 6/2004 | Fikes et al. | |
| 2004/0197903 A1 | 10/2004 | Pestano | |
| 2004/0203143 A1 | 10/2004 | Tjoa et al. | |
| 2005/0059151 A1 | 3/2005 | Bosch | |
| 2005/0119198 A1 | 6/2005 | Carmeliet et al. | |
| 2005/0169897 A1 | 8/2005 | Snyder et al. | |
| 2006/0003323 A1 | 1/2006 | Alsobrook et al. | |
| 2006/0204509 A1 | 9/2006 | Harty et al. | |
| 2007/0020297 A1 | 1/2007 | Wheeler et al. | |
| 2007/0098776 A1 | 5/2007 | Fikes et al. | |
| 2007/0167375 A1 | 7/2007 | Okada et al. | |
| 2008/0076904 A1 | 3/2008 | Cheever et al. | |
| 2008/0107668 A1 | 5/2008 | Philip et al. | |
| 2008/0131448 A1 | 6/2008 | Debinski et al. | |
| 2008/0166374 A1 | 7/2008 | Debinski et al. | |
| 2008/0199484 A1 | 8/2008 | Yu et al. | |
| 2008/0206286 A1 | 8/2008 | Yu | |
| 2008/0311141 A1 | 12/2008 | Yu et al. | |
| 2008/0311142 A1 | 12/2008 | Yu et al. | |
| 2009/0093052 A1 | 4/2009 | Yin et al. | |
| 2009/0110702 A1 | 4/2009 | Wu et al. | |
| 2009/0305418 A1 | 12/2009 | Moriarty et al. | |
| 2010/0040637 A1* | 2/2010 | Van Orden et al. | 424/172.1 |
| 2010/0135975 A1 | 6/2010 | Yu et al. | |
| 2010/0310643 A1 | 12/2010 | Singh et al. | |
| 2012/0052080 A1 | 3/2012 | Okada et al. | |
| 2012/0156232 A1 | 6/2012 | Yu et al. | |
| 2012/0189664 A1 | 7/2012 | Yu | |
| 2012/0231030 A1 | 9/2012 | Derouazi et al. | |
| 2013/0115279 A1 | 5/2013 | Singh et al. | |
| 2013/0183328 A1 | 7/2013 | Yu et al. | |
| 2013/0183378 A1 | 7/2013 | Yu et al. | |
| 2014/0234350 A1 | 8/2014 | Yu et al. | |
| 2014/0234351 A1 | 8/2014 | Yu et al. | |

FOREIGN PATENT DOCUMENTS

| | | |
|---|---|---|
| WO | WO 01/41741 | 6/2001 |
| WO | WO 01/58479 | 8/2001 |
| WO | WO 01/68148 | 9/2001 |
| WO | WO 02/068474 | 9/2002 |
| WO | WO 03/010301 | 2/2003 |
| WO | WO 03/014335 | 2/2003 |
| WO | WO 03/035004 | 5/2003 |
| WO | WO 03/066097 | 8/2003 |
| WO | WO 03/092717 | 11/2003 |
| WO | WO 2005/037995 | 4/2005 |
| WO | WO 2005/043155 | 5/2005 |
| WO | WO 2005/079581 | 9/2005 |
| WO | WO 2006/034334 | 3/2006 |
| WO | WO 2007/062138 | 5/2007 |
| WO | WO 2008/039874 | 4/2008 |
| WO | WO 2008/039969 | 4/2008 |
| WO | WO 2008/039974 | 4/2008 |
| WO | WO 2008/052740 | 5/2008 |
| WO | WO 2008/054716 | 5/2008 |
| WO | WO 2008/083949 | 7/2008 |
| WO | WO 2010/028066 | 3/2010 |
| WO | WO 2010/129895 | 11/2010 |
| WO | WO 2012/079000 | 6/2012 |

OTHER PUBLICATIONS

Yu et al., 2004, Canc. Res. vol. 64: 4973-4979.*
Xu et al.; "Isolation of tumour stem-like cells from benign tumours"; *British Journal of Cancer*; (2009) 101, pp. 303-311.
Ahmed et al.; "HER2-Specific T Cells Target Primary Glioblastoma Stem Cells and Induce Regression of Autologous Experimental Tumors"; Clin Cancer Res.; 16(2); 474-85.
Carpentier et al., 2009, Neuron, 64: 79-92.
Castelli et al., "Novel HLA-Cw8-restricted T cell epitopes derived from tyrosinase-related protein-2 and gp100 melanoma antigens," J. Immunol., 162:1739-48 (1999).
Chen et al., "Identification of the MAGE-1 gene product by monoclonal and polyclonal antibodies," Proc. Natl. Acad. Sci. USA, 91:1004-08 (1994).
Czerniecki et al., "Targeting HER-2/neu in early breast cancer development using dendritic cells with staged interleukin-12 burst secretion," Cancer Res., 67:1842-52 (2007).
Debinsky, "Correspondence re: B. H. Joshi et al., Interluekin-13 Receptor I Chain: A Novel Tumor-associated Transmembrane Protein in Primary Explants of Human Malignant Gliomas. Cancer Res., 60: 1168-1172, 2000," Cancer Res., 61:5660 (2001).
Dietz, "Engineering dendritic cell grafts for clinical trials in cellular immunotherapy of cancer: example of chronic myelogenous leukemia," Croatian Med. J., 42:428-435 (2001).
European Patent Office Communication for European Application No. 09812172.6, mailed May 23, 2012, 5 pages.
Garcia-Hernandez et al., "Prostate Stem Cell Antigen Vaccination Induces a Long-term Protective Immune Response against Prostate Cancer in the Absence of Autoimmunity", Cancer Res., vol. 68, No. 3, (2008), pp. 861-869.
Gearhart, 1998, Science, 282: 1061-1062.
Haas et al., "Cycloxygenase-2 inhibition augments the efficacy of a cancer vaccine," Clin. Cancer Res., 12:214-222 (2006).
Hahn et al., "Short-term dietary administration of celecoxib enhances the efficacy of tumor lysate-pulsed dendritic cell vaccines in treating murine breast cancer," Int. J. Cancer, 118:2220-31 (2006).
Haynes et al., "Molecular characterization of the B" regulatory subunit gene family of *Arabidopsis* protein phosphatase 2A", Euro J. Biochem., vol. 260, (1999), pp. 127-136.
Hemmer et al., "Contribution of Individual Amino Acids Within MHC Molecule or Antigenic Peptide to TCR Ligand Potency," J. Immunol., 164:861-871 (2000).
International Preliminary Report on Patentability for App. Ser. No. PCT/US2010/034082, mailed Nov. 17, 2011, 5 pages.
International Preliminary Report on Patentability for App. Ser. No. PCT/US07/079846, mailed Apr. 9, 2009, 5 pages.
International Preliminary Report on Patentability of International Application No. PCT/US2009/055759, issued Mar. 8, 2011 (mailed Mar. 17, 2011).
International Search Report and Written Opinion of International Application No. PCT/US2009/055759, mailed Jun. 28, 2010.
International Search Report and Written Opinion of International Application No. PCT/US2010/034082, mailed Feb. 22, 2011, 9 pages.
International Search Report and Written Opinion; PCT/US2014/16562; Jun. 3, 2014; 37 pp.
International Search Report and Written Opinion; PCT/US2014/16610; Jun. 5, 2014; 24 pp.
International Search Report of International Application No. PCT/US07/79846, mailed Jul. 14, 2008, 10 pages.
International Search Report of International Application No. PCT/US07/79846, mailed Apr. 8, 2008, 9 pages.
Joshi et al., "Interleukin-13 receptor I chain: a novel tumor-associated transmembrane protein in primary explants of human malignant gliomas," Cancer Res., 60:1168-72 (2000).
Kalinski et al., "Prostaglandin E2 induces the final maturation of IL-12 deficient CD1a+CD83+ dendritic cells: the levels of IL-12 are determined during the final dendritic cell maturation and are resistant to further modulation," J. Immunol, 161:2804-09 (1998).
Kimchi-Sarfaty et al., "A "Silent" Polymorphism in the MDR1 Gene Changes Substrate Specificity", Science, vol. 315, (2007), pp. 525-528 (Erratum, 1 page).
Lemmel et al., "Differential quantitative analysis of MHC ligands by mass spectrometry using stable isotope labeling," Nat. Biotechnol., 22:450-454 (2004).
Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage," J. Exp. Med., 188:1005-16 (1998).
Lynch et al., "Flt3 ligand induces tumor regression and antitumor immune responses in vivo," Nat. Med., 3:625-631 (1997).
Mi et al., "Induced apoptosis supports spread of adenovirus vectors in tumors," Hum. Gene Ther., 12:1343-52 (2001).

(56) References Cited

OTHER PUBLICATIONS

NCBI GenBank Accession No. NM_006017 (Jul. 13, 2008).
Ngo, J. et al., "Computational Complexity, Protein Structure Prediction and the Levinthal Paradox", (1994), The Protein Folding Problem and Tertiary Structure Prediction, Merz et al. (eds.), Birkhauser Boston: Boston, MA, pp. 433 and 492-495.
Nielsen et al., "Reliable prediction of T-cell epitopes using neural networks with novel sequence representations," Protein Sci., 12:1007-1017 (2003).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma", J. Clin. Oncology, 29:330-336, (2011).
Ordonez et al.; "Value of Mesothelin Immunostaining in the Diagnosis of Mesothelioma"; Mod. Pathol., Mar. 2003; vol. 16, No. 3, pp. 192-197.
Parkhurst et al., "Identification of a shared HLA-A*0201-restricted T-cell epitope from the melanoma antigen tyrosinase-related protein 2 (TRP2)," Cancer Res., 58:4895-4901 (1998).
Parkhurst et al., "Improved Induction of Melanoma-Reactive CTL with Peptides from the Melanoma Antigen gp100 Modified at HLA-A*0201-Binding Residues," J. Immunol., 157:2539-2548 (1996).
Phuphanich et al., "Immune response correlation with progression-free survival in glioblastoma following dendritic cell immunotherapy (ICT-107)," J. Clin. Oncol., 28(15 suppl.):2097 (abstract) (2010).
Phuphanich et al., "Immune response correlation with progression-free survival in glioblastoma following dendritic cell immunotherapy (ICT-107)," poster presented at 2010 ASCO Annual Meeting, Jun. 4-8, 2010.
Pinilla et al., "Investigation of antigen-antibody interactions using a soluble, non-support-bound synthetic decapeptide library composed of four trillion (4 × 1012) sequences," Biochem. J., 301:847-853 (1994).
Pinilla et al., "Rapid identification of high affinity peptide ligands using positional scanning synthetic peptide combinatorial libraries," Biotechniques, 13:901-905 (1992).
Pisarra et al., "Human melanocytes and melanomas express novel mRNA isoforms of the tyrosinase-related protein-2/DOPAchrome tautomerase gene: molecular and functional characterization," J. Invest. Dermatol., 115:48-56 (2000).
Posnett et al., "A novel method for producing anti-peptide antibodies. Production of site-specific antibodies to the T cell antigen receptor beta-chain," J. Biol. Chem., 263:1719-25 (1988).
Rosenberg et al, "Immunologic and therapeutic evaluation of a synthetic peptide vaccine for the treatment of patients with metastatic melanoma," Nat. Med., 4:321-327 (1998).
Rudinger, J. "Characteristics of the amino acids as components of a peptide hormone sequence", Peptide Hormones, University Park Press: Baltimore, MD, pp. 107, 1976.
Sette et al., "Epitope-based vaccines: an update on epitope identification, vaccine design and delivery", Current Opinion in Immunology, vol. 15, (2003), pp. 461-470.
Singh, "ImmunoCellular Therapeutics, Ltd.," presentation at 13th Annual BIO CEO & Investor Conference, Feb. 14, 2011.
Smith et al., "CD133/prominin-1 is a potential therapeutic target for antibody-drug conjugates in hepatocellular and gastric cancers," Br. J. Cancer, 99:100-109 (2008).
Supplementary European Search Report for European Application No. 09812172.6, mailed May 4, 2012, 6 pages.
Tourdot et al., "A general strategy to enhance immunogenicity of low-affinity HLA-A2.1-associated peptides: implication in the identification of cryptic tumor epitopes", Eur. J. Immunol., vol. 30, (2000), pp. 3411-3421.
USPTO Final Office Action in U.S. Appl. No. 11/863,990, mailed May 12, 2011, 18 pages.
USPTO Final Office Action in U.S. Appl. No. 11/864,177, mailed May 13, 2011, 18 pages.
USPTO Non-Final Office Action in U.S. Appl. No. 11/863,990, mailed Aug. 26, 2010, 15 pages.
USPTO Non-Final Office Action in U.S. Appl. No. 11/864,177, mailed Aug. 26, 2010, 16 pages.
USPTO Final Office Action in U.S. Appl. No. 12/552,945, mailed Aug. 16, 2012, 13 pages.
USPTO Non-Final Office Action in U.S. Appl. No. 12/552,945, mailed Mar. 12, 2012, 20 pages.
USPTO Non-Final Office Action in U.S. Appl. No. 12/776,200, mailed Apr. 18, 2012, 10 pages.
USPTO Non-Final Office Action in U.S. Appl. No. 12/776,200, mailed Aug. 7, 2012, 14 pages.
Voet, D. and Voet, J., "Biochemistry", Section 6-3. Chemical Evolution, John Wiley and Sons, (1990), pp. 126-128.
Weigmann et al., "Prominin, a novel microvilli-specific polytopic membrane protein of the apical surface of epithelial cells, is targeted to plasmalemmal protrusions of non-epithelial cells", Cell Biology, Proc. Natl. Acad. Sci. USA, vol. 94, (1997), pp. 12425-12430.
Yamanaka et al; Vaccination of recurrent glioma patients with tumour lysate-pulsed dendritic cells elicits immune response: results of a clinical phase I/II trial; British Journal of Cancer (2003) 89, 1172-1179.
Yang et al., "Dendritic cells infected with a vaccinia vector carrying the human gp100 gene simultaneously present multiple specificities and elicit high-affinity T cells reactive to multiple epitopes and restricted by HLA-A2 and -A3," J Immunol., 164:4204-11 (2000).
Yu et al. "CD133 as a Potential Target of Anti-Cancer Stem Cell Immunotherapy: Identification of an HLA-A*02 Restricted CD133 Epitope. Abstract", Journal of Immunotherapy, Nov.-Dec. 2008, p. 928.
Yu et al., "Vaccination with tumor lysate-pulsed dendritic cells elicits antigen-specific, cytotoxic T-cells in patients with malignant glioma," Cancer Res., 64:4973-79 (2004).
Zhu et al., "Insertion of the dibasic motif in the flanking region of a cryptic self-determinant leads to activation of the epitope-specific T cells," J. Immunol., 175:2252-60 (2005).
Wang et al., "Identification of TRP-2 as a human tumor antigen recognized by cytotoxic T lymphocytes," J. Exp. Med., 184:2207-16 (1996).
International Preliminary Report on Patentability for App. Ser. No. PCT/US07/079857, mailed Apr. 9, 2009, 5 pages.
Al-Hajj et al., "Prospective identification of tumorigenic breast cancer cells," Proc. Natl. Acad. Sci. USA, 7:3983-88 (2003).
Abdel-Wahab et al., "Human dendritic cells, pulsed with either melanoma tumor cell lysates or the gp100 peptide(280-288), induce pairs of T-cell cultures with similar phenotype and lytic activity," Cell. Immunol., 186:63-74 (1998).
Akasaki et al., "Antitumor effect of immunizations with fusions of dendritic and glioma cells in a mouse brain tumor model," J. Immunother., 24:106-113 (2001).
Akasaki et al., "Induction of a CD4+ T regulatory type 1 response by cyclooxygenase-2-overexpressing glioma," J. Immunol., 173:4352-59 (2004).
Akasaki et al., "Dendritic cell-based immunotherapy for malignant gliomas," Expert Rev. Neurother., 5:497-508 (2005).
Akasaki et al., "T cell immunity in patients with malignant glioma: recent progress in dendritic cell-based immunotherapeutic approaches," Front. Biosci., 10:2908-21 (2005).
Altaner, "Glioblastoma and stem cells," Neoplasma, 55:369-374 (2008).
Beier et al., "CD133+ and CD133− glioblastoma-derived cancer stem cells show differential growth characteristics and molecular profiles," Cancer Res., 67:4010-15 (2007).
Bjerkvig et al., "Opinion: the origin of the cancer stem cell: current controversies and new insights," Nat. Rev. Cancer, 11:899-904 (2005).
Boman et al., "Cancer stem cells: a step toward the cure," J. Clin. Oncol., 26:2795-99 (2008).
Borbulevych et al., "Increased immunogenicity of an anchor-modified tumor-associated antigen is due to the enhanced stability of the peptide/MHC complex: implications for vaccine design," J. Immunol., 174:4812-20 (2005).

(56) References Cited

OTHER PUBLICATIONS

Borrás et al., "Findings on T cell specificity revealed by synthetic combinatorial libraries," J. Immunol. Methods, 267:79-97 (2002).
Bowles, Jr. et al., "Long-term remission of malignant brain tumors after intracranial infection: a report of four cases," Neurosurgery, 44:636-642 (1999).
Brown et al., "Recognition and killing of brain tumor stem-like initiating cells by CD8+ cytolytic T cells," Cancer Res., 69:8886-93 (2009).
Bullock et al., "Antigen density presented by dendritic cells in vivo differentially affects the number and avidity of primary, memory, and recall CD8+ T cells," J. Immunol., 170:1822-29 (2003).
Candido et al., "Local administration of dendritic cells inhibits established breast tumor growth: implications for apoptosis-inducing agents," Cancer Res., 61:228-236 (2001).
Casey et al., "Heat shock protein derived from a non-autologous tumour can be used as an anti-tumour vaccine," Immunology, 110:105-111 (2003).
Castro et al., "Current and future strategies for the treatment of malignant brain tumors," Pharmacol. Ther., 98:71-108 (2003).
Chandler et al., "Long-term survival in patients with glioblastoma multiforme," Neurosurgery, 32:716-720 (1993).
Cho et al., "Recent advances of dendritic cells (DCs)-based immunotherapy for malignant gliomas," Cell Transplant., 18:977-983 (2009).
Curran et al., "Recursive partitioning analysis of prognostic factors in three radiation therapy oncology group malignant glioma trials," J. Natl. Cancer Inst., 85:704-710 (1993).
Drukker et al., "Characterization of the expression of MHC proteins in human embryonic stem cells," Proc. Natl. Acad. Sci. USA, 99:9864-69 (2002).
Ehtesham et al., "Intratumoral dendritic cell vaccination elicits potent tumoricidal immunity against malignant glioma in rats," J. Immunother., 2:107-116 (2003).
Ehtesham et al., "Recent progress in immunotherapy for malignant glioma: treatment strategies and results from clinical trials," Cancer Control, 11:192-207 (2004).
Communication for Application No. EP 07843269.7, dated Feb. 2, 2011, 9 pages.
Falk et al., "Allele-specific motifs revealed by sequencing of self-peptides eluted from MHC molecules," Nature, 351:290-296 (1991).
Friedman et al., "Temozolomide and treatment of malignant glioma," Clin. Cancer Res., 6:2585-97 (2000).
Galli et al., "Isolation and characterization of tumorigenic, stem-like neural precursors from human glioblastoma," Cancer Res., 64:7011-21 (2004).
Gatza et al., "Tumor cell lysate-pulsed dendritic cells are more effective than TCR Id protein vaccines for active immunotherapy of T cell lymphoma," J. Immunol., 169:5227-35 (2002).
Geiger et al., "Vaccination of pediatric solid tumor patients with tumor lysate-pulsed dendritic cells can expand specific T cells and mediate tumor regression," Cancer Res., 61:8513-19 (2001).
Geschwind et al., "A genetic analysis of neural progenitor differentiation," Neuron, 2:325-39 (2001).
Ghods et al., "Spheres isolated from 9L gliosarcoma rat cell line possess chemoresistant and aggressive cancer stem-like cells," Stem Cells, 7:1645-53 (2007).
Gilboa et al., "Immunotherapy of cancer with dendritic-cell-based vaccines," Cancer Immunol, Immunother., 46:82-87 (1998).
Harada et al., "Melanoma-reactive CD8+ T cells recognize a novel tumor antigen expressed in a wide variety of tumor types," J. Immunother., 24:323-333 (2001).
Harizi et al., "Prostaglandin E2 modulates dendritic cell function via EP2 and EP4 receptor subytpes," J. Leukocyte Biol., 73:756-763 (2003).
Heimberger et al., "Bone marrow-derived dendritic cells pulsed with tumor homogenate induce immunity against syngeneic intracerebral glioma," J. Neuroimmunol., 103:16-24 (2000).
Hemmati et al., "Cancerous stem cells can arise from pediatric brain tumors," Proc. Natl. Acad. Sci. USA, 25:15178-83 (2003).
Hirschmann-Jax et al., "A distinct 'side population' of cells with high drug efflux capacity in human tumor cells," Proc. Natl. Acad. Sci. USA, 39:14228-33 (2004).
Hori et al., "Neural progenitor cells lack immunogenecity and resist destruction as allografts," Stem Cells, 21:405-416 (2003).
Inoue et al., "Dendritic cells coinjected with tumor cells treated with an anticancer drug to induce tumor rejection," Surg. Today, 33:269-276 (2003).
International Search Report and Written Opinion of the International Searching Authority for PCT/US2007/79600, mailed on Mar. 27, 2008, 10 pages.
Irvin et al., "T cells enhance stem-like properties and conditional malignancy in gliomas," PLoS One, 5:e10974 (2010).
Ji et al., "Gloma stem cell research for the development of immunotherapy," Neurosurg. Clin. N. Am., 21:159-66 (2010).
Khong et al., "Pre-existing immunity to tyrosinase-related protein (TRP)-2, a new TRP-2 isoform, and the NY-ESO-1 melanoma antigen in a patient with a dramatic response to immunotherapy," J. Immunol, 168:951-956 (2002).
Kikuchi et al., "Intratumoral injection of dendritic and irradiated glioma cells induces anti-tumor effects in a mouse brain tumor model," Cancer Immunol. Immumother., 51:424-430 (2002).
Kikuchi et al., "Results of a phase I clinical trial of vaccination of glioma patients with fusions of dendritic and glioma cells," Cancer Immunol. Immumother., 50:337-344 (2002).
Knutson et al., "Technology evaluation: DCVax, Northwest Biotherapeutics," Curr. Opin. Mol. Ther., 4:403-407 (2002).
Koch et al., "Immune-privileged embryonic Swiss mouse STO and STO cell-derived progenitor cells: major histocompatibility complex and cell differentiation antigen expression patterns resemble those of human embryonic stem cell lines," Immunology, 119:98-115 (2006).
Kuby et al., Immunology, W. H. Freeman and Co., pp. 523-524 (1992).
La Rosa et al., "Enhanced immune activity of cytotoxic T-lymphocyte epitope analogs derived from positional scanning synthetic combinatorial libraries," Blood, 97:1776-86 (2001).
Lefranc, "Editorial: On the road to multi-modal and pluri-disciplinary treatment of glioblastomas," Acta Neurochir. (Wien), 151:109-112 (2009).
Lee et al., "Isolation of neural stem cells from the postnatal cerebellum," Nat. Neurosci., 6:723-729 (2005).
Li et al., "Human embryonic stem cells possess immune-privileged properties," Stem Cells, 22:448-456 (2004).
Liau et al., "Treatment of intracranial gliomas with bone marrow-derived dendritic cells pulsed with tumor antigens," J. Neurosurg., 90:1115-24 (1999).
Liu and Yu, "Cancer vaccines: a novel strategy to sensitize malignant glioma to chemotherapy," Expert Rev. Neurother., 7:1235-37 (2007).
Liu et al., "Analysis of gene expression and chemoresistance of CD133+ cancer stem cells in glioblastoma," Mol. Cancer, 5:67 (2006).
Liu et al., "Cell-mediated immunotherapy: a new approach to the treatment of malignant glioma," Cancer Control, 10:138-147 (2003).
Liu et al., "Small interference RNA modulation of IL-10 in human monocyte-derived dendritic cells enhances the Th1 response," Eur. J. Immunol., 34:1680-87 (2004).
Liu et al., "AIM-2: a novel tumor antigen is expressed and presented by human glioma cells," J. Immunother., 27:220-226 (2004).
Liu et al., "Cytotoxic T cell targeting of TRP-2 sensitizes human malignant glioma to chemotherapy," Oncogene, 24:5226-34 (2005).
Liu et al., "HER-2, gp100, and MAGE-1 are expressed in human glioblastoma and recognized by cytotoxic T cells," Cancer Res., 64:4980-86 (2004).
Liu et al., "Molecular and functional analysis of tyrosinase-related protein (TRP)-2 as a cytotoxic T lymphocyte target in patients with malignant glioma," J. Immunother., 26:301-312 (2003).
Liu et al., "Sensitization of malignant glioma to chemotherapy through dendritic cell vaccination," Expert Rev. Vaccines, 5:233-247 (2006).
Liu et al,, "Chemoresistance of stem-like cells isolated from glioblastoma," Proc. Amer. Assoc. Cancer Res., 47:75, abstract #320 (2006).

(56) References Cited

OTHER PUBLICATIONS

Luptrawan et al., "Dendritic cell immunotherapy for malignant gliomas," Rev. Recent Clin. Trials, 3:10-21 (2008).
Lustgarten et al., "Identification of cross-reactive peptides using combinatorial libraries circumvents tolerance against Her-2/neu-immunodominant epitope," J. Immunol., 176:1796-1805 (2006).
Maitland and Collins, "Prostate cancer stem cells: a new target for therapy," J. Clin. Oncol., 26:2862-70 (2008).
Mammolenti et al., "Absence of major histocompatibility complex class I on neural stem cells does not permit natural killer cell killing and prevents recognition by alloreactive cytotoxic T lymphocytes in vitro," Stem Cells, 22:1101-10 (2004).
Mehta-Damani et al., "Generation of antigen-specific CD4+ T cell lines from naïve precursors," Eur. J. Immunol., 5:1206-11 (1995).
Mehta-Damani et al., "Generation of antigen-specific CD8+ CTLs from naive precursors," J. Immunol., 153:996-1003 (1994).
Melcher et al., "Dendritic cells for the immunotherapy of cancer," Clin. Oncol., 14:185-192 (2002).
Merrick et al., "Autologous versus allogeneic peptide-pulsed dendritic cells for anti-tumour vaccination: expression of allogeneic MHC supports activation of antigen specific T cells, but impairs early naïve cytotoxic priming and anti-tumour therapy," Cancer Immunol. Immunother., 57:897-906 (2008).
Mizrak et al., "CD133: molecule of the moment," J. Pathol., 214:3-9 (2008).
Neuzil et al., "Tumour-initiating cells vs. cancer 'stem' cells and CD133: what's in the name?" Biochem. Biophys. Res. Commun., 355:855-859 (2007).
Nowak et al., "Synergy between chemotherapy and immunotherapy in the treatment of established murine solid tumors," Cancer Res., 63:4490-96 (2003).
O'Brien et al., "A human colon cancer cell capable of initiating tumour growth in immunodeficient mice," Nature, 7123:106-110 (2007).
Okada et al., "Bone marrow-derived dendritic cells pulsed with a tumor-specific peptide elicit effective anti-tumor immunity against intracranial neoplasms," Int. J. Cancer, 78:196-201 (1998).
Okada et al., "Autologous glioma cell vaccine admixed with interleukin-4 gene transfected fibroblasts in the treatment of recurrent glioblastoma: preliminary observations in a patient with a favorable response to therapy," J. Neurooncol., 64:13-20 (2003).
Okano et al., "Identification of a novel HLA-A*0201-restricted, cytotoxic T lymphocyte epitope in a human glioma-associated antigen, interleukin 13 receptor I2 chain," Clin. Cancer Res., 8:2851-55 (2002).
Osada et al., "Dendritic cells activate antitumor immunity for malignant intracranial germ cell tumor: a case report," Jpn. J. Clin. Oncol., 31:403-406 (2001).
Parmiani et al., "Cancer immunotherapy with peptide-based vaccines: What have we achieved? Where are we going?" J. Natl. Cancer Inst., 94:805-818 (2002).
Parney et al., "Glioma immunology and immunotherapy," Neurosurgery, 46:778-791 (2000).
Pellegatta et al., "Dendritic cell vaccines for cancer stem cells," Methods Mol. Biol., 568:233-247 (2009).
Pellegatta et al., "Neurospheres enriched in cancer stem-like cells are highly effective in eliciting a dendritic cell-mediated immune response against malignant gliomas," Cancer Res., 66:10247-52 (2006).
Pirtsktialaishvili et al., "Cytokine-mediated protection of human dendritic cells from prostate cancer induced apoptosis is regulated by the Bcl-2 family of proteins," Br. J. Cancer, 83:506-513 (2000).
Pollack et al., "Exploitation of immune mechanisms in the treatment of central nervous system cancer," Semin. Pediatr. Neurol., 7:131-143 (2000).
Reichardt et al., "Idiotype vaccination of multiple myeloma patients using monocyte-derived dendritic cells," Haematologica, 88:1139-49 (2003).
Reya et al., "Stem cells, cancer, and cancer stem cells," Nature, 6859:105-111 (2001).
Reynolds and Weiss, "Generation of neurons and astrocytes from isolated cells of the adult mammalian central nervous system," Science, 5052:1707-10 (1992).
Reynolds et al, "A multipotent EGF-responsive striatal embryonic progenitor cell produces neurons and astrocytes," J. Neurosci., 11:4565-74 (1992).
Rissoan et al., "Reciprocal control of T helper cell and dendritic cell differentiation," Science, 283:1183-86 (1999).
Rosenberg et al., "Immunologic and therapeutic evaluation of a synthetic peptide vaccine for the treatment of patients with metastatic melanoma," Nat. Med., 4:321-327 (1998).
Salgaller et al., "Recognition of multiple epitopes in the human melanoma antigen gp100 by peripheral blood lymphocytes stimulated in vitro with synthetic peptides," Cancer Res., 55:4972-79 (1995).
Sanai et al., "Neural stem cells and the origin of gliomas," N. Eng. J. Med., 8:811-822 (2005).
Shin et al., "Antitumor effect of intratumoral administration of dendritic cell combination with vincristine chemotherapy in a murine fibrosarcoma model," Histol. Histopathol., 18:435-447 (2003).
Singh et al., "Cancer stem cells in nervous tumors," Oncogene, 23:7267-73 (2004).
Singh et al., "Identification of a cancer stem cell in human brain tumors," Cancer Res., 63:5821-28 (2003).
Singh et al., "Identification of human brain tumor initiating cells," Nature, 7015:396-401 (2004).
Soling et al., "Dendritic cell therapy of primary brain tumors," Mol. Med., 7:659-667 (2001).
Song et al., "Strategies to improve dendritic cell-based immunotherapy against cancer," Yonsei Med. J., 45(Suppl):48-52 (2004).
Steele et al., "The polycomb group proteins, BMI-1 and EZH2, are tumour-associated antigens," Br. J. Cancer 95:1202-11 (2006).
Steinbrink et al., "CD4+ and CD8+ anergic T cells induced by interleukin-10-treated human dendritic cells display antigen-specific suppressor activity," Blood, 99:2468-76 (2002).
Steinman, "Some interfaces of dendritic cell biology," APMIS, 111:675-697 (2003).
Storkus et al., "Identification of human melanoma peptides recognized by class I restricted tumor infiltrating T lymphocytes," J. Immunol., 151:3719-27 (1993).
Stupp et al., "Recent Developments in the Management of Malignant Glioma," American Society of Clinical Oncology Educational Book, 779-788 (2003).
Takagi et al., "Anti-tumor effects of dendritic and tumor cell fusions are not dependent on expression of MHC class I and II by dendritic cells," Cancer Lett., 213:49-55 (2004).
Tanaka et al., "Intratumoral injection of dendritic cells after treatment of anticancer drugs induces tumor-specific antitumor effect in vivo," Int. J. Cancer, 101:265-269 (2002).
Tanaka et al., "Intratumoral injection of immature dendritic cells enhances antitumor effect of hyperthermia using magnetic nanoparticles," Int. J. Cancer, 116:624-633 (2005).
Tian et al., "Expression of immunoglobulin superfamily cell adhesion molecules on murine embryonic stem cells," Biol. Reprod., 57:561-568 (1997).
Tong et al., "Combined intratumoral injection of bone marrow-derived dendritic cells and systemic chemotherapy to treat pre-existing murine tumors," Cancer Res., 61:7530-35 (2001).
Tunici et al., "Genetic alterations and in vivo tumorigenicity of neurospheres derived from an adult glioblastoma," Mol. Cancer, 3:25 (2004).
Tunici et al., "Brain tumor stem cells: new targets for clinical treatments?" Neurosurg. Focus, 4:E27 (2006).
Wang et al., "An effective cancer vaccine modality: lentiviral modification of dendritic cells expressing multiple cancer-specific antigens," Vaccine, 24:3477-89 (2006).
Wei et al., "Dendritic cells expressing a combined PADRE/MUC4-derived polyepitope DNA vaccine induce multiple cytotoxic T-cell responses," Cancer Biother. Radiopharm., 23:121-128 (2008).
Weigel et al., "Dendritic cells pulsed or fused with AML cellular antigen provide comparable in vivo antitumor protective responses," Exp. Hematol., 34:1403-12 (2006).

(56) References Cited

OTHER PUBLICATIONS

Westphal et al., "Other experimental therapies for glioma," Recent Results Cancer Res., 171:155-164 (2009).
Wheeler et al., "Cellular immunity in the treatment of brain tumors," Clin. Neurosurg., 51:132-139 (2004).
Wheeler et al., "Clinical responsiveness of glioblastoma multiforme to chemotherapy after vaccination," Clin. Cancer Res., 10:5316-26 (2004).
Wheeler et al., "Thymic CD8+ T cell production strongly influences tumor antigen recognition and age-dependent glioma mortality," J. Immunol., 171:4927-33 (2003).
Wheeler et al., "Vaccination elicits correlated immune and clinical responses in glioblastoma multiforme patients," Cancer Res., 68:5955-64 (2008).
Wu et al., "Embryonic stem cells and their differentiated derivatives have fragile immune privilege but still represent novel targets of immune attack," Stem Cells, 26:1939-50 (2008).
Wu et al., "Expression of MHC I and NK ligands on human CD133+ glioma cells: possible targets of immunotherapy," J. Neurooncol., 83:121-131 (2007).
Xu et al., "Antigen-specific T-cell response from dendritic cell vaccination using cancer stem-like cell-associated antigens," Stem Cells, 27:1734-40 (2009).
Xu et al., "Hedgehog signaling regulates brain tumor-initiating cell proliferation and portends shorter survival for patients with PTEN-coexpressing glioblastomas," Stem Cells, 26:3018-26 (2008).
Yamazaki et al., "Direct expansion of functional CD25+ CD4+ regulatory T cells by antigen-processing dendritic cells," J. Exp. Med., 198:235-247 (2003).
Yang et al., "Modulation of major histocompatibility complex Class I molecules and major histocompatibility complex-bound immunogenic peptides induced by interferon-alpha and interferon-gamma treatment of human glioblastoma multiforme," J. Neurosurg., 100:310-319 (2004).
Yasuda et al., "Dendritic cell-tumor cell hybrids enhance the induction of cytotoxic T lymphocytes against murine colon cancer: a comparative analysis of antigen loading methods for the vaccination of immunotherapeutic dendritic cells," Oncol. Rep., 16:1317-24 (2006).
Yin et al., "Expression and regulation of major histocompatibility complex on neural stem cells and their lineages," Stem Cells Dev., 17:53-65 (2008).
Yin et al., "AC133, a novel marker for human hematopoietic stem and progenitor cells," Blood, 12:5002-12 (1997).
Yu et al., "AC133-2, a novel isoform of human AC133 stem cell antigen," J. Biol. Chem., 23:20711-16 (2002).
Yu et al., "Effective combination of chemotherapy and dendritic cell administration for the treatment of advanced-stage experimental breast cancer," Clin. Cancer Res., 9:285-294 (2003).
Yu et al., "Mahaley Clinical Research Award: chemosensitization of glioma through dendritic cell vaccination," Clin. Neurosurg., 53:345-351 (2006).
Yu et al., "Vaccination of malignant glioma patients with peptide-pulsed dendritic cells elicits systemic cytotoxicity and intracranial T-cell infiltration," Cancer Res., 61:842-847 (2001).
Young et al., "Dendritic cells stimulate primary human cytolytic lymphocyte responses in the absence of CD4+ helper T cells," J. Exp. Med., 171:1315-32 (1990).
Yuan et al., "Isolation of cancer stem cells from adult glioblastoma multiforme," Oncogene, 58:9392-9400 (2004).
Zabierowski and Herlyn, "Melanoma stem cells: the dark seed of melanoma," J. Clin. Oncol., 26:2890-94 (2008).
Zagzag et al., "Downregulation of major histocompatibility complex antigens in invading glioma cells: stealth invasion of the brain," Lab. Invest., 85:328-341 (2005).
Zeidler et al., "Tumor cell-derived prostaglandin E2 inhibits monocyte function by interfering with CCR5 and Mac-1," FASEB J., 14:661-668 (2000).
Zhang et al., "Antigenic profiling of glioma cells to generate allogeneic vaccines or dendritic cell-based therapeutics," Clin. Cancer Res., 13:566-575 (2007).
Zitvogel et al., "Therapy of murine tumors with tumor peptide-pulsed dendritic cells: dependence on T cells, B7 costimulation, and T helper cell-1 associated cytokines," J. Exp. Med., 183:87-97 (1996).
Zhou et al., "The ABC transporter Berp1/ABCG2 is expressed in a wide variety of stem cells and is a molecular determinant of the side-population phenotype," Nat. Med., 9:1028-34 (2001).
Zou et al., "Cancer initiating cells or cancer stem cells in the gastrointestinal tract and liver," J. Cell. Physiol., 217:598-604 (2008).
Feng et al., "P55, an Immunogenic but Nonprotective 55-Kilodalton *Borrelia burgdorferi* Protein in Murine Lyme Disease", Infection and Immunity, 336-365 (1996).
USPTO Final Office action in U.S. Appl. No. 13/826,737, mailed Oct. 24, 2014, 33 pages.
USPTO Final Office Action in U.S. Appl. No. 12/552,945, mailed Oct. 22, 2014, 27 pages.
Van Der Burg et al., "Immunogenicity of Peptides Bound to MHC Class I Molecules Depends on the MHC-Peptide Complex Stability", J. Immunol., 156:3308-3314 (1996).
Zhang et al., "Extensively cross-reactive anti-HIV-1 neutralizing antibodies induced by gp140 immunization," PNAS 24:10193-10198 (2007).

* cited by examiner

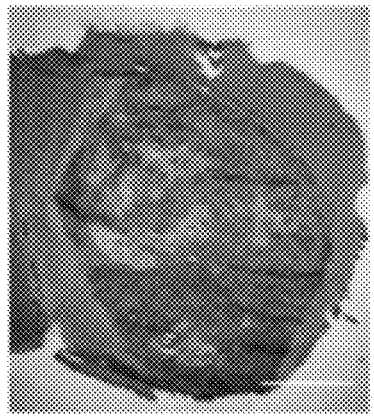
FIG. 5A
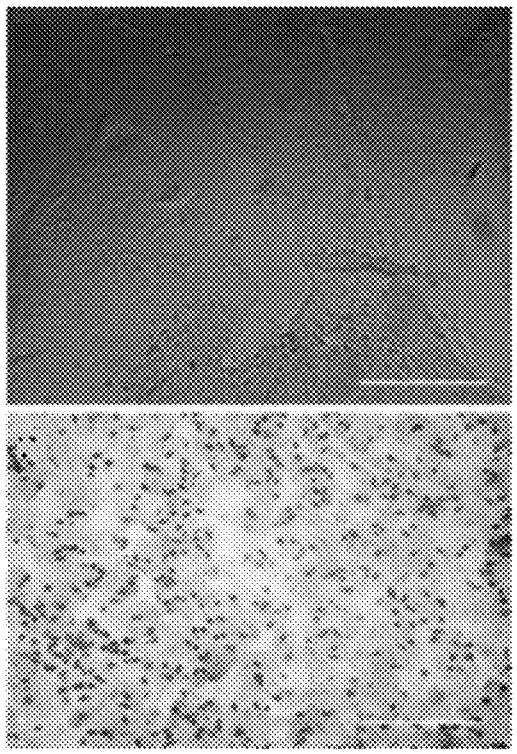
FIG. 5B
FIG. 5D
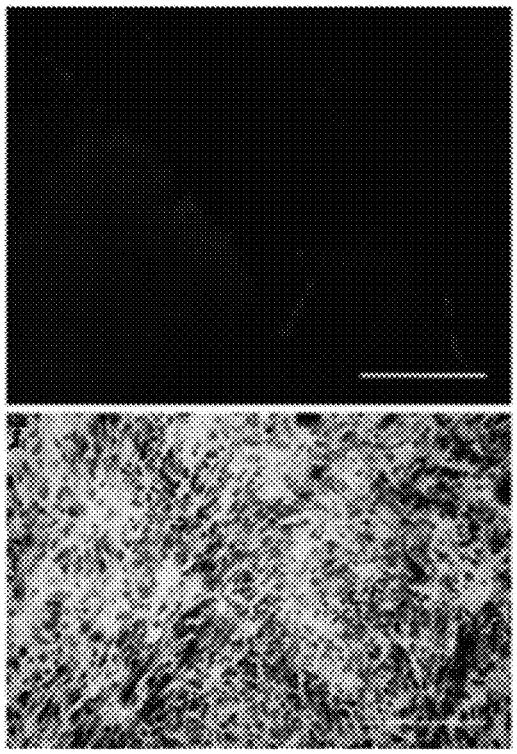
FIG. 5C
FIG. 5E

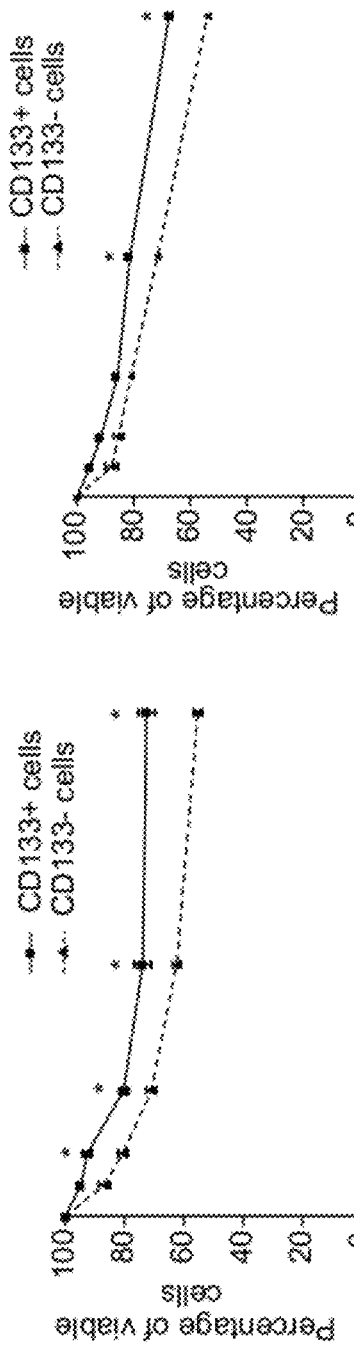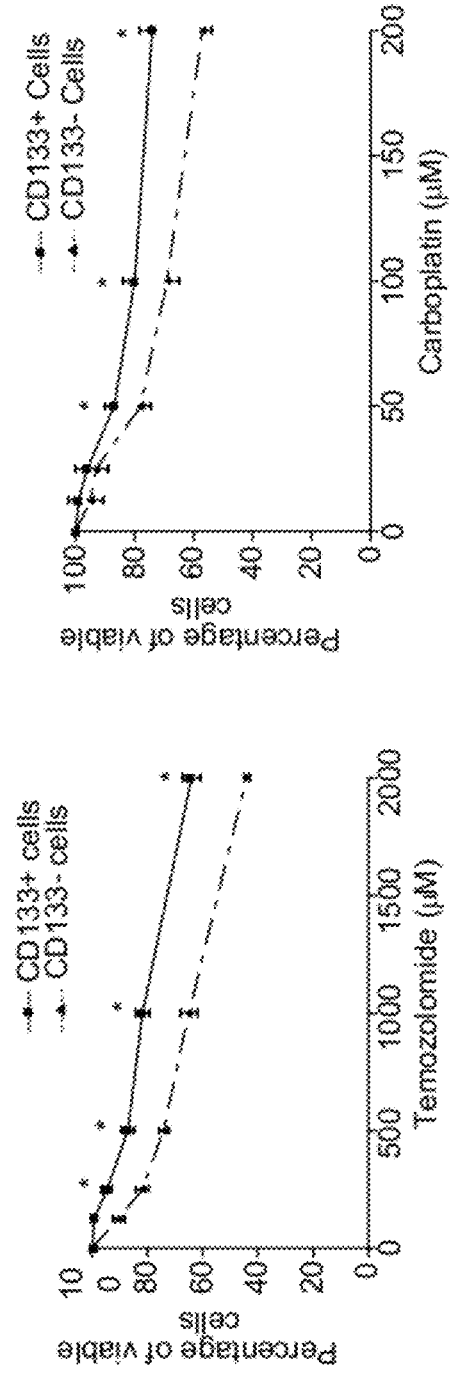

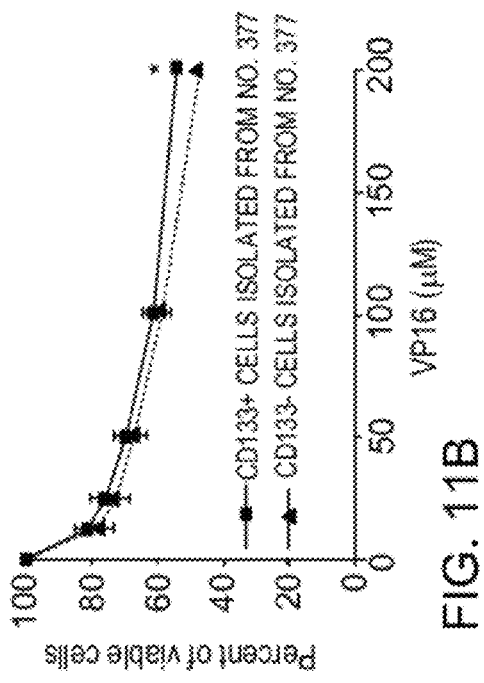
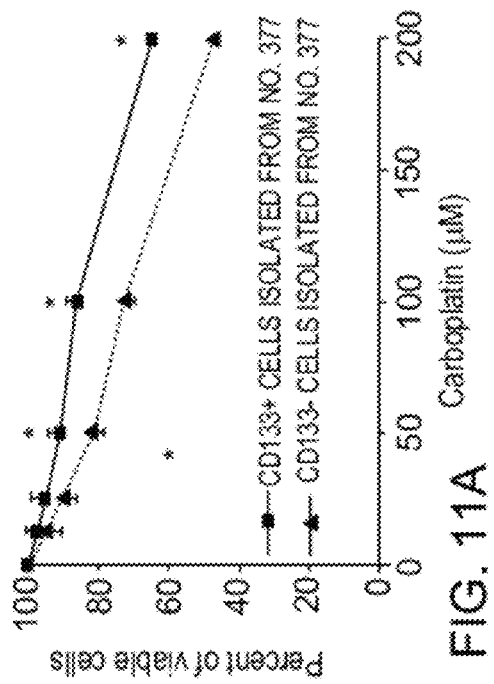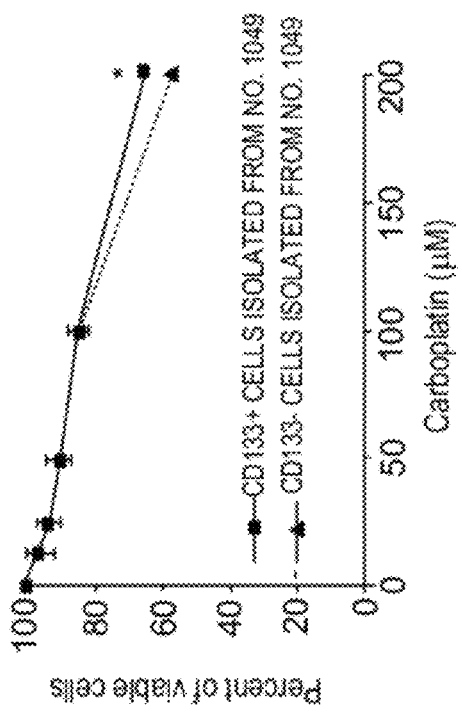
FIG. 11A
FIG. 11B
FIG. 11C

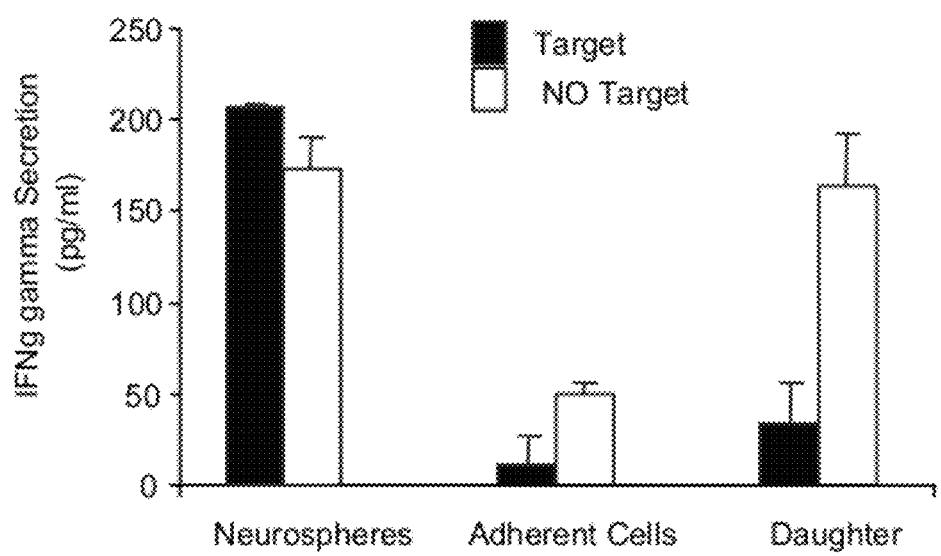
FIG. 14
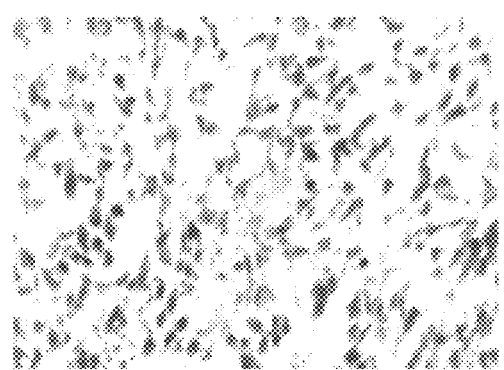 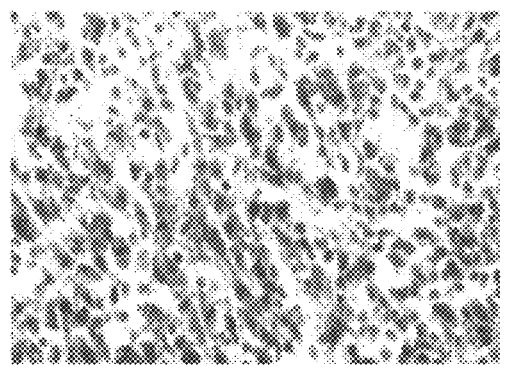
FIG. 15A                FIG. 15B

Structural model of CD133 antigen

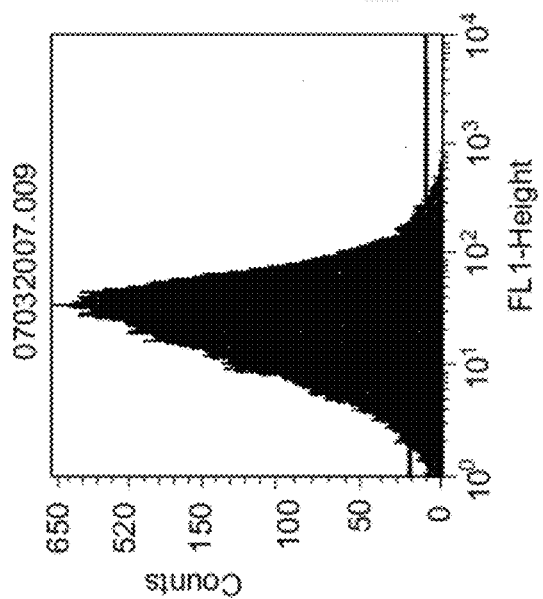
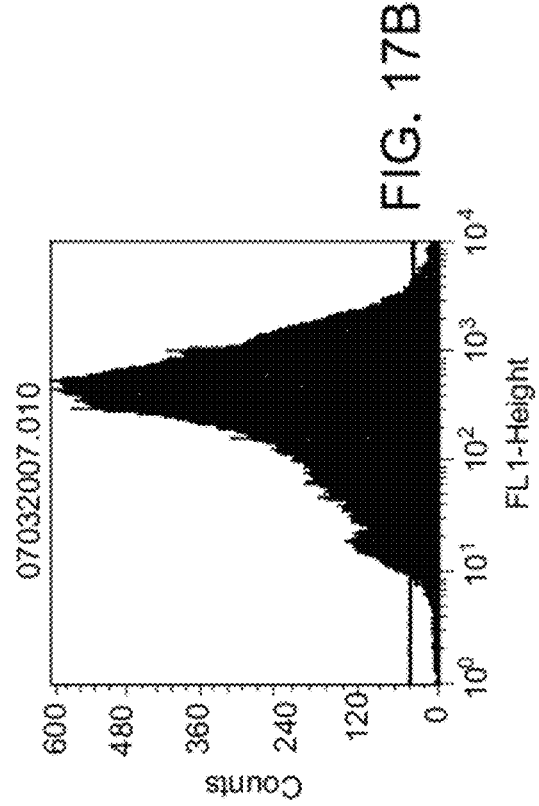
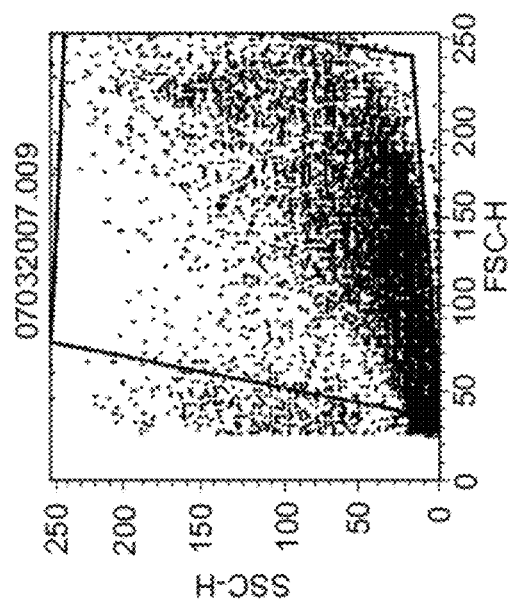
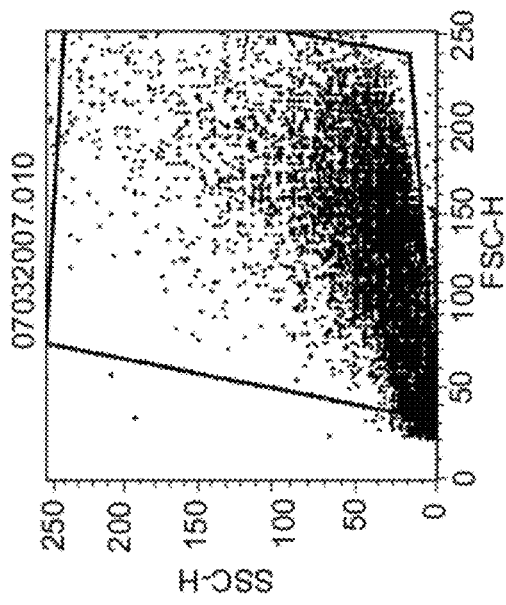
FIG. 17A
FIG. 17B

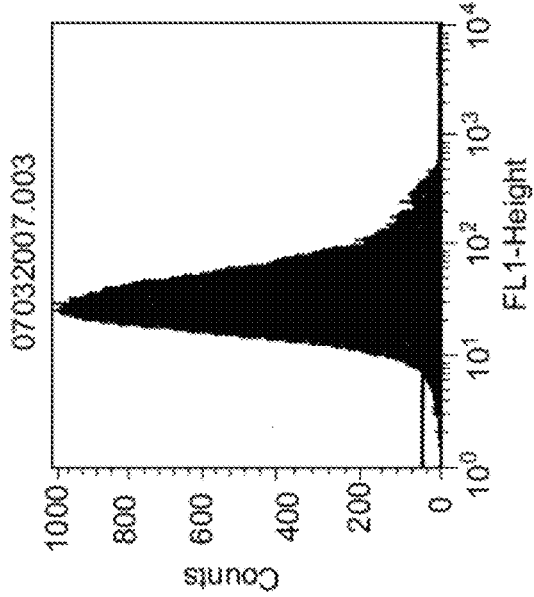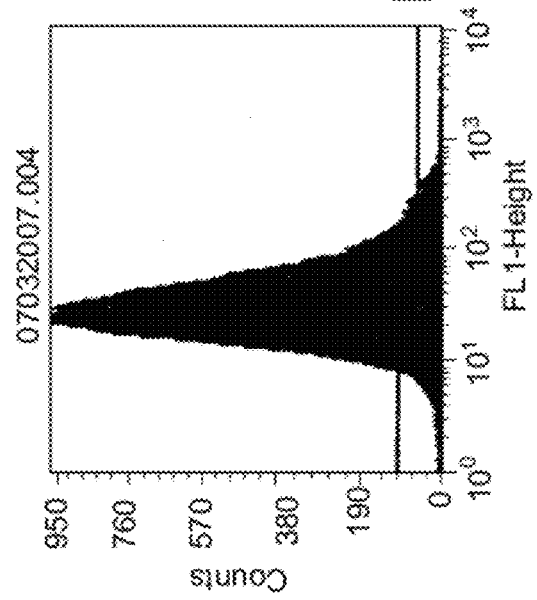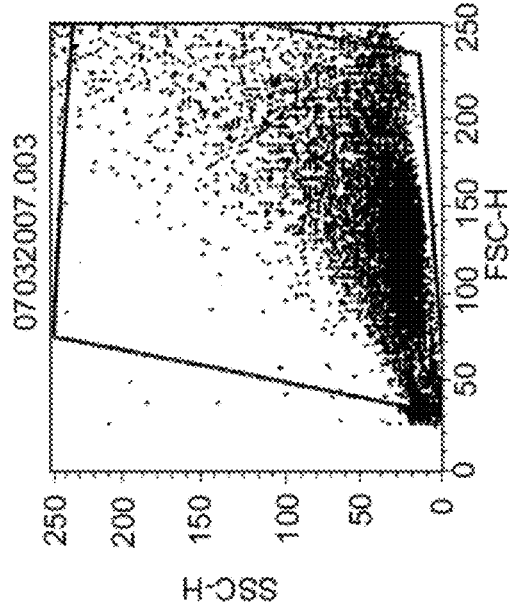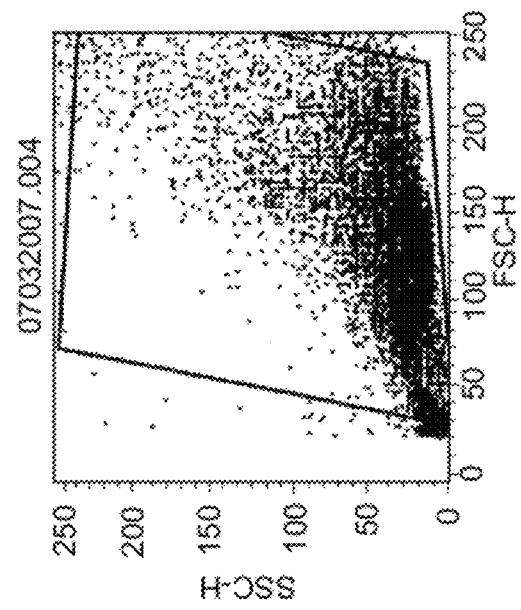
FIG. 18A
FIG. 18B

SEQUENCE LISTING

<160> NUMBER OF SEQ ID NOS: 105

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ttctacaatg agctgcgtgt                                           20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggggtgttga aggtctcaaa                                           20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gcattggcat cttctatggt t                                         21

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
cgccttgtcc ttggtagtgt                                           20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gagactgacg cgccccagcc                                           20

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
cgcctggtcc atgaaagtga cg                                        22

<210> SEQ ID NO 7
<211> LENGTH: 26
<212> TYPE: DNA
<213> ORGANISM: Artificial Sequence

```
<220> FEATURE:
<223> OTHER INFORMATION: primer

<400> SEQUENCE: 7
cttggatcag aggcagatgt ttggag                                    26

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
gttgtaatct tgcatgatcc agg                                       23

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ggcggggcag tgcctttcaa a                                         21

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
tgttggctgc gtctcatcaa aacc                                      24

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cgctctcctg ctaacagtct t                                         21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
caggctgaac tcgtactgga                                           20

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
atcgctcagg tcctggaa                                             18
```

```
<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
aagctgaggg aagtcttgga                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
agaaggtgtg ggcagaagaa                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
aaatgcacca tttcctgaga                                              20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
agggaggaaa gcagactgac                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ccagtcattt ccacaccact                                              20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gatcagcatc gactccttca                                              20

<210> SEQ ID NO 20
<211> LENGTH: 20
<212> TYPE: DNA
<213> ORGANISM: Artificial Sequence
<220> FEATURE:
<223> OTHER INFORMATION: primer
```

```
<400> SEQUENCE: 20
ggctccaagg aaagcataga                                              20

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
ggagaccagc aagtattgtc cttttg                                       26

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
cattgctgct gggcatcgta ag                                           22

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
cgcctatgcc tgtctaacca tgc                                          23

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
aaatggcaaa acctgagttg                                              20

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
accactatgc cgcgctctt                                               19

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
ggtcgtaggg ctgctggaa                                               19

<210> SEQ ID NO 27
```

```
<211> LENGTH: 20
<212> TYPE: DNA
<213> ORGANISM: Artificial Sequence
<220> FEATURE:
<223> OTHER INFORMATION: primer

<400> SEQUENCE: 27
acttgtacga cgaagacgac                                                    20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
cagaaggtta tctcggtacc                                                    20

<210> SEQ ID NO 29
<211> LENGTH: 17
<212> TYPE: DNA
<213> ORGANISM: Artificial Sequence
<220> FEATURE:
<223> OTHER INFORMATION: primer

<400> SEQUENCE: 29
tgcctggcag ccctttc                                                       17

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cctccaagaa gggccagttc                                                    20

<210> SEQ ID NO 31
<211> LENGTH: 19
<212> TYPE: DNA
<213> ORGANISM: Artificial Sequence
<220> FEATURE:
<223> OTHER INFORMATION: primer

<400> SEQUENCE: 31
cagcctgagc agcttgcaa                                                     19

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
caagccacca tcacaacaaa a                                                  21

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
```

```
tccgtcaagt tcaagccagt t                                              21

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
tctcctgggc tgtctgatgt g                                              21

<210> SEQ ID NO 35
<211> LENGTH: 18
<212> TYPE: DNA
<213> ORGANISM: Artificial Sequence
<220> FEATURE:
<223> OTHER INFORMATION: primer

<400> SEQUENCE: 35
gcttcacagc gcatcgaa                                                  18

<210> SEQ ID NO 36
<211> LENGTH: 17
<212> TYPE: DNA
<213> ORGANISM: Artificial Sequence
<220> FEATURE:
<223> OTHER INFORMATION: primer

<400> SEQUENCE: 36
gctgggcgga tgctttc                                                   17

<210> SEQ ID NO 37
<211> LENGTH: 24
<212> TYPE: DNA
<213> ORGANISM: Artificial Sequence
<220> FEATURE:
<223> OTHER INFORMATION: primer

<400> SEQUENCE: 37
agtggtagtc ctgtttcagc atca                                           24

<210> SEQ ID NO 38
<211> LENGTH: 19
<212> TYPE: DNA
<213> ORGANISM: Artificial Sequence
<220> FEATURE:
<223> OTHER INFORMATION: primer

<400> SEQUENCE: 38
ccgcacggta tctccttca                                                 19

<210> SEQ ID NO 39
<211> LENGTH: 18
<212> TYPE: DNA
<213> ORGANISM: Artificial Sequence
<220> FEATURE:
<223> OTHER INFORMATION: primer

<400> SEQUENCE: 39
catgctgggg ccgtacag                                                  18

<210> SEQ ID NO 40
<211> LENGTH: 18
<212> TYPE: DNA
```

```
<213> ORGANISM: Artificial Sequence
<220> FEATURE:
<223> OTHER INFORMATION: primer

<400> SEQUENCE: 40
gaaccggcac ctgcacac                                              18

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
tgcattgttc ccatagagtt cca                                        23

<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42
cctgaatgac cacctagagc ctt                                        23

<210> SEQ ID NO 43
<211> LENGTH: 26
<212> TYPE: DNA
<213> ORGANISM: Artificial Sequence
<220> FEATURE:
<223> OTHER INFORMATION: primer

<400> SEQUENCE: 43
catccacaga atagacctga agacaa                                     26

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
gcttggagaa cattcctgta acttg                                      25

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
tggagctgca gaggatgatt g                                          21

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
gaagttgccg tcagaaaaca tg                                         22
```

```
<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
tggctgtcat ggcttcagta                                              20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
gccacgtgat tcttccacaa                                              20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
ctggctgaat gcctacttcc                                              20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
caaccttcag cagcttccat                                              20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cctgaagcag aagaggatca                                              20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ccgcagctta cacatgttct                                              20

<210> SEQ ID NO 53
<211> LENGTH: 865
<212> TYPE: PRT
<213> ORGANISM: Homo sapiens
```

<400> SEQUENCE: 53

```
Met Ala Leu Val Leu Gly Ser Leu Leu Leu Gly Leu Cys Gly Asn
 1               5                  10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
        180                 185                 190

Leu Ala Asp Ser Asn Phe Lys Asp Leu Arg Thr Leu Leu Asn Glu Thr
    195                 200                 205

Pro Glu Gln Ile Lys Tyr Ile Leu Ala Gln Tyr Asn Thr Thr Lys Asp
210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
        260                 265                 270

Met Asn Ser Thr Leu Lys Ser Leu His Gln Gln Ser Thr Gln Leu Ser
    275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
        340                 345                 350

Leu Asp Gly Leu Val Gln Gln Gly Tyr Gln Ser Leu Asn Asp Ile Pro
    355                 360                 365

Asp Arg Val Gln Arg Gln Thr Thr Thr Val Val Ala Gly Ile Lys Arg
370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415
```

-continued

```
Glu Ser Tyr Ile His Arg Asn Leu Pro Thr Leu Glu Tyr Asp Ser
                420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
                515                 520                 525

Asp Thr Pro Tyr Leu Leu Asn Glu Asp Trp Glu Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
            610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Arg Val Leu Pro Ile
                675                 680                 685

Glu Gln Ser Leu Ser Thr Leu Tyr Gln Ser Val Lys Ile Leu Gln Arg
    690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
    755                 760                 765

Lys Pro Val Ala Thr Ala Leu Asp Thr Ala Val Asp Val Phe Leu Cys
    770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Val Glu
                820                 825                 830
```

```
Thr Ile Pro Met Lys Asn Met Glu Asn Gly Asn Gly Tyr His Lys
            835                 840                 845

Asp His Val Tyr Gly Ile His Asn Pro Val Met Thr Ser Pro Ser Gln
        850                 855                 860

His
865

<210> SEQ ID NO 54
<211> LENGTH: 161
<212> TYPE: PRT
<213> ORGANISM: Homo sapiens

<400> SEQUENCE: 54

Met Asn Leu Ala Ile Ser Ile Ala Leu Leu Leu Thr Val Leu Gln Val
  1               5                  10                  15

Ser Arg Gly Gln Lys Val Thr Ser Leu Thr Ala Cys Leu Val Asp Gln
                 20                  25                  30

Ser Leu Arg Leu Asp Cys Arg His Glu Asn Thr Ser Ser Ser Pro Ile
             35                  40                  45

Gln Tyr Glu Phe Ser Leu Thr Arg Glu Thr Lys Lys His Val Leu Phe
     50                  55                  60

Gly Thr Val Gly Val Pro Glu His Thr Tyr Arg Ser Arg Thr Asn Phe
 65                  70                  75                  80

Thr Ser Lys Tyr Asn Met Lys Val Leu Tyr Leu Ser Ala Phe Thr Ser
                 85                  90                  95

Lys Asp Glu Gly Thr Tyr Thr Cys Ala Leu His His Ser Gly His Ser
                100                 105                 110

Pro Pro Ile Ser Ser Gln Asn Val Thr Val Leu Arg Asp Lys Leu Val
            115                 120                 125

Lys Cys Glu Gly Ile Ser Leu Leu Ala Gln Asn Thr Ser Trp Leu Leu
        130                 135                 140

Leu Leu Leu Leu Ser Leu Ser Leu Leu Gln Ala Thr Asp Phe Met Ser
145                 150                 155                 160

Leu

<210> SEQ ID NO 55
<211> LENGTH: 742
<212> TYPE: PRT
<213> ORGANISM: Homo sapiens

<400> SEQUENCE: 55

Met Asp Lys Phe Trp Trp His Ala Ala Trp Gly Leu Cys Leu Val Pro
  1               5                  10                  15

Leu Ser Leu Ala Gln Ile Asp Leu Asn Ile Thr Cys Arg Phe Ala Gly
                 20                  25                  30

Val Phe His Val Glu Lys Asn Gly Arg Tyr Ser Ile Ser Arg Thr Glu
             35                  40                  45

Ala Ala Asp Leu Cys Lys Ala Phe Asn Ser Thr Leu Pro Thr Met Ala
     50                  55                  60

Gln Met Glu Lys Ala Leu Ser Ile Gly Phe Glu Thr Cys Arg Tyr Gly
 65                  70                  75                  80

Phe Ile Glu Gly His Val Val Ile Pro Arg Ile His Pro Asn Ser Ile
                 85                  90                  95

Cys Ala Ala Asn Asn Thr Gly Val Tyr Ile Leu Thr Ser Asn Thr Ser
                100                 105                 110

Gln Tyr Asp Thr Tyr Cys Phe Asn Ala Ser Ala Pro Pro Glu Glu Asp
```

-continued

```
            115                 120                 125
Cys Thr Ser Val Thr Asp Leu Pro Asn Ala Phe Asp Gly Pro Ile Thr
        130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Glu Arg Ser Ser Thr Ser Gly Gly
            180                 185                 190
Tyr Ile Phe Tyr Thr Phe Ser Thr Val His Pro Ile Pro Asp Glu Asp
                195                 200                 205
Ser Pro Trp Ile Thr Asp Ser Thr Asp Arg Ile Pro Ala Thr Thr Leu
        210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
            260                 265                 270
Ser Ala Gly Trp Glu Pro Asn Glu Glu Asn Glu Asp Glu Arg Asp Arg
        275                 280                 285
His Leu Ser Phe Ser Gly Ser Gly Ile Asp Asp Glu Asp Phe Ile
290                 295                 300
Ser Ser Thr Ile Ser Thr Thr Pro Arg Ala Phe Asp His Thr Lys Gln
305                 310                 315                 320
Asn Gln Asp Trp Thr Gln Trp Asn Pro Ser His Ser Asn Pro Glu Val
                325                 330                 335
Leu Leu Gln Thr Thr Thr Arg Met Thr Asp Val Asp Arg Asn Gly Thr
            340                 345                 350
Thr Ala Tyr Glu Gly Asn Trp Asn Pro Glu Ala His Pro Pro Leu Ile
        355                 360                 365
His His Glu His His Glu Glu Glu Thr Pro His Ser Thr Ser Thr
370                 375                 380
Ile Gln Ala Thr Pro Ser Ser Thr Thr Glu Glu Thr Ala Thr Gln Lys
385                 390                 395                 400
Glu Gln Trp Phe Gly Asn Arg Trp His Glu Gly Tyr Arg Gln Thr Pro
                405                 410                 415
Lys Glu Asp Ser His Ser Thr Thr Gly Thr Ala Ala Ala Ser Ala His
                420                 425                 430
Thr Ser His Pro Met Gln Gly Arg Thr Thr Pro Ser Pro Glu Asp Ser
        435                 440                 445
Ser Trp Thr Asp Phe Phe Asn Pro Ile Ser His Pro Met Gly Arg Gly
        450                 455                 460
His Gln Ala Gly Arg Arg Met Asp Met Asp Ser Ser His Ser Ile Thr
465                 470                 475                 480
Leu Gln Pro Thr Ala Asn Pro Asn Thr Gly Leu Val Glu Asp Leu Asp
                485                 490                 495
Arg Thr Gly Pro Leu Ser Met Thr Thr Gln Gln Ser Asn Ser Gln Ser
                500                 505                 510
Phe Ser Thr Ser His Glu Gly Leu Glu Glu Asp Lys Asp His Pro Thr
        515                 520                 525
Thr Ser Thr Leu Thr Ser Ser Asn Arg Asn Asp Val Thr Gly Gly Arg
        530                 535                 540
```

```
Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
        610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
                740

<210> SEQ ID NO 56
<211> LENGTH: 356
<212> TYPE: PRT
<213> ORGANISM: Homo sapiens

<400> SEQUENCE: 56

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
            20                  25                  30

Phe Arg Glu Glu Asn Ala Asn Phe Asn Lys Ile Phe Leu Pro Thr Ile
        35                  40                  45

Tyr Ser Ile Ile Phe Leu Thr Gly Ile Val Gly Asn Gly Leu Val Ile
    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                85                  90                  95

Phe Trp Ala Val Asp Ala Val Ala Asn Trp Tyr Phe Gly Asn Phe Leu
            100                 105                 110

Cys Lys Ala Val His Val Ile Tyr Thr Val Asn Leu Tyr Ser Ser Val
        115                 120                 125

Leu Ile Leu Ala Phe Ile Ser Leu Asp Arg Tyr Leu Ala Ile Val His
    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
```

```
                        165                 170                 175

Ile Phe Ala Asn Val Ser Glu Ala Asp Asp Arg Tyr Ile Cys Asp Arg
                180                 185                 190

Phe Tyr Pro Asn Asp Leu Trp Val Val Phe Gln Phe Gln His Ile
            195                 200                 205

Met Val Gly Leu Ile Leu Pro Gly Ile Val Ile Leu Ser Cys Tyr Cys
        210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
            260                 265                 270

Ile Ile Lys Gln Gly Cys Glu Phe Glu Asn Thr Val His Lys Trp Ile
        275                 280                 285

Ser Ile Thr Glu Ala Leu Ala Phe Phe His Cys Cys Leu Asn Pro Ile
    290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
            340                 345                 350

Phe His Ser Ser
        355

<210> SEQ ID NO 57
<211> LENGTH: 1621
<212> TYPE: PRT
<213> ORGANISM: Homo sapiens

<400> SEQUENCE: 57

Met Glu Gly Cys Met Gly Glu Glu Ser Phe Gln Met Trp Glu Leu Asn
1               5                   10                  15

Arg Arg Leu Glu Ala Tyr Leu Ala Arg Val Lys Ala Leu Glu Glu Gln
            20                  25                  30

Asn Glu Leu Leu Ser Ala Glu Leu Gly Gly Leu Arg Ala Gln Ser Ala
        35                  40                  45

Asp Thr Ser Trp Arg Ala His Ala Asp Asp Glu Leu Ala Ala Leu Arg
    50                  55                  60

Ala Leu Val Asp Gln Arg Trp Arg Glu Lys His Ala Ala Glu Val Ala
65                  70                  75                  80

Arg Asp Asn Leu Ala Glu Glu Leu Gly Val Ala Gly Arg Cys Gln
                85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
        115                 120                 125

Gln Val Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Pro Ala Pro Glu Val Glu
                165                 170                 175
```

Glu Leu Ala Arg Arg Leu Gly Glu Ala Trp Arg Gly Ala Val Arg Gly
            180                 185                 190

Tyr Gln Glu Arg Val Ala His Met Glu Thr Ser Leu Gly Gln Ala Arg
        195                 200                 205

Glu Arg Leu Gly Arg Ala Val Gln Gly Ala Arg Glu Gly Arg Leu Glu
    210                 215                 220

Leu Gln Gln Leu Gln Ala Glu Arg Gly Gly Leu Leu Glu Arg Arg Ala
225                 230                 235                 240

Ala Leu Glu Gln Arg Leu Glu Gly Arg Trp Gln Glu Arg Leu Arg Ala
                245                 250                 255

Thr Glu Lys Phe Gln Leu Ala Val Glu Ala Leu Glu Gln Glu Lys Gln
            260                 265                 270

Gly Leu Gln Ser Gln Ile Ala Gln Val Leu Glu Gly Arg Gln Gln Leu
        275                 280                 285

Ala His Leu Lys Met Ser Leu Ser Leu Glu Val Ala Thr Tyr Arg Thr
    290                 295                 300

Leu Leu Glu Ala Glu Asn Ser Arg Leu Gln Thr Pro Gly Gly Gly Ser
305                 310                 315                 320

Lys Thr Ser Leu Ser Phe Gln Asp Pro Lys Leu Glu Leu Gln Phe Pro
                325                 330                 335

Arg Thr Pro Glu Gly Arg Arg Leu Gly Ser Leu Leu Pro Val Leu Ser
            340                 345                 350

Pro Thr Ser Leu Pro Ser Pro Leu Pro Ala Thr Leu Glu Thr Pro Val
        355                 360                 365

Pro Ala Phe Leu Lys Asn Gln Glu Phe Leu Gln Ala Arg Thr Pro Thr
    370                 375                 380

Leu Ala Ser Thr Pro Ile Pro Pro Thr Pro Gln Ala Pro Ser Pro Ala
385                 390                 395                 400

Val Asp Ala Glu Ile Arg Ala Gln Asp Ala Pro Leu Ser Leu Leu Gln
                405                 410                 415

Thr Gln Gly Gly Arg Lys Gln Ala Pro Glu Pro Leu Arg Ala Glu Ala
            420                 425                 430

Arg Val Ala Ile Pro Ala Ser Val Leu Pro Gly Pro Glu Glu Pro Gly
        435                 440                 445

Gly Gln Arg Gln Glu Ala Ser Thr Gly Gln Ser Pro Glu Asp His Ala
    450                 455                 460

Ser Leu Ala Pro Pro Leu Ser Pro Asp His Ser Ser Leu Glu Ala Lys
465                 470                 475                 480

Asp Gly Glu Ser Gly Gly Ser Arg Val Phe Ser Ile Cys Arg Gly Glu
                485                 490                 495

Gly Glu Gly Gln Ile Trp Gly Leu Val Glu Lys Glu Thr Ala Ile Glu
            500                 505                 510

Gly Lys Val Val Ser Ser Leu Gln Gln Glu Ile Trp Glu Glu Glu Asp
        515                 520                 525

Leu Asn Arg Lys Glu Ile Gln Asp Ser Gln Val Pro Leu Glu Lys Glu
    530                 535                 540

Thr Leu Lys Ser Leu Gly Glu Glu Ile Gln Glu Ser Leu Lys Thr Leu
545                 550                 555                 560

Glu Asn Gln Ser His Glu Thr Leu Glu Arg Glu Asn Gln Glu Cys Pro
                565                 570                 575

Arg Ser Leu Glu Glu Asp Leu Glu Thr Leu Lys Ser Leu Glu Lys Glu
            580                 585                 590

Asn Lys Glu Leu Leu Lys Asp Val Glu Val Val Arg Pro Leu Glu Lys

-continued

```
                595                 600                 605
Glu Ala Val Gly Gln Leu Lys Pro Thr Gly Lys Glu Asp Thr Gln Thr
610                 615                 620
Leu Gln Ser Leu Gln Lys Glu Asn Gln Glu Leu Met Lys Ser Leu Glu
625                 630                 635                 640
Gly Asn Leu Glu Thr Phe Leu Phe Pro Gly Thr Glu Asn Gln Glu Leu
                645                 650                 655
Val Ser Ser Leu Gln Glu Asn Leu Glu Ser Leu Thr Ala Leu Glu Lys
                660                 665                 670
Glu Asn Gln Glu Pro Leu Arg Ser Pro Glu Val Gly Asp Glu Glu Ala
                675                 680                 685
Leu Arg Pro Leu Thr Lys Glu Asn Gln Glu Pro Leu Arg Ser Leu Glu
690                 695                 700
Asp Glu Asn Lys Glu Ala Phe Arg Ser Leu Glu Lys Glu Asn Gln Glu
705                 710                 715                 720
Pro Leu Lys Thr Leu Glu Glu Asp Gln Ser Ile Val Arg Pro Leu
                725                 730                 735
Glu Thr Glu Asn His Lys Ser Leu Arg Ser Leu Glu Glu Gln Asp Gln
                740                 745                 750
Glu Thr Leu Arg Thr Leu Glu Lys Glu Thr Gln Gln Arg Arg Arg Ser
                755                 760                 765
Leu Gly Glu Gln Asp Gln Met Thr Leu Arg Pro Pro Glu Lys Val Asp
770                 775                 780
Leu Glu Pro Leu Lys Ser Leu Asp Gln Glu Ile Ala Arg Pro Leu Glu
785                 790                 795                 800
Asn Glu Asn Gln Glu Phe Leu Lys Ser Leu Lys Glu Ser Val Glu
                805                 810                 815
Ala Val Lys Ser Leu Glu Thr Glu Ile Leu Glu Ser Leu Lys Ser Ala
                820                 825                 830
Gly Gln Glu Asn Leu Glu Thr Leu Lys Ser Pro Glu Thr Gln Ala Pro
                835                 840                 845
Leu Trp Thr Pro Glu Glu Ile Asn Gln Gly Ala Met Asn Pro Leu Glu
850                 855                 860
Lys Glu Ile Gln Glu Pro Leu Glu Ser Val Glu Val Asn Gln Glu Thr
865                 870                 875                 880
Phe Arg Leu Leu Glu Glu Asn Gln Glu Ser Leu Arg Ser Leu Gly
                885                 890                 895
Ala Trp Asn Leu Glu Asn Leu Arg Ser Pro Glu Glu Val Asp Lys Glu
                900                 905                 910
Ser Gln Arg Asn Leu Glu Glu Glu Asn Leu Gly Lys Gly Glu Tyr
                915                 920                 925
Gln Glu Ser Leu Arg Ser Leu Glu Glu Glu Gly Gln Glu Leu Pro Gln
                930                 935                 940
Ser Ala Asp Val Gln Arg Trp Glu Asp Thr Val Glu Lys Asp Gln Glu
945                 950                 955                 960
Leu Ala Gln Glu Ser Pro Pro Gly Met Ala Gly Val Glu Asn Glu Asp
                965                 970                 975
Glu Ala Glu Leu Asn Leu Arg Glu Gln Asp Gly Phe Thr Gly Lys Glu
                980                 985                 990
Glu Val Val Glu Gln Gly Glu Leu Asn Ala Thr Glu Glu Val Trp Ile
                995                 1000                1005
Pro Gly Glu Gly His Pro Glu Ser Pro Glu Pro Lys Glu Gln Arg Gly
                1010                1015                1020
```

```
Leu Val Glu Gly Ala Ser Val Lys Gly Gly Ala Glu Leu Gln Asp
1025                1030                1035                1040

Pro Glu Gly Gln Ser Gln Gln Val Gly Ala Pro Gly Leu Gln Ala Pro
                1045                1050                1055

Gln Gly Leu Pro Glu Ala Ile Glu Pro Leu Val Glu Asp Asp Val Ala
                1060                1065                1070

Pro Gly Gly Asp Gln Ala Ser Pro Glu Val Met Leu Gly Ser Glu Pro
                1075                1080                1085

Ala Met Gly Glu Ser Ala Ala Gly Ala Glu Pro Gly Pro Gly Gln Gly
                1090                1095                1100

Val Gly Gly Leu Gly Asp Pro Gly His Leu Thr Arg Glu Glu Val Met
1105                1110                1115                1120

Glu Pro Pro Leu Glu Glu Glu Ser Leu Glu Ala Lys Arg Val Gln Gly
                1125                1130                1135

Leu Glu Gly Pro Arg Lys Asp Leu Glu Glu Ala Gly Gly Leu Gly Thr
                1140                1145                1150

Glu Phe Ser Glu Leu Pro Gly Lys Ser Arg Asp Pro Trp Glu Pro Pro
                1155                1160                1165

Arg Glu Gly Arg Glu Glu Ser Glu Ala Glu Ala Pro Arg Gly Ala Glu
                1170                1175                1180

Glu Ala Phe Pro Ala Glu Thr Leu Gly His Thr Gly Ser Asp Ala Pro
1185                1190                1195                1200

Ser Pro Trp Pro Leu Gly Ser Glu Glu Ala Glu Glu Asp Val Pro Pro
                1205                1210                1215

Val Leu Val Ser Pro Ser Pro Thr Tyr Thr Pro Ile Leu Glu Asp Ala
                1220                1225                1230

Pro Gly Pro Gln Pro Gln Ala Glu Gly Ser Gln Glu Ala Ser Trp Gly
                1235                1240                1245

Val Gln Gly Arg Ala Glu Ala Leu Gly Lys Val Glu Ser Glu Gln Glu
                1250                1255                1260

Glu Leu Gly Ser Gly Glu Ile Pro Glu Gly Pro Gln Glu Glu Gly Glu
1265                1270                1275                1280

Glu Ser Arg Glu Glu Ser Glu Glu Asp Glu Leu Gly Glu Thr Leu Pro
                1285                1290                1295

Asp Ser Thr Pro Leu Gly Phe Tyr Leu Arg Ser Pro Thr Ser Pro Arg
                1300                1305                1310

Trp Asp Pro Thr Gly Glu Gln Arg Pro Pro Gln Gly Glu Thr Gly
                1315                1320                1325

Lys Glu Gly Trp Asp Pro Ala Val Leu Ala Ser Glu Gly Leu Glu Ala
                1330                1335                1340

Pro Pro Ser Glu Lys Glu Glu Gly Glu Gly Glu Glu Glu Cys Gly
1345                1350                1355                1360

Arg Asp Ser Asp Leu Ser Glu Glu Phe Glu Asp Leu Gly Thr Glu Ala
                1365                1370                1375

Pro Phe Leu Pro Gly Val Pro Gly Glu Val Ala Glu Pro Leu Gly Gln
                1380                1385                1390

Val Pro Gln Leu Leu Leu Asp Pro Ala Ala Trp Asp Arg Asp Gly Glu
                1395                1400                1405

Ser Asp Gly Phe Ala Asp Glu Glu Glu Ser Gly Glu Glu Gly Glu Glu
                1410                1415                1420

Asp Gln Glu Glu Gly Arg Glu Pro Gly Ala Gly Arg Trp Gly Pro Gly
1425                1430                1435                1440
```

```
Ser Ser Val Gly Ser Leu Gln Ala Leu Ser Ser Gln Arg Gly Glu
        1445                1450                1455

Phe Leu Glu Ser Asp Ser Val Val Ser Val Pro Trp Asp Asp Ser
        1460                1465                1470

Leu Arg Gly Ala Val Ala Gly Ala Pro Lys Thr Ala Leu Glu Thr Glu
        1475                1480                1485

Ser Gln Asp Ser Ala Glu Pro Ser Gly Ser Glu Glu Ser Asp Pro
        1490                1495                1500

Val Ser Leu Glu Arg Glu Asp Lys Val Pro Gly Pro Leu Glu Ile Pro
1505            1510                1515                1520

Ser Gly Met Glu Asp Ala Gly Pro Gly Ala Asp Ile Ile Gly Val Asn
        1525                1530                1535

Gly Gln Gly Pro Asn Leu Glu Gly Lys Ser Gln His Val Asn Gly Gly
        1540                1545                1550

Val Met Asn Gly Leu Glu Gln Ser Glu Val Gly Gln Gly Met Pro
        1555                1560                1565

Leu Val Ser Glu Gly Asp Arg Gly Ser Pro Phe Gln Gly Glu Glu Gly
        1570                1575                1580

Ser Ala Leu Lys Thr Ser Trp Ala Gly Ala Pro Val His Leu Gly Gln
1585            1590                1595                1600

Gly Gln Phe Leu Lys Phe Thr Gln Arg Glu Gly Asp Arg Glu Ser Trp
        1605                1610                1615

Ser Ser Gly Glu Asp
        1620

<210> SEQ ID NO 58
<211> LENGTH: 362
<212> TYPE: PRT
<213> ORGANISM: Homo sapiens

<400> SEQUENCE: 58

Met Glu Thr Asp Ala Pro Gln Pro Gly Leu Ala Ser Pro Asp Ser Pro
1               5                   10                  15

His Asp Pro Cys Lys Met Phe Ile Gly Gly Leu Ser Trp Gln Thr Thr
                20                  25                  30

Gln Glu Gly Leu Arg Glu Tyr Phe Gly Gln Phe Gly Glu Val Lys Glu
            35                  40                  45

Cys Leu Val Met Arg Asp Pro Leu Thr Lys Arg Ser Arg Gly Phe Gly
        50                  55                  60

Phe Val Thr Phe Met Asp Gln Ala Gly Val Asp Lys Val Leu Ala Gln
65                  70                  75                  80

Ser Arg His Glu Leu Asp Ser Lys Thr Ile Asp Pro Lys Val Ala Phe
                85                  90                  95

Pro Arg Arg Ala Gln Pro Lys Met Val Thr Arg Thr Lys Lys Ile Phe
            100                 105                 110

Val Gly Gly Leu Ser Val Asn Thr Thr Val Glu Asp Val Lys Gln Tyr
        115                 120                 125

Phe Glu Gln Phe Gly Lys Val Asp Asp Ala Met Leu Met Phe Asp Lys
130                 135                 140

Thr Thr Asn Arg His Arg Gly Phe Gly Phe Val Thr Phe Glu Ser Glu
145                 150                 155                 160

Asp Ile Val Glu Lys Val Cys Glu Ile His Phe His Glu Ile Asn Asn
                165                 170                 175

Lys Met Val Glu Cys Lys Lys Ala Gln Pro Lys Glu Val Met Ser Pro
            180                 185                 190
```

```
Thr Gly Ser Ala Arg Gly Arg Ser Arg Val Met Pro Tyr Gly Met Asp
            195                 200                 205
Ala Phe Met Leu Gly Ile Gly Met Leu Gly Tyr Pro Gly Phe Gln Ala
210                 215                 220
Thr Thr Tyr Ala Ser Arg Ser Tyr Thr Gly Leu Ala Pro Gly Tyr Thr
225                 230                 235                 240
Tyr Gln Phe Pro Glu Phe Arg Val Glu Arg Thr Pro Leu Pro Ser Ala
                245                 250                 255
Pro Val Leu Pro Glu Leu Thr Ala Ile Pro Leu Thr Ala Tyr Gly Pro
                260                 265                 270
Met Ala Ala Ala Ala Ala Ala Val Val Arg Gly Thr Gly Ser
            275                 280                 285
His Pro Trp Thr Met Ala Pro Pro Gly Ser Thr Pro Ser Arg Thr
            290                 295                 300
Gly Gly Phe Leu Gly Thr Thr Ser Pro Gly Pro Met Ala Glu Leu Tyr
305                 310                 315                 320
Gly Ala Ala Asn Gln Asp Ser Gly Val Ser Ser Tyr Ile Ser Ala Ala
                325                 330                 335
Ser Pro Ala Pro Ser Thr Gly Phe Gly His Ser Leu Gly Gly Pro Leu
            340                 345                 350
Ile Ala Thr Ala Phe Thr Asn Gly Tyr His
            355                 360
```

<210> SEQ ID NO 59
<211> LENGTH: 651
<212> TYPE: PRT
<213> ORGANISM: Homo sapiens

<400> SEQUENCE: 59

```
Met Lys Asp Tyr Asp Glu Leu Leu Lys Tyr Tyr Glu Leu His Glu Thr
1               5                   10                  15
Ile Gly Thr Gly Gly Phe Ala Lys Val Lys Leu Ala Cys His Ile Leu
            20                  25                  30
Thr Gly Glu Met Val Ala Ile Lys Ile Met Asp Lys Asn Thr Leu Gly
            35                  40                  45
Ser Asp Leu Pro Arg Ile Lys Thr Glu Ile Glu Ala Leu Lys Asn Leu
50                  55                  60
Arg His Gln His Ile Cys Gln Leu Tyr His Val Leu Glu Thr Ala Asn
65                  70                  75                  80
Lys Ile Phe Met Val Leu Glu Tyr Cys Pro Gly Gly Glu Leu Phe Asp
                85                  90                  95
Tyr Ile Ile Ser Gln Asp Arg Leu Ser Glu Glu Glu Thr Arg Val Val
                100                 105                 110
Phe Arg Gln Ile Val Ser Ala Val Ala Tyr Val His Ser Gln Gly Tyr
            115                 120                 125
Ala His Arg Asp Leu Lys Pro Glu Asn Leu Leu Phe Asp Glu Tyr His
            130                 135                 140
Lys Leu Lys Leu Ile Asp Phe Gly Leu Cys Ala Lys Pro Lys Gly Asn
145                 150                 155                 160
Lys Asp Tyr His Leu Gln Thr Cys Cys Gly Ser Leu Ala Tyr Ala Ala
                165                 170                 175
Pro Glu Leu Ile Gln Gly Lys Ser Tyr Leu Gly Ser Glu Ala Asp Val
                180                 185                 190
Trp Ser Met Gly Ile Leu Leu Tyr Val Leu Met Cys Gly Phe Leu Pro
```

-continued

```
            195                 200                 205
Phe Asp Asp Asn Val Met Ala Leu Tyr Lys Lys Ile Met Arg Gly
210                 215                 220
Lys Tyr Asp Val Pro Lys Trp Leu Ser Pro Ser Ile Leu Leu Leu
225                 230                 235                 240
Gln Gln Met Leu Gln Val Asp Pro Lys Lys Arg Ile Ser Met Lys Asn
                245                 250                 255
Leu Leu Asn His Pro Trp Ile Met Gln Asp Tyr Asn Tyr Pro Val Glu
            260                 265                 270
Trp Gln Ser Lys Asn Pro Phe Ile His Leu Asp Asp Cys Val Thr
            275                 280                 285
Glu Leu Ser Val His His Arg Asn Asn Arg Gln Thr Met Glu Asp Leu
290                 295                 300
Ile Ser Leu Trp Gln Tyr Asp His Leu Thr Ala Thr Tyr Leu Leu Leu
305                 310                 315                 320
Leu Ala Lys Lys Ala Arg Gly Lys Pro Val Arg Leu Arg Leu Ser Ser
                325                 330                 335
Phe Ser Cys Gly Gln Ala Ser Ala Thr Pro Phe Thr Asp Ile Lys Ser
            340                 345                 350
Asn Asn Trp Ser Leu Glu Asp Val Thr Ala Ser Asp Lys Asn Tyr Val
            355                 360                 365
Ala Gly Leu Ile Asp Tyr Asp Trp Cys Glu Asp Leu Ser Thr Gly
370                 375                 380
Ala Ala Thr Pro Arg Thr Ser Gln Phe Thr Lys Tyr Trp Thr Glu Ser
385                 390                 395                 400
Asn Gly Val Glu Ser Lys Ser Leu Thr Pro Ala Leu Cys Arg Thr Pro
                405                 410                 415
Ala Asn Lys Leu Lys Asn Lys Glu Asn Val Tyr Thr Pro Lys Ser Ala
            420                 425                 430
Val Lys Asn Glu Glu Tyr Phe Met Phe Pro Glu Pro Lys Thr Pro Val
            435                 440                 445
Asn Lys Asn Gln His Lys Arg Glu Ile Leu Thr Thr Pro Asn Arg Tyr
            450                 455                 460
Thr Thr Pro Ser Lys Ala Arg Asn Gln Cys Leu Lys Glu Thr Pro Ile
465                 470                 475                 480
Lys Ile Pro Val Asn Ser Thr Gly Thr Asp Lys Leu Met Thr Gly Val
                485                 490                 495
Ile Ser Pro Glu Arg Arg Cys Arg Ser Val Glu Leu Asp Leu Asn Gln
            500                 505                 510
Ala His Met Glu Glu Thr Pro Lys Arg Lys Gly Ala Lys Val Phe Gly
            515                 520                 525
Ser Leu Glu Arg Gly Leu Asp Lys Val Ile Thr Val Leu Thr Arg Ser
            530                 535                 540
Lys Arg Lys Gly Ser Ala Arg Asp Gly Pro Arg Arg Leu Lys Leu His
545                 550                 555                 560
Tyr Asn Val Thr Thr Thr Arg Leu Val Asn Pro Asp Gln Leu Leu Asn
                565                 570                 575
Glu Ile Met Ser Ile Leu Pro Lys Lys His Val Asp Phe Val Gln Lys
            580                 585                 590
Gly Tyr Thr Leu Lys Cys Gln Thr Gln Ser Asp Phe Gly Lys Val Thr
            595                 600                 605
Met Gln Phe Glu Leu Glu Val Cys Gln Leu Gln Lys Pro Asp Val Val
610                 615                 620
```

```
Gly Ile Arg Arg Gln Arg Leu Lys Gly Asp Ala Trp Val Tyr Lys Arg
625                 630                 635                 640

Leu Val Glu Asp Ile Leu Ser Ser Cys Lys Val
            645                 650

<210> SEQ ID NO 60
<211> LENGTH: 1106
<212> TYPE: PRT
<213> ORGANISM: Homo sapiens

<400> SEQUENCE: 60

Met Phe Asn Ser Met Thr Pro Pro Ile Ser Ser Tyr Gly Glu Pro
  1               5                  10                  15

Cys Cys Leu Arg Pro Leu Pro Ser Gln Gly Ala Pro Ser Val Gly Thr
                 20                  25                  30

Glu Gly Leu Ser Gly Pro Pro Phe Cys His Gln Ala Asn Leu Met Ser
                35                  40                  45

Gly Pro His Ser Tyr Gly Pro Ala Arg Glu Thr Asn Ser Cys Thr Glu
 50                  55                  60

Gly Pro Leu Phe Ser Ser Pro Arg Ser Ala Val Lys Leu Thr Lys Lys
 65                  70                  75                  80

Arg Ala Leu Ser Ile Ser Pro Leu Ser Asp Ala Ser Leu Asp Leu Gln
                 85                  90                  95

Thr Val Ile Arg Thr Ser Pro Ser Ser Leu Val Ala Phe Ile Asn Ser
                100                 105                 110

Arg Cys Thr Ser Pro Gly Gly Ser Tyr Gly His Leu Ser Ile Gly Thr
                115                 120                 125

Met Ser Pro Ser Leu Gly Phe Pro Ala Gln Met Asn His Gln Lys Gly
130                 135                 140

Pro Ser Pro Ser Phe Gly Val Gln Pro Cys Gly Pro His Asp Ser Ala
145                 150                 155                 160

Arg Gly Gly Met Ile Pro His Pro Gln Ser Arg Gly Pro Phe Pro Thr
                165                 170                 175

Cys Gln Leu Lys Ser Glu Leu Asp Met Leu Val Gly Lys Cys Arg Glu
                180                 185                 190

Glu Pro Leu Glu Gly Asp Met Ser Ser Pro Asn Ser Thr Gly Ile Gln
                195                 200                 205

Asp Pro Leu Leu Gly Met Leu Asp Gly Arg Glu Asp Leu Glu Arg Glu
                210                 215                 220

Glu Lys Arg Glu Pro Glu Ser Val Tyr Glu Thr Asp Cys Arg Trp Asp
225                 230                 235                 240

Gly Cys Ser Gln Glu Phe Asp Ser Gln Glu Gln Leu Val His His Ile
                245                 250                 255

Asn Ser Glu His Ile His Gly Glu Arg Lys Glu Phe Val Cys His Trp
                260                 265                 270

Gly Gly Cys Ser Arg Glu Leu Arg Pro Phe Lys Ala Gln Tyr Met Leu
                275                 280                 285

Val Val His Met Arg Arg His Thr Gly Glu Lys Pro His Lys Cys Thr
290                 295                 300

Phe Glu Gly Cys Arg Lys Ser Tyr Ser Arg Leu Glu Asn Leu Lys Thr
305                 310                 315                 320

His Leu Arg Ser His Thr Gly Glu Lys Pro Tyr Met Cys Glu His Glu
                325                 330                 335

Gly Cys Ser Lys Ala Phe Ser Asn Ala Ser Asp Arg Ala Lys His Gln
```

```
              340                 345                 350
Asn Arg Thr His Ser Asn Glu Lys Pro Tyr Val Cys Lys Leu Pro Gly
            355                 360                 365
Cys Thr Lys Arg Tyr Thr Asp Pro Ser Ser Leu Arg Lys His Val Lys
            370                 375                 380
Thr Val His Gly Pro Asp Ala His Val Thr Lys Arg His Arg Gly Asp
385                 390                 395                 400
Gly Pro Leu Pro Arg Ala Pro Ser Ile Ser Thr Val Glu Pro Lys Arg
                405                 410                 415
Glu Arg Glu Gly Gly Pro Ile Arg Glu Ser Arg Leu Thr Val Pro
                420                 425                 430
Glu Gly Ala Met Lys Pro Gln Pro Ser Pro Gly Ala Gln Ser Ser Cys
            435                 440                 445
Ser Ser Asp His Ser Pro Ala Gly Ser Ala Ala Asn Thr Asp Ser Gly
            450                 455                 460
Val Glu Met Thr Gly Asn Ala Gly Gly Ser Thr Glu Asp Leu Ser Ser
465                 470                 475                 480
Leu Asp Glu Gly Pro Cys Ile Ala Gly Thr Gly Leu Ser Thr Leu Arg
                485                 490                 495
Arg Leu Glu Asn Leu Arg Leu Asp Gln Leu His Gln Leu Arg Pro Ile
                500                 505                 510
Gly Thr Arg Gly Leu Lys Leu Pro Ser Leu Ser His Thr Gly Thr Thr
            515                 520                 525
Val Ser Arg Arg Val Gly Pro Pro Val Ser Leu Glu Arg Arg Ser Ser
            530                 535                 540
Ser Ser Ser Ser Ile Ser Ser Ala Tyr Thr Val Ser Arg Arg Ser Ser
545                 550                 555                 560
Leu Ala Ser Pro Phe Pro Pro Gly Ser Pro Pro Glu Asn Gly Ala Ser
                565                 570                 575
Ser Leu Pro Gly Leu Met Pro Ala Gln His Tyr Leu Leu Arg Ala Arg
            580                 585                 590
Tyr Ala Ser Ala Arg Gly Gly Gly Thr Ser Pro Thr Ala Ala Ser Ser
            595                 600                 605
Leu Asp Arg Ile Gly Gly Leu Pro Met Pro Pro Trp Arg Ser Arg Ala
            610                 615                 620
Glu Tyr Pro Gly Tyr Asn Pro Asn Ala Gly Val Thr Arg Arg Ala Ser
625                 630                 635                 640
Asp Pro Ala Gln Ala Ala Asp Arg Pro Ala Pro Ala Arg Val Gln Arg
                645                 650                 655
Phe Lys Ser Leu Gly Cys Val His Thr Pro Thr Val Ala Gly Gly
                660                 665                 670
Gly Gln Asn Phe Asp Pro Tyr Leu Pro Thr Ser Val Tyr Ser Pro Gln
            675                 680                 685
Pro Pro Ser Ile Thr Glu Asn Ala Ala Met Asp Ala Arg Gly Leu Gln
            690                 695                 700
Glu Glu Pro Glu Val Gly Thr Ser Met Val Gly Ser Gly Leu Asn Pro
705                 710                 715                 720
Tyr Met Asp Phe Pro Pro Thr Asp Thr Leu Gly Tyr Gly Gly Pro Glu
                725                 730                 735
Gly Ala Ala Ala Glu Pro Tyr Gly Ala Arg Gly Pro Gly Ser Leu Pro
            740                 745                 750
Leu Gly Pro Gly Pro Pro Thr Asn Tyr Gly Pro Asn Pro Cys Pro Gln
            755                 760                 765
```

Gln Ala Ser Tyr Pro Asp Pro Thr Gln Glu Thr Trp Gly Glu Phe Pro
    770                 775                 780

Ser His Ser Gly Leu Tyr Pro Gly Pro Lys Ala Leu Gly Gly Thr Tyr
785                 790                 795                 800

Ser Gln Cys Pro Arg Leu Glu His Tyr Gly Gln Val Gln Val Lys Pro
                805                 810                 815

Glu Gln Gly Cys Pro Val Gly Ser Asp Ser Thr Gly Leu Ala Pro Cys
            820                 825                 830

Leu Asn Ala His Pro Ser Glu Gly Pro Pro His Pro Gln Pro Leu Phe
        835                 840                 845

Ser His Tyr Pro Gln Pro Ser Pro Pro Gln Tyr Leu Gln Ser Gly Pro
    850                 855                 860

Tyr Thr Gln Pro Pro Pro Asp Tyr Leu Pro Ser Glu Pro Arg Pro Cys
865                 870                 875                 880

Leu Asp Phe Asp Ser Pro Thr His Ser Thr Gly Gln Leu Lys Ala Gln
                885                 890                 895

Leu Val Cys Asn Tyr Val Gln Ser Gln Gln Glu Leu Leu Trp Glu Gly
            900                 905                 910

Gly Gly Arg Glu Asp Ala Pro Ala Gln Glu Pro Ser Tyr Gln Ser Pro
        915                 920                 925

Lys Phe Leu Gly Gly Ser Gln Val Ser Pro Ser Arg Ala Lys Ala Pro
    930                 935                 940

Val Asn Thr Tyr Gly Pro Gly Phe Gly Pro Asn Leu Pro Asn His Lys
945                 950                 955                 960

Ser Gly Ser Tyr Pro Thr Pro Ser Pro Cys His Glu Asn Phe Val Val
                965                 970                 975

Gly Ala Asn Arg Ala Ser His Arg Ala Ala Pro Pro Arg Leu Leu
            980                 985                 990

Pro Pro Leu Pro Thr Cys Tyr Gly Pro Leu Lys Val Gly Gly Thr Asn
        995                 1000                1005

Pro Ser Cys Gly His Pro Glu Val Gly Arg Leu Gly Gly Gly Pro Ala
    1010                1015                1020

Leu Tyr Pro Pro Glu Gly Gln Val Cys Asn Pro Leu Asp Ser Leu
1025                1030                1035                1040

Asp Leu Asp Asn Thr Gln Leu Asp Phe Val Ala Ile Leu Asp Glu Pro
                1045                1050                1055

Gln Gly Leu Ser Pro Pro Ser His Asp Gln Arg Gly Ser Ser Gly
            1060                1065                1070

His Thr Pro Pro Pro Ser Gly Pro Pro Asn Met Ala Val Gly Asn Met
        1075                1080                1085

Ser Val Leu Leu Arg Ser Leu Pro Gly Glu Thr Glu Phe Leu Asn Ser
    1090                1095                1100

Ser Ala
1105

<210> SEQ ID NO 61
<211> LENGTH: 1447
<212> TYPE: PRT
<213> ORGANISM: Homo sapiens

<400> SEQUENCE: 61

Met Ala Ser Ala Gly Asn Ala Ala Glu Pro Gln Asp Arg Gly Gly Gly
1               5                   10                  15

Gly Ser Gly Cys Ile Gly Ala Pro Gly Arg Pro Ala Gly Gly Gly Arg

-continued

```
                20                  25                  30
Arg Arg Arg Thr Gly Gly Leu Arg Ala Ala Pro Asp Arg Asp
            35                  40                  45
Tyr Leu His Arg Pro Ser Tyr Cys Asp Ala Ala Phe Ala Leu Glu Gln
50                  55                  60
Ile Ser Lys Gly Lys Ala Thr Gly Arg Lys Ala Pro Leu Trp Leu Arg
65                  70                  75                  80
Ala Lys Phe Gln Arg Leu Leu Phe Lys Leu Gly Cys Tyr Ile Gln Lys
            85                  90                  95
Asn Cys Gly Lys Phe Leu Val Val Gly Leu Leu Ile Phe Gly Ala Phe
            100                 105                 110
Ala Val Gly Leu Lys Ala Ala Asn Leu Glu Thr Asn Val Glu Glu Leu
            115                 120                 125
Trp Val Glu Val Gly Gly Arg Val Ser Arg Glu Leu Asn Tyr Thr Arg
            130                 135                 140
Gln Lys Ile Gly Glu Glu Ala Met Phe Asn Pro Gln Leu Met Ile Gln
145                 150                 155                 160
Thr Pro Lys Glu Glu Gly Ala Asn Val Leu Thr Thr Glu Ala Leu Leu
            165                 170                 175
Gln His Leu Asp Ser Ala Leu Gln Ala Ser Arg Val His Val Tyr Met
            180                 185                 190
Tyr Asn Arg Gln Trp Lys Leu Glu His Leu Cys Tyr Lys Ser Gly Glu
            195                 200                 205
Leu Ile Thr Glu Thr Gly Tyr Met Asp Gln Ile Ile Glu Tyr Leu Tyr
            210                 215                 220
Pro Cys Leu Ile Ile Thr Pro Leu Asp Cys Phe Trp Glu Gly Ala Lys
225                 230                 235                 240
Leu Gln Ser Gly Thr Ala Tyr Leu Leu Gly Lys Pro Pro Leu Arg Trp
            245                 250                 255
Thr Asn Phe Asp Pro Leu Glu Phe Leu Glu Glu Leu Lys Lys Ile Asn
            260                 265                 270
Tyr Gln Val Asp Ser Trp Glu Glu Met Leu Asn Lys Ala Glu Val Gly
            275                 280                 285
His Gly Tyr Met Asp Arg Pro Cys Leu Asn Pro Ala Asp Pro Asp Cys
            290                 295                 300
Pro Ala Thr Ala Pro Asn Lys Asn Ser Thr Lys Pro Leu Asp Met Ala
305                 310                 315                 320
Leu Val Leu Asn Gly Gly Cys His Gly Leu Ser Arg Lys Tyr Met His
            325                 330                 335
Trp Gln Glu Glu Leu Ile Val Gly Gly Thr Val Lys Asn Ser Thr Gly
            340                 345                 350
Lys Leu Val Ser Ala His Ala Leu Gln Thr Met Phe Gln Leu Met Thr
            355                 360                 365
Pro Lys Gln Met Tyr Glu His Phe Lys Gly Tyr Glu Tyr Val Ser His
            370                 375                 380
Ile Asn Trp Asn Glu Asp Lys Ala Ala Ala Ile Leu Glu Ala Trp Gln
385                 390                 395                 400
Arg Thr Tyr Val Glu Val Val His Gln Ser Val Ala Gln Asn Ser Thr
            405                 410                 415
Gln Lys Val Leu Ser Phe Thr Thr Thr Thr Leu Asp Asp Ile Leu Lys
            420                 425                 430
Ser Phe Ser Asp Val Ser Val Ile Arg Val Ala Ser Gly Tyr Leu Leu
            435                 440                 445
```

```
Met Leu Ala Tyr Ala Cys Leu Thr Met Leu Arg Trp Asp Cys Ser Lys
    450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                    485                 490                 495

Ala Ala Thr Thr Gln Val Leu Pro Phe Leu Ala Leu Gly Val Gly Val
                500                 505                 510

Asp Asp Val Phe Leu Leu Ala His Ala Phe Ser Glu Thr Gly Gln Asn
            515                 520                 525

Lys Arg Ile Pro Phe Glu Asp Arg Thr Gly Glu Cys Leu Lys Arg Thr
        530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Phe Ala Met Val Leu Leu Ile Phe
                580                 585                 590

Pro Ala Ile Leu Ser Met Asp Leu Tyr Arg Arg Glu Asp Arg Arg Leu
            595                 600                 605

Asp Ile Phe Cys Cys Phe Thr Ser Pro Cys Val Ser Arg Val Ile Gln
        610                 615                 620

Val Glu Pro Gln Ala Tyr Thr Asp Thr His Asp Asn Thr Arg Tyr Ser
625                 630                 635                 640

Pro Pro Pro Pro Tyr Ser Ser His Ser Phe Ala His Glu Thr Gln Ile
                    645                 650                 655

Thr Met Gln Ser Thr Val Gln Leu Arg Thr Glu Tyr Asp Pro His Thr
                660                 665                 670

His Val Tyr Tyr Thr Thr Ala Glu Pro Arg Ser Glu Ile Ser Val Gln
            675                 680                 685

Pro Val Thr Val Thr Gln Asp Thr Leu Ser Cys Gln Ser Pro Glu Ser
        690                 695                 700

Thr Ser Ser Thr Arg Asp Leu Leu Ser Gln Phe Ser Asp Ser Ser Leu
705                 710                 715                 720

His Cys Leu Glu Pro Pro Cys Thr Lys Trp Thr Leu Ser Ser Phe Ala
                725                 730                 735

Glu Lys His Tyr Ala Pro Phe Leu Leu Lys Pro Lys Ala Lys Val Val
                740                 745                 750

Val Ile Phe Leu Phe Leu Gly Leu Leu Gly Val Ser Leu Tyr Gly Thr
            755                 760                 765

Thr Arg Val Arg Asp Gly Leu Asp Leu Thr Asp Ile Val Pro Arg Glu
        770                 775                 780

Thr Arg Glu Tyr Asp Phe Ile Ala Ala Gln Phe Lys Tyr Phe Ser Phe
785                 790                 795                 800

Tyr Asn Met Tyr Ile Val Thr Gln Lys Ala Asp Tyr Pro Asn Ile Gln
                805                 810                 815

His Leu Leu Tyr Asp Leu His Arg Ser Phe Ser Asn Val Lys Tyr Val
                820                 825                 830

Met Leu Glu Glu Asn Lys Gln Leu Pro Lys Met Trp Leu His Tyr Phe
            835                 840                 845

Arg Asp Trp Leu Gln Gly Leu Gln Asp Ala Phe Asp Ser Asp Trp Glu
        850                 855                 860
```

-continued

```
Thr Gly Lys Ile Met Pro Asn Asn Tyr Lys Asn Gly Ser Asp Asp Gly
865                 870                 875                 880

Val Leu Ala Tyr Lys Leu Leu Val Gln Thr Gly Ser Arg Asp Lys Pro
                885                 890                 895

Ile Asp Ile Ser Gln Leu Thr Lys Gln Arg Leu Val Asp Ala Asp Gly
            900                 905                 910

Ile Ile Asn Pro Ser Ala Phe Tyr Ile Tyr Leu Thr Ala Trp Val Ser
            915                 920                 925

Asn Asp Pro Val Ala Tyr Ala Ser Gln Ala Asn Ile Arg Pro His
    930                 935                 940

Arg Pro Glu Trp Val His Asp Lys Ala Asp Tyr Met Pro Glu Thr Arg
945                 950                 955                 960

Leu Arg Ile Pro Ala Ala Glu Pro Ile Glu Tyr Ala Gln Phe Pro Phe
                965                 970                 975

Tyr Leu Asn Gly Leu Arg Asp Thr Ser Asp Phe Val Glu Ala Ile Glu
                980                 985                 990

Lys Val Arg Thr Ile Cys Ser Asn Tyr Thr Ser Leu Gly Leu Ser Ser
                995                 1000                1005

Tyr Pro Asn Gly Tyr Pro Phe Leu Phe Trp Glu Gln Tyr Ile Gly Leu
    1010                1015                1020

Arg His Trp Leu Leu Leu Phe Ile Ser Val Val Leu Ala Cys Thr Phe
1025                1030                1035                1040

Leu Val Cys Ala Val Phe Leu Leu Asn Pro Trp Thr Ala Gly Ile Ile
                1045                1050                1055

Val Met Val Leu Ala Leu Met Thr Val Glu Leu Phe Gly Met Met Gly
    1060                1065                1070

Leu Ile Gly Ile Lys Leu Ser Ala Val Pro Val Val Ile Leu Ile Ala
    1075                1080                1085

Ser Val Gly Ile Gly Val Glu Phe Thr Val His Val Ala Leu Ala Phe
    1090                1095                1100

Leu Thr Ala Ile Gly Asp Lys Asn Arg Arg Ala Val Leu Ala Leu Glu
1105                1110                1115                1120

His Met Phe Ala Pro Val Leu Asp Gly Ala Val Ser Thr Leu Leu Gly
                1125                1130                1135

Val Leu Met Leu Ala Gly Ser Glu Phe Asp Phe Ile Val Arg Tyr Phe
    1140                1145                1150

Phe Ala Val Leu Ala Ile Leu Thr Ile Leu Gly Val Leu Asn Gly Leu
    1155                1160                1165

Val Leu Leu Pro Val Leu Leu Ser Phe Phe Gly Pro Tyr Pro Glu Val
    1170                1175                1180

Ser Pro Ala Asn Gly Leu Asn Arg Leu Pro Thr Pro Ser Pro Glu Pro
1185                1190                1195                1200

Pro Pro Ser Val Val Arg Phe Ala Met Pro Pro Gly His Thr His Ser
                1205                1210                1215

Gly Ser Asp Ser Ser Asp Ser Glu Tyr Ser Ser Gln Thr Thr Val Ser
                1220                1225                1230

Gly Leu Ser Glu Glu Leu Arg His Tyr Glu Ala Gln Gln Gly Ala Gly
            1235                1240                1245

Gly Pro Ala His Gln Val Ile Val Glu Ala Thr Glu Asn Pro Val Phe
    1250                1255                1260

Ala His Ser Thr Val Val His Pro Glu Ser Arg His His Pro Pro Ser
1265                1270                1275                1280

Asn Pro Arg Gln Gln Pro His Leu Asp Ser Gly Ser Leu Pro Pro Gly
```

```
                    1285                1290                1295
Arg Gln Gly Gln Gln Pro Arg Arg Asp Pro Pro Arg Glu Gly Leu Trp
                1300                1305                1310
Pro Pro Pro Tyr Arg Pro Arg Arg Asp Ala Phe Glu Ile Ser Thr Glu
            1315                1320                1325
Gly His Ser Gly Pro Ser Asn Arg Ala Arg Trp Gly Pro Arg Gly Ala
        1330                1335                1340
Arg Ser His Asn Pro Arg Asn Pro Ala Ser Thr Ala Met Gly Ser Ser
1345                1350                1355                1360
Val Pro Gly Tyr Cys Gln Pro Ile Thr Thr Val Thr Ala Ser Ala Ser
                1365                1370                1375
Val Thr Val Ala Val His Pro Pro Val Pro Gly Pro Gly Arg Asn
                1380                1385                1390
Pro Arg Gly Gly Leu Cys Pro Gly Tyr Pro Glu Thr Asp His Gly Leu
            1395                1400                1405
Phe Glu Asp Pro His Val Pro Phe His Val Arg Cys Glu Arg Arg Asp
        1410                1415                1420
Ser Lys Val Glu Val Ile Glu Leu Gln Asp Val Glu Cys Glu Glu Arg
1425                1430                1435                1440
Pro Arg Gly Ser Ser Ser Asn
                1445

<210> SEQ ID NO 62
<211> LENGTH: 326
<212> TYPE: PRT
<213> ORGANISM: Homo sapiens

<400> SEQUENCE: 62

Met His Arg Thr Thr Arg Ile Lys Ile Thr Glu Leu Asn Pro His Leu
  1               5                  10                  15
Met Cys Val Leu Cys Gly Gly Tyr Phe Ile Asp Ala Thr Thr Ile Ile
                20                  25                  30
Glu Cys Leu His Ser Phe Cys Lys Thr Cys Ile Val Arg Tyr Leu Glu
            35                  40                  45
Thr Ser Lys Tyr Cys Pro Ile Cys Asp Val Gln Val His Lys Thr Arg
        50                  55                  60
Pro Leu Leu Asn Ile Arg Ser Asp Lys Thr Leu Gln Asp Ile Val Tyr
65                  70                  75                  80
Lys Leu Val Pro Gly Leu Phe Lys Asn Glu Met Lys Arg Arg Arg Asp
                85                  90                  95
Phe Tyr Ala Ala His Pro Ser Ala Asp Ala Ala Asn Gly Ser Asn Glu
            100                 105                 110
Asp Arg Gly Glu Val Ala Asp Glu Asp Lys Arg Ile Ile Thr Asp Asp
        115                 120                 125
Glu Ile Ile Ser Leu Ser Ile Glu Phe Phe Asp Gln Asn Arg Leu Asp
    130                 135                 140
Arg Lys Val Asn Lys Asp Lys Glu Lys Ser Lys Glu Glu Val Asn Asp
145                 150                 155                 160
Lys Arg Tyr Leu Arg Cys Pro Ala Ala Met Thr Val Met His Leu Arg
                165                 170                 175
Lys Phe Leu Arg Ser Lys Met Asp Ile Pro Asn Thr Phe Gln Ile Asp
            180                 185                 190
Val Met Tyr Glu Glu Glu Pro Leu Lys Asp Tyr Tyr Thr Leu Met Asp
        195                 200                 205
```

```
Ile Ala Tyr Ile Tyr Thr Trp Arg Arg Asn Gly Pro Leu Pro Leu Lys
210                 215                 220

Tyr Arg Val Arg Pro Thr Cys Lys Arg Met Lys Ile Ser His Gln Arg
225                 230                 235                 240

Asp Gly Leu Thr Asn Ala Gly Glu Leu Glu Ser Asp Ser Gly Ser Asp
                245                 250                 255

Lys Ala Asn Ser Pro Ala Gly Gly Ile Pro Ser Thr Ser Ser Cys Leu
                260                 265                 270

Pro Ser Pro Ser Thr Pro Val Gln Ser Pro His Pro Gln Phe Pro His
                275                 280                 285

Ile Ser Ser Thr Met Asn Gly Thr Ser Asn Ser Pro Ser Gly Asn His
290                 295                 300

Gln Ser Ser Phe Ala Asn Arg Pro Arg Lys Ser Ser Val Asn Gly Ser
305                 310                 315                 320

Ser Ala Thr Ser Ser Gly
                325

<210> SEQ ID NO 63
<211> LENGTH: 225
<212> TYPE: PRT
<213> ORGANISM: Homo sapiens

<400> SEQUENCE: 63

Met Val Ser His Ser Glu Leu Arg Lys Leu Phe Tyr Ser Ala Asp Ala
1               5                   10                  15

Val Cys Phe Asp Val Asp Ser Thr Val Ile Arg Glu Glu Gly Ile Asp
                20                  25                  30

Glu Leu Ala Lys Ile Cys Gly Val Glu Asp Ala Val Ser Glu Met Thr
            35                  40                  45

Arg Arg Ala Met Gly Gly Ala Val Pro Phe Lys Ala Ala Leu Thr Glu
50                  55                  60

Arg Leu Ala Leu Ile Gln Pro Ser Arg Glu Gln Val Gln Arg Leu Ile
65                  70                  75                  80

Ala Glu Gln Pro Pro His Leu Thr Pro Gly Ile Arg Glu Leu Val Ser
                85                  90                  95

Arg Leu Gln Glu Arg Asn Val Gln Val Phe Leu Ile Ser Gly Gly Phe
            100                 105                 110

Arg Ser Ile Val Glu His Val Ala Ser Lys Leu Asn Ile Pro Ala Thr
        115                 120                 125

Asn Val Phe Ala Asn Arg Leu Lys Phe Tyr Phe Asn Gly Glu Tyr Ala
130                 135                 140

Gly Phe Asp Glu Thr Gln Pro Thr Ala Glu Ser Gly Gly Lys Gly Lys
145                 150                 155                 160

Val Ile Lys Leu Leu Lys Glu Lys Phe His Phe Lys Lys Ile Ile Met
                165                 170                 175

Ile Gly Asp Gly Ala Thr Asp Met Glu Ala Cys Pro Pro Ala Asp Ala
            180                 185                 190

Phe Ile Gly Phe Gly Gly Asn Val Ile Arg Gln Gln Val Lys Asp Asn
        195                 200                 205

Ala Lys Trp Tyr Ile Thr Asp Phe Val Glu Leu Leu Gly Glu Leu Glu
210                 215                 220

Glu
225

<210> SEQ ID NO 64
```

```
<211> LENGTH: 264
<212> TYPE: PRT
<213> ORGANISM: Homo sapiens

<400> SEQUENCE: 64

Met Pro Arg Ser Phe Leu Val Arg Lys Pro Ser Asp Pro Asn Arg Lys
1               5                   10                  15

Pro Asn Tyr Ser Glu Leu Gln Asp Ser Asn Pro Glu Phe Thr Phe Gln
                20                  25                  30

Gln Pro Tyr Asp Gln Ala His Leu Leu Ala Ala Ile Pro Pro Pro Glu
            35                  40                  45

Ile Leu Asn Pro Thr Ala Ser Leu Pro Met Leu Ile Trp Asp Ser Val
    50                  55                  60

Leu Ala Pro Gln Ala Gln Pro Ile Ala Trp Ala Ser Leu Arg Leu Gln
65                  70                  75                  80

Glu Ser Pro Arg Val Ala Glu Leu Thr Ser Leu Ser Asp Glu Asp Ser
                85                  90                  95

Gly Lys Gly Ser Gln Pro Pro Ser Pro Pro Ser Pro Ala Pro Ser Ser
            100                 105                 110

Phe Ser Ser Thr Ser Val Ser Ser Leu Glu Ala Glu Ala Tyr Ala Ala
        115                 120                 125

Phe Pro Gly Leu Gly Gln Val Pro Lys Gln Leu Ala Gln Leu Ser Glu
    130                 135                 140

Ala Lys Asp Leu Gln Ala Arg Lys Ala Phe Asn Cys Lys Tyr Cys Asn
145                 150                 155                 160

Lys Glu Tyr Leu Ser Leu Gly Ala Leu Lys Met His Ile Arg Ser His
                165                 170                 175

Thr Leu Pro Cys Val Cys Gly Thr Cys Gly Lys Ala Phe Ser Arg Pro
            180                 185                 190

Trp Leu Leu Gln Gly His Val Arg Thr His Thr Gly Glu Lys Pro Phe
        195                 200                 205

Ser Cys Pro His Cys Ser Arg Ala Phe Ala Asp Arg Ser Asn Leu Arg
    210                 215                 220

Ala His Leu Gln Thr His Ser Asp Val Lys Lys Tyr Gln Cys Gln Ala
225                 230                 235                 240

Cys Ala Arg Thr Phe Ser Arg Met Ser Leu Leu His Lys His Gln Glu
                245                 250                 255

Ser Gly Cys Ser Gly Cys Pro Arg
            260

<210> SEQ ID NO 65
<211> LENGTH: 360
<212> TYPE: PRT
<213> ORGANISM: Homo sapiens

<400> SEQUENCE: 65

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80
```

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Ser Gln Asp Ile Lys Ala Leu Gln Lys
        130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 66
<211> LENGTH: 655
<212> TYPE: PRT
<213> ORGANISM: Homo sapiens

<400> SEQUENCE: 66

Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg

```
                    85                  90                  95
Lys Asp Pro Ser Gly Leu Ser Gly Asp Val Leu Ile Asn Gly Ala Pro
                100                 105                 110

Arg Pro Ala Asn Phe Lys Cys Asn Ser Gly Tyr Val Gln Asp Asp
            115                 120                 125

Val Val Met Gly Thr Leu Thr Val Arg Glu Asn Leu Gln Phe Ser Ala
        130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Ile Thr Val Phe Lys Glu Ile Ser
        355                 360                 365

Tyr Thr Thr Ser Phe Cys His Gln Leu Arg Trp Val Ser Lys Arg Ser
        370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510
```

```
Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
                580                 585                 590

Pro Gly Leu Asn Ala Thr Gly Asn Asn Pro Cys Asn Tyr Ala Thr Cys
                595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 67
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 67

Gln Thr Glu Glu Leu Thr Leu Gly Glu Phe
1               5                   10

<210> SEQ ID NO 68
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 68

Phe Thr Glu Leu Thr Leu Gly Glu Phe
1               5

<210> SEQ ID NO 69
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 69

Phe Ser Glu Leu Thr Leu Gly Glu Phe
1               5

<210> SEQ ID NO 70
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 70

Met Ala Glu Ala Gly Phe Ile His Tyr
1               5
```

<210> SEQ ID NO 71
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 71

Pro Thr Glu Asn Glu Pro Asp Leu Ala Tyr
1               5                   10

<210> SEQ ID NO 72
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 72

Thr Leu Pro Pro Ala Trp Gln Pro Lys
1               5

<210> SEQ ID NO 73
<211> LENGTH: 9
<212> TYPE: PRT
<213> ORGANISM: Artificial Sequence
<220> FEATURE:
<223> OTHER INFORMATION: synthetically generated peptide

<400> SEQUENCE: 73

Leu Leu Gln Cys Phe Phe Cys Phe Lys
1               5

<210> SEQ ID NO 74
<211> LENGTH: 10
<212> TYPE: PRT
<213> ORGANISM: Artificial Sequence
<220> FEATURE:
<223> OTHER INFORMATION: synthetically generated peptide

<400> SEQUENCE: 74

Arg Ile Ser Thr Phe Lys Asn Trp Pro Lys
1               5                   10

<210> SEQ ID NO 75
<211> LENGTH: 10
<212> TYPE: PRT
<213> ORGANISM: Homo sapiens

<400> SEQUENCE: 75

Glu Leu Thr Leu Gly Glu Phe Leu Lys Leu
1               5                   10

<210> SEQ ID NO 76
<211> LENGTH: 10
<212> TYPE: PRT
<213> ORGANISM: Homo sapiens

<400> SEQUENCE: 76

Thr Leu Pro Pro Ala Trp Gln Pro Phe Leu
1               5                   10

<210> SEQ ID NO 77
<211> LENGTH: 207
<212> TYPE: PRT

<213> ORGANISM: Homo sapiens

<400> SEQUENCE: 77

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Met Gln Cys Thr Ala
50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Tyr Gln Gln Leu Ala Ala Leu Ala Gly Asn Pro Lys Ala Ala Arg
        115                 120                 125

Ala Val Gly Gly Ala Met Arg Gly Asn Pro Val Pro Ile Leu Ile Pro
130                 135                 140

Cys His Arg Val Val Cys Ser Ser Gly Ala Val Gly Asn Tyr Ser Gly
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205

<210> SEQ ID NO 78
<211> LENGTH: 239
<212> TYPE: PRT
<213> ORGANISM: Homo sapiens

<400> SEQUENCE: 78

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
130                 135                 140

Gly Arg Ile Val Ala Phe Phe Glu Phe Gly Gly Val Met Cys Val Glu

```
                145                 150                 155                 160
        Ser Val Asn Arg Glu Met Ser Pro Leu Val Asp Asn Ile Ala Leu Trp
                            165                 170                 175

Met Thr Glu Tyr Leu Asn Arg His Leu His Thr Trp Ile Gln Asp Asn
                            180                 185                 190

Gly Gly Trp Asp Ala Phe Val Glu Leu Tyr Gly Pro Ser Met Arg Pro
                            195                 200                 205

Leu Phe Asp Phe Ser Trp Leu Ser Leu Lys Thr Leu Leu Ser Leu Ala
                            210                 215                 220

Leu Val Gly Ala Cys Ile Thr Leu Gly Ala Tyr Leu Gly His Lys
        225                 230                 235

<210> SEQ ID NO 79
<211> LENGTH: 480
<212> TYPE: PRT
<213> ORGANISM: Homo sapiens

<400> SEQUENCE: 79

Met Ser Ala Glu Val Ile His Gln Val Glu Ala Leu Asp Thr Asp
 1               5                  10                  15

Glu Lys Glu Met Leu Leu Phe Leu Cys Arg Asp Val Ala Ile Asp Val
                20                  25                  30

Val Pro Pro Asn Val Arg Asp Leu Leu Asp Ile Leu Arg Glu Arg Gly
            35                  40                  45

Lys Leu Ser Val Gly Asp Leu Ala Glu Leu Leu Tyr Arg Val Arg Arg
 50                  55                  60

Phe Asp Leu Leu Lys Arg Ile Leu Lys Met Asp Arg Lys Ala Val Glu
 65                  70                  75                  80

Thr His Leu Leu Arg Asn Pro His Leu Val Ser Asp Tyr Arg Val Leu
                85                  90                  95

Met Ala Glu Ile Gly Glu Asp Leu Asp Lys Ser Asp Val Ser Ser Leu
            100                 105                 110

Ile Phe Leu Met Lys Asp Tyr Met Gly Arg Gly Lys Ile Ser Lys Glu
        115                 120                 125

Lys Ser Phe Leu Asp Leu Val Val Glu Leu Glu Lys Leu Asn Leu Val
    130                 135                 140

Ala Pro Asp Gln Leu Asp Leu Leu Glu Lys Cys Leu Lys Asn Ile His
145                 150                 155                 160

Arg Ile Asp Leu Lys Thr Lys Ile Gln Lys Tyr Lys Gln Ser Val Gln
                165                 170                 175

Gly Ala Gly Thr Ser Tyr Arg Asn Val Leu Gln Ala Ala Ile Gln Lys
            180                 185                 190

Ser Leu Lys Asp Pro Ser Asn Asn Phe Arg Leu His Asn Gly Arg Ser
        195                 200                 205

Lys Glu Gln Arg Leu Lys Glu Gln Leu Gly Ala Gln Gln Glu Pro Val
    210                 215                 220

Lys Lys Ser Ile Gln Glu Ser Glu Ala Phe Leu Pro Gln Ser Ile Pro
225                 230                 235                 240

Glu Glu Arg Tyr Lys Met Lys Ser Lys Pro Leu Gly Ile Cys Leu Ile
                245                 250                 255

Ile Asp Cys Ile Gly Asn Glu Thr Glu Leu Leu Arg Asp Thr Phe Thr
            260                 265                 270

Ser Leu Gly Tyr Glu Val Gln Lys Phe Leu His Leu Ser Met His Gly
        275                 280                 285
```

```
Ile Ser Gln Ile Leu Gly Gln Phe Ala Cys Met Pro Glu His Arg Asp
    290                 295                 300
Tyr Asp Ser Phe Val Cys Val Leu Val Ser Arg Gly Gly Ser Gln Ser
305                 310                 315                 320
Val Tyr Gly Val Asp Gln Thr His Ser Gly Leu Pro Leu His His Ile
                325                 330                 335
Arg Arg Met Phe Met Gly Asp Ser Cys Pro Tyr Leu Ala Gly Lys Pro
                340                 345                 350
Lys Met Phe Phe Ile Gln Asn Tyr Val Val Ser Glu Gly Gln Leu Glu
                355                 360                 365
Asn Ser Ser Leu Leu Glu Val Asp Gly Pro Ala Met Lys Asn Val Glu
370                 375                 380
Phe Lys Ala Gln Lys Arg Gly Leu Cys Thr Val His Arg Glu Ala Asp
385                 390                 395                 400
Phe Phe Trp Ser Leu Cys Thr Ala Asp Met Ser Leu Leu Glu Gln Ser
                405                 410                 415
His Ser Ser Pro Ser Leu Tyr Leu Gln Cys Leu Ser Gln Lys Leu Arg
                420                 425                 430
Gln Glu Arg Lys Arg Pro Leu Leu Asp Leu His Ile Glu Leu Asn Gly
                435                 440                 445
Tyr Met Tyr Asp Trp Asn Ser Arg Val Ser Ala Lys Glu Lys Tyr Tyr
450                 455                 460
Val Trp Leu Gln His Thr Leu Arg Lys Lys Leu Ile Leu Ser Tyr Thr
465                 470                 475                 480

<210> SEQ ID NO 80
<211> LENGTH: 233
<212> TYPE: PRT
<213> ORGANISM: Homo sapiens

<400> SEQUENCE: 80

Met Ser Gln Ser Asn Arg Glu Leu Val Val Asp Phe Leu Ser Tyr Lys
1               5                   10                  15
Leu Ser Gln Lys Gly Tyr Ser Trp Ser Gln Phe Ser Asp Val Glu Glu
                20                  25                  30
Asn Arg Thr Glu Ala Pro Glu Gly Thr Glu Ser Glu Met Glu Thr Pro
            35                  40                  45
Ser Ala Ile Asn Gly Asn Pro Ser Trp His Leu Ala Asp Ser Pro Ala
    50                  55                  60
Val Asn Gly Ala Thr Gly His Ser Ser Ser Leu Asp Ala Arg Glu Val
65                  70                  75                  80
Ile Pro Met Ala Ala Val Lys Gln Ala Leu Arg Glu Ala Gly Asp Glu
                85                  90                  95
Phe Glu Leu Arg Tyr Arg Arg Ala Phe Ser Asp Leu Thr Ser Gln Leu
                100                 105                 110
His Ile Thr Pro Gly Thr Ala Tyr Gln Ser Phe Glu Gln Val Val Asn
                115                 120                 125
Glu Leu Phe Arg Asp Gly Val Asn Trp Gly Arg Ile Val Ala Phe Phe
        130                 135                 140
Ser Phe Gly Gly Ala Leu Cys Val Glu Ser Val Asp Lys Glu Met Gln
145                 150                 155                 160
Val Leu Val Ser Arg Ile Ala Ala Trp Met Ala Thr Tyr Leu Asn Asp
                165                 170                 175
His Leu Glu Pro Trp Ile Gln Glu Asn Gly Gly Trp Asp Thr Phe Val
                180                 185                 190
```

```
Glu Leu Tyr Gly Asn Asn Ala Ala Glu Ser Arg Lys Gly Gln Glu
        195                 200                 205

Arg Phe Asn Arg Trp Phe Leu Thr Gly Met Thr Val Ala Gly Val Val
        210                 215                 220

Leu Leu Gly Ser Leu Phe Ser Arg Lys
225                 230

<210> SEQ ID NO 81
<211> LENGTH: 497
<212> TYPE: PRT
<213> ORGANISM: Homo sapiens

<400> SEQUENCE: 81

Met Thr Phe Asn Ser Phe Glu Gly Ser Lys Thr Cys Val Pro Ala Asp
1               5                   10                  15

Ile Asn Lys Glu Glu Glu Phe Val Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80

Gly Arg His Arg Lys Val Ser Pro Asn Cys Arg Phe Ile Asn Gly Phe
                85                  90                  95

Tyr Leu Glu Asn Ser Ala Thr Gln Ser Thr Asn Ser Gly Ile Gln Asn
            100                 105                 110

Gly Gln Tyr Lys Val Glu Asn Tyr Leu Gly Ser Arg Asp His Phe Ala
        115                 120                 125

Leu Asp Arg Pro Ser Glu Thr His Ala Asp Tyr Leu Leu Arg Thr Gly
    130                 135                 140

Gln Val Val Asp Ile Ser Asp Thr Ile Tyr Pro Arg Asn Pro Ala Met
145                 150                 155                 160

Tyr Ser Glu Glu Ala Arg Leu Lys Ser Phe Gln Asn Trp Pro Asp Tyr
                165                 170                 175

Ala His Leu Thr Pro Arg Glu Leu Ala Ser Ala Gly Leu Tyr Tyr Thr
            180                 185                 190

Gly Ile Gly Asp Gln Val Gln Cys Phe Cys Gly Gly Lys Leu Lys
        195                 200                 205

Asn Trp Glu Pro Cys Asp Arg Ala Trp Ser Glu His Arg Arg His Phe
    210                 215                 220

Pro Asn Cys Phe Phe Val Leu Gly Arg Asn Leu Asn Ile Arg Ser Glu
225                 230                 235                 240

Ser Asp Ala Val Ser Ser Asp Arg Asn Phe Pro Asn Ser Thr Asn Leu
                245                 250                 255

Pro Arg Asn Pro Ser Met Ala Asp Tyr Glu Ala Arg Ile Phe Thr Phe
            260                 265                 270

Gly Thr Trp Ile Tyr Ser Val Asn Lys Glu Gln Leu Ala Arg Ala Gly
        275                 280                 285

Phe Tyr Ala Leu Gly Glu Gly Asp Lys Val Lys Cys Phe His Cys Gly
    290                 295                 300

Gly Gly Leu Thr Asp Trp Lys Pro Ser Glu Asp Pro Trp Glu Gln His
305                 310                 315                 320

Ala Lys Trp Tyr Pro Gly Cys Lys Tyr Leu Leu Glu Gln Lys Gly Gln
```

```
                        325                 330                 335
Glu Tyr Ile Asn Asn Ile His Leu Thr His Ser Leu Glu Glu Cys Leu
                340                 345                 350
Val Arg Thr Thr Glu Lys Thr Pro Ser Leu Thr Arg Arg Ile Asp Asp
            355                 360                 365
Thr Ile Phe Gln Asn Pro Met Val Gln Glu Ala Ile Arg Met Gly Phe
        370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                405                 410                 415
Ala Gln Lys Asp Ser Met Gln Asp Glu Ser Ser Gln Thr Ser Leu Gln
                420                 425                 430
Lys Glu Ile Ser Thr Glu Glu Gln Leu Arg Arg Leu Gln Glu Glu Lys
            435                 440                 445
Leu Cys Lys Ile Cys Met Asp Arg Asn Ile Ala Ile Val Phe Val Pro
        450                 455                 460
Cys Gly His Leu Val Thr Cys Lys Gln Cys Ala Glu Ala Val Asp Lys
465                 470                 475                 480
Cys Pro Met Cys Tyr Thr Val Ile Thr Phe Lys Gln Lys Ile Phe Met
                485                 490                 495
Ser

<210> SEQ ID NO 82
<211> LENGTH: 618
<212> TYPE: PRT
<213> ORGANISM: Homo sapiens

<400> SEQUENCE: 82

Met His Lys Thr Ala Ser Gln Arg Leu Phe Pro Gly Pro Ser Tyr Gln
  1               5                  10                  15
Asn Ile Lys Ser Ile Met Glu Asp Ser Thr Ile Leu Ser Asp Trp Thr
                 20                  25                  30
Asn Ser Asn Lys Gln Lys Met Lys Tyr Asp Phe Ser Cys Glu Leu Tyr
             35                  40                  45
Arg Met Ser Thr Tyr Ser Thr Phe Pro Ala Gly Val Pro Val Ser Glu
         50                  55                  60
Arg Ser Leu Ala Arg Ala Gly Phe Tyr Tyr Thr Gly Val Asn Asp Lys
65                  70                  75                  80
Val Lys Cys Phe Cys Cys Gly Leu Met Leu Asp Asn Trp Lys Leu Gly
                 85                  90                  95
Asp Ser Pro Ile Gln Lys His Lys Gln Leu Tyr Pro Ser Cys Ser Phe
                100                 105                 110
Ile Gln Asn Leu Val Ser Ala Ser Leu Gly Ser Thr Ser Lys Asn Thr
            115                 120                 125
Ser Pro Met Arg Asn Ser Phe Ala His Ser Leu Ser Pro Thr Leu Glu
        130                 135                 140
His Ser Ser Leu Phe Ser Gly Ser Tyr Ser Ser Leu Ser Pro Asn Pro
145                 150                 155                 160
Leu Asn Ser Arg Ala Val Glu Asp Ile Ser Ser Ser Arg Thr Asn Pro
                165                 170                 175
Tyr Ser Tyr Ala Met Ser Thr Glu Glu Ala Arg Phe Leu Thr Tyr His
                180                 185                 190
Met Trp Pro Leu Thr Phe Leu Ser Pro Ser Glu Leu Ala Arg Ala Gly
```

```
            195                 200                 205
Phe Tyr Tyr Ile Gly Pro Gly Asp Arg Val Ala Cys Phe Ala Cys Gly
210                 215                 220
Gly Lys Leu Ser Asn Trp Glu Pro Lys Asp Asp Ala Met Ser Glu His
225                 230                 235                 240
Arg Arg His Phe Pro Asn Cys Pro Phe Leu Glu Asn Ser Leu Glu Thr
            245                 250                 255
Leu Arg Phe Ser Ile Ser Asn Leu Ser Met Gln Thr His Ala Ala Arg
            260                 265                 270
Met Arg Thr Phe Met Tyr Trp Pro Ser Ser Val Pro Val Gln Pro Glu
            275                 280                 285
Gln Leu Ala Ser Ala Gly Phe Tyr Tyr Val Gly Arg Asn Asp Asp Val
            290                 295                 300
Lys Cys Phe Cys Cys Asp Gly Gly Leu Arg Cys Trp Glu Ser Gly Asp
305                 310                 315                 320
Asp Pro Trp Val Glu His Ala Lys Trp Phe Pro Arg Cys Glu Phe Leu
            325                 330                 335
Ile Arg Met Lys Gly Gln Glu Phe Val Asp Glu Ile Gln Gly Arg Tyr
            340                 345                 350
Pro His Leu Leu Glu Gln Leu Leu Ser Thr Ser Asp Thr Thr Gly Glu
            355                 360                 365
Glu Asn Ala Asp Pro Pro Ile Ile His Phe Gly Pro Gly Glu Ser Ser
370                 375                 380
Ser Glu Asp Ala Val Met Met Asn Thr Pro Val Val Lys Ser Ala Leu
385                 390                 395                 400
Glu Met Gly Phe Asn Arg Asp Leu Val Lys Gln Thr Val Gln Ser Lys
            405                 410                 415
Ile Leu Thr Thr Gly Glu Asn Tyr Lys Thr Val Asn Asp Ile Val Ser
            420                 425                 430
Ala Leu Leu Asn Ala Glu Asp Glu Lys Arg Glu Glu Glu Lys Glu Lys
            435                 440                 445
Gln Ala Glu Glu Met Ala Ser Asp Asp Leu Ser Leu Ile Arg Lys Asn
450                 455                 460
Arg Met Ala Leu Phe Gln Gln Leu Thr Cys Val Leu Pro Ile Leu Asp
465                 470                 475                 480
Asn Leu Leu Lys Ala Asn Val Ile Asn Lys Gln Glu His Asp Ile Ile
            485                 490                 495
Lys Gln Lys Thr Gln Ile Pro Leu Gln Ala Arg Glu Leu Ile Asp Thr
            500                 505                 510
Ile Leu Val Lys Gly Asn Ala Ala Ala Asn Ile Phe Lys Asn Cys Leu
            515                 520                 525
Lys Glu Ile Asp Ser Thr Leu Tyr Lys Asn Leu Phe Val Asp Lys Asn
            530                 535                 540
Met Lys Tyr Ile Pro Thr Glu Asp Val Ser Gly Leu Ser Leu Glu Glu
545                 550                 555                 560
Gln Leu Arg Arg Leu Gln Glu Glu Arg Thr Cys Lys Val Cys Met Asp
            565                 570                 575
Lys Glu Val Ser Val Val Phe Ile Pro Cys Gly His Leu Val Val Cys
            580                 585                 590
Gln Glu Cys Ala Pro Ser Leu Arg Lys Cys Pro Ile Cys Arg Gly Ile
            595                 600                 605
Ile Lys Gly Thr Val Arg Thr Phe Leu Ser
            610                 615
```

<210> SEQ ID NO 83
<211> LENGTH: 600
<212> TYPE: PRT
<213> ORGANISM: Homo sapiens

<400> SEQUENCE: 83

```
Met Val Gln Asp Ser Ala Phe Leu Ala Lys Leu Met Lys Ser Ala Asp
  1               5                  10                  15

Thr Phe Glu Leu Lys Tyr Asp Phe Ser Cys Glu Leu Tyr Arg Leu Ser
             20                  25                  30

Thr Tyr Ser Ala Phe Pro Arg Gly Val Pro Val Ser Glu Arg Ser Leu
         35                  40                  45

Ala Arg Ala Gly Phe Tyr Tyr Thr Gly Ala Asn Asp Lys Val Lys Cys
     50                  55                  60

Phe Cys Cys Gly Leu Met Leu Asp Asn Trp Lys Gln Gly Asp Ser Pro
 65                  70                  75                  80

Met Glu Lys His Arg Lys Leu Tyr Pro Ser Cys Asn Phe Val Gln Thr
                 85                  90                  95

Leu Asn Pro Ala Asn Ser Leu Glu Ala Ser Pro Arg Pro Ser Leu Pro
            100                 105                 110

Ser Thr Ala Met Ser Thr Met Pro Leu Ser Phe Ala Ser Ser Glu Asn
        115                 120                 125

Thr Gly Tyr Phe Ser Gly Ser Tyr Ser Ser Phe Pro Ser Asp Pro Val
    130                 135                 140

Asn Phe Arg Ala Asn Gln Asp Cys Pro Ala Leu Ser Thr Ser Pro Tyr
145                 150                 155                 160

His Phe Ala Met Asn Thr Glu Lys Ala Arg Leu Leu Thr Tyr Glu Thr
                165                 170                 175

Trp Pro Leu Ser Phe Leu Ser Pro Ala Lys Leu Ala Lys Ala Gly Phe
            180                 185                 190

Tyr Tyr Ile Gly Pro Gly Asp Arg Val Ala Cys Phe Ala Cys Asp Gly
        195                 200                 205

Lys Leu Ser Asn Trp Glu Arg Lys Asp Asp Ala Met Ser Glu His Gln
    210                 215                 220

Arg His Phe Pro Ser Cys Pro Phe Leu Lys Asp Leu Gly Gln Ser Ala
225                 230                 235                 240

Ser Arg Tyr Thr Val Ser Asn Leu Ser Met Gln Thr His Ala Ala Arg
                245                 250                 255

Ile Arg Thr Phe Ser Asn Trp Pro Ser Ser Ala Leu Val His Ser Gln
            260                 265                 270

Glu Leu Ala Ser Ala Gly Phe Tyr Tyr Thr Gly His Ser Asp Asp Val
        275                 280                 285

Lys Cys Phe Cys Cys Asp Gly Gly Leu Arg Cys Trp Glu Ser Gly Asp
    290                 295                 300

Asp Pro Trp Val Glu His Ala Lys Trp Phe Pro Arg Cys Glu Tyr Leu
305                 310                 315                 320

Leu Arg Ile Lys Gly Gln Glu Phe Val Ser Gln Val Gln Ala Gly Tyr
                325                 330                 335

Pro His Leu Leu Glu Gln Leu Leu Ser Thr Ser Asp Ser Pro Glu Asp
            340                 345                 350

Glu Asn Ala Asp Ala Ala Ile Val His Phe Gly Pro Gly Glu Ser Ser
        355                 360                 365

Glu Asp Val Val Met Met Ser Thr Pro Val Val Lys Ala Ala Leu Glu
```

```
              370                 375                 380
Met Gly Phe Ser Arg Ser Leu Val Arg Gln Thr Val Gln Arg Gln Ile
385                 390                 395                 400

Leu Ala Thr Gly Glu Asn Tyr Arg Thr Val Ser Asp Leu Val Ile Gly
            405                 410                 415

Leu Leu Asp Ala Glu Asp Glu Met Arg Glu Gln Met Glu Gln Ala
            420                 425                 430

Ala Glu Glu Glu Ser Asp Asp Leu Ala Leu Ile Arg Lys Asn Lys
        435                 440                 445

Met Val Leu Phe Gln His Leu Thr Cys Val Thr Pro Met Leu Tyr Cys
            450                 455                 460

Leu Leu Ser Ala Arg Ala Ile Thr Glu Gln Glu Cys Asn Ala Val Lys
465                 470                 475                 480

Gln Lys Pro His Thr Leu Gln Ala Ser Thr Leu Ile Asp Thr Val Leu
            485                 490                 495

Ala Lys Gly Asn Thr Ala Ala Thr Ser Phe Arg Asn Ser Leu Arg Glu
            500                 505                 510

Ile Asp Pro Ala Leu Tyr Arg Asp Ile Phe Val Gln Gln Asp Ile Arg
            515                 520                 525

Ser Leu Pro Thr Asp Asp Ile Ala Ala Leu Pro Met Glu Glu Gln Leu
530                 535                 540

Arg Lys Leu Gln Glu Glu Arg Met Cys Lys Val Cys Met Asp Arg Glu
545                 550                 555                 560

Val Ser Ile Val Phe Ile Pro Cys Gly His Leu Val Val Cys Lys Asp
                565                 570                 575

Cys Ala Pro Ser Leu Arg Lys Cys Pro Ile Cys Arg Gly Thr Ile Lys
                580                 585                 590

Gly Thr Val Arg Thr Phe Leu Ser
            595                 600

<210> SEQ ID NO 84
<211> LENGTH: 1403
<212> TYPE: PRT
<213> ORGANISM: Homo sapiens

<400> SEQUENCE: 84

Met Ala Thr Gln Gln Lys Ala Ser Asp Glu Arg Ile Ser Gln Phe Asp
1               5                   10                  15

His Asn Leu Leu Pro Glu Leu Ser Ala Leu Leu Gly Leu Asp Ala Val
                20                  25                  30

Gln Leu Ala Lys Glu Leu Glu Glu Glu Gln Lys Glu Arg Ala Lys
            35                  40                  45

Met Gln Lys Gly Tyr Asn Ser Gln Met Arg Ser Glu Ala Lys Arg Leu
50                  55                  60

Lys Thr Phe Val Thr Tyr Glu Pro Tyr Ser Ser Trp Ile Pro Gln Glu
65                  70                  75                  80

Met Ala Ala Ala Gly Phe Tyr Phe Thr Gly Val Lys Ser Gly Ile Gln
                85                  90                  95

Cys Phe Cys Cys Ser Leu Ile Leu Phe Gly Ala Gly Leu Thr Arg Leu
                100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
        130                 135                 140
```

```
Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
        195                 200                 205

Glu Gly Asp Asp Pro Trp Lys Glu His Ala Lys Trp Phe Pro Lys Cys
    210                 215                 220

Glu Phe Leu Arg Ser Lys Lys Ser Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
    290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
    370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
        435                 440                 445

Val Gln Glu Pro Leu Val Leu Pro Glu Val Phe Gly Asn Leu Asn Ser
    450                 455                 460

Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
        515                 520                 525

Ser Val Thr Glu Met Cys Val Arg Asn Ile Ile Gln Gln Leu Lys Asn
    530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
```

-continued

```
                565                 570                 575
Leu Leu Ile Ala Val Arg Thr Asn Arg Ala Arg Asp Ile Arg Arg Tyr
            580                 585                 590
Leu Glu Thr Ile Leu Glu Ile Lys Ala Phe Pro Phe Tyr Asn Thr Val
            595                 600                 605
Cys Ile Leu Arg Lys Leu Phe Ser His Asn Met Thr Arg Leu Arg Lys
            610                 615                 620
Phe Met Val Tyr Phe Gly Lys Asn Gln Ser Leu Gln Lys Ile Gln Lys
625                 630                 635                 640
Thr Pro Leu Phe Val Ala Ala Ile Cys Ala His Trp Phe Gln Tyr Pro
            645                 650                 655
Phe Asp Pro Ser Phe Asp Val Ala Val Phe Lys Ser Tyr Met Glu
            660                 665                 670
Arg Leu Ser Leu Arg Asn Lys Ala Thr Ala Glu Ile Leu Lys Ala Thr
            675                 680                 685
Val Ser Ser Cys Gly Glu Leu Ala Leu Lys Gly Phe Phe Ser Cys Cys
            690                 695                 700
Phe Glu Phe Asn Asp Asp Leu Ala Glu Ala Gly Val Asp Glu Asp
705                 710                 715                 720
Glu Asp Leu Thr Met Cys Leu Met Ser Lys Phe Thr Ala Gln Arg Leu
            725                 730                 735
Arg Pro Phe Tyr Arg Phe Leu Ser Pro Ala Phe Gln Glu Phe Leu Ala
            740                 745                 750
Gly Met Arg Leu Ile Glu Leu Leu Asp Ser Asp Arg Gln Glu His Gln
            755                 760                 765
Asp Leu Gly Leu Tyr His Leu Lys Gln Ile Asn Ser Pro Met Met Thr
770                 775                 780
Val Ser Ala Tyr Asn Asn Phe Leu Asn Tyr Val Ser Ser Leu Pro Ser
785                 790                 795                 800
Thr Lys Ala Gly Pro Lys Ile Val Ser His Leu Leu His Leu Val Asp
            805                 810                 815
Asn Lys Glu Ser Leu Glu Asn Ile Ser Glu Asn Asp Asp Tyr Leu Lys
            820                 825                 830
His Gln Pro Glu Ile Ser Leu Gln Met Gln Leu Leu Arg Gly Leu Trp
            835                 840                 845
Gln Ile Cys Pro Gln Ala Tyr Phe Ser Met Val Ser Glu His Leu Leu
850                 855                 860
Val Leu Ala Leu Lys Thr Ala Tyr Gln Ser Asn Thr Val Ala Ala Cys
865                 870                 875                 880
Ser Pro Phe Val Leu Gln Phe Leu Gln Gly Arg Thr Leu Thr Leu Gly
            885                 890                 895
Ala Leu Asn Leu Gln Tyr Phe Phe Asp His Pro Glu Ser Leu Ser Leu
            900                 905                 910
Leu Arg Ser Ile His Phe Pro Ile Arg Gly Asn Lys Thr Ser Pro Arg
            915                 920                 925
Ala His Phe Ser Val Leu Glu Thr Cys Phe Asp Lys Ser Gln Val Pro
            930                 935                 940
Thr Ile Asp Gln Asp Tyr Ala Ser Ala Phe Glu Pro Met Asn Glu Trp
945                 950                 955                 960
Glu Arg Asn Leu Ala Glu Lys Glu Asp Asn Val Lys Ser Tyr Met Asp
            965                 970                 975
Met Gln Arg Arg Ala Ser Pro Asp Leu Ser Thr Gly Tyr Trp Lys Leu
            980                 985                 990
```

-continued

```
Ser Pro Lys Gln Tyr Lys Ile Pro Cys Leu Glu Val Asp Val Asn Asp
    995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
                1060                1065                1070

Leu Leu Thr Leu Pro Ser Leu Ser Leu Glu Val Ser Gly Thr Ile
    1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
                1125                1130                1135

Gln Ile Ser Ala Glu Tyr Asp Pro Ser Lys Leu Val Lys Leu Ile Gln
    1140                1145                1150

Asn Ser Pro Asn Leu His Val Phe His Leu Lys Cys Asn Phe Phe Ser
    1155                1160                1165

Asp Phe Gly Ser Leu Met Thr Met Leu Val Ser Cys Lys Lys Leu Thr
    1170                1175                1180

Glu Ile Lys Phe Ser Asp Ser Phe Phe Gln Ala Val Pro Phe Val Ala
1185                1190                1195                1200

Ser Leu Pro Asn Phe Ile Ser Leu Lys Ile Leu Asn Leu Glu Gly Gln
                1205                1210                1215

Gln Phe Pro Asp Glu Glu Thr Ser Glu Lys Phe Ala Tyr Ile Leu Gly
    1220                1225                1230

Ser Leu Ser Asn Leu Glu Glu Leu Ile Leu Pro Thr Gly Asp Gly Ile
    1235                1240                1245

Tyr Arg Val Ala Lys Leu Ile Ile Gln Gln Cys Gln Gln Leu His Cys
    1250                1255                1260

Leu Arg Val Leu Ser Phe Phe Lys Thr Leu Asn Asp Asp Ser Val Val
1265                1270                1275                1280

Glu Ile Ala Lys Val Ala Ile Ser Gly Gly Phe Gln Lys Leu Glu Asn
                1285                1290                1295

Leu Lys Leu Ser Ile Asn His Lys Ile Thr Glu Glu Gly Tyr Arg Asn
                1300                1305                1310

Phe Phe Gln Ala Leu Asp Asn Met Pro Asn Leu Gln Glu Leu Asp Ile
    1315                1320                1325

Ser Arg His Phe Thr Glu Cys Ile Lys Ala Gln Ala Thr Thr Val Lys
    1330                1335                1340

Ser Leu Ser Gln Cys Val Leu Arg Leu Pro Arg Leu Ile Arg Leu Asn
1345                1350                1355                1360

Met Leu Ser Trp Leu Leu Asp Ala Asp Asp Ile Ala Leu Leu Asn Val
                1365                1370                1375

Met Lys Glu Arg His Pro Gln Ser Lys Tyr Leu Thr Ile Leu Gln Lys
                1380                1385                1390

Trp Ile Leu Pro Phe Ser Pro Ile Ile Gln Lys
    1395                1400
```

```
<210> SEQ ID NO 85
<211> LENGTH: 142
<212> TYPE: PRT
<213> ORGANISM: Homo sapiens

<400> SEQUENCE: 85

Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Lys His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Glu Phe Glu Glu Thr Ala
        115                 120                 125

Glu Lys Val Arg Arg Ala Ile Glu Gln Leu Ala Ala Met Asp
    130                 135                 140

<210> SEQ ID NO 86
<211> LENGTH: 9
<212> TYPE: PRT
<213> ORGANISM: Homo sapiens

<400> SEQUENCE: 86

Thr Leu Gln Asp Ile Val Tyr Lys Leu
1               5

<210> SEQ ID NO 87
<211> LENGTH: 9
<212> TYPE: PRT
<213> ORGANISM: Homo sapiens

<400> SEQUENCE: 87

Cys Leu Pro Ser Pro Ser Thr Pro Val
1               5

<210> SEQ ID NO 88
<211> LENGTH: 9
<212> TYPE: PRT
<213> ORGANISM: Homo sapiens

<400> SEQUENCE: 88

Val Arg Tyr Leu Glu Thr Ser Lys Tyr
1               5

<210> SEQ ID NO 89
<211> LENGTH: 9
<212> TYPE: PRT
<213> ORGANISM: Homo sapiens

<400> SEQUENCE: 89

Lys Arg Tyr Leu Arg Cys Pro Ala Ala
1               5
```

```
<210> SEQ ID NO 90
<211> LENGTH: 9
<212> TYPE: PRT
<213> ORGANISM: Homo sapiens

<400> SEQUENCE: 90

Tyr Glu Glu Glu Pro Leu Lys Asp Tyr
1               5

<210> SEQ ID NO 91
<211> LENGTH: 9
<212> TYPE: PRT
<213> ORGANISM: Homo sapiens

<400> SEQUENCE: 91

Lys Glu Glu Val Asn Asp Lys Arg Tyr
1               5

<210> SEQ ID NO 92
<211> LENGTH: 9
<212> TYPE: PRT
<213> ORGANISM: Homo sapiens

<400> SEQUENCE: 92

Thr Ala Tyr Gln Ser Phe Glu Gln Val
1               5

<210> SEQ ID NO 93
<211> LENGTH: 10
<212> TYPE: PRT
<213> ORGANISM: Homo sapiens

<400> SEQUENCE: 93

Tyr Leu Asn Asp His Leu Glu Pro Trp Ile
1               5                   10

<210> SEQ ID NO 94
<211> LENGTH: 10
<212> TYPE: PRT
<213> ORGANISM: Homo sapiens

<400> SEQUENCE: 94

Trp Met Ala Thr Tyr Leu Asn Asp His Leu
1               5                   10

<210> SEQ ID NO 95
<211> LENGTH: 9
<212> TYPE: PRT
<213> ORGANISM: Homo sapiens

<400> SEQUENCE: 95

Ser Thr Phe Lys Asn Trp Pro Phe Leu
1               5

<210> SEQ ID NO 96
<211> LENGTH: 9
<212> TYPE: PRT
<213> ORGANISM: Homo sapiens

<400> SEQUENCE: 96

Leu Thr Leu Gly Glu Phe Leu Lys Leu
1               5

<210> SEQ ID NO 97
```

<211> LENGTH: 9
<212> TYPE: PRT
<213> ORGANISM: Homo sapiens

<400> SEQUENCE: 97

Arg Ala Ile Glu Gln Leu Ala Ala Met
1               5

<210> SEQ ID NO 98
<211> LENGTH: 10
<212> TYPE: PRT
<213> ORGANISM: Homo sapiens

<400> SEQUENCE: 98

Glu Thr Ala Lys Lys Val Arg Arg Ala Ile
1               5                   10

<210> SEQ ID NO 99
<211> LENGTH: 10
<212> TYPE: PRT
<213> ORGANISM: Homo sapiens

<400> SEQUENCE: 99

Gln Phe Glu Glu Leu Thr Leu Gly Glu Phe
1               5                   10

<210> SEQ ID NO 100
<211> LENGTH: 9
<212> TYPE: PRT
<213> ORGANISM: Homo sapiens

<400> SEQUENCE: 100

Leu Ala Gln Cys Phe Phe Cys Phe Lys
1               5

<210> SEQ ID NO 101
<211> LENGTH: 9
<212> TYPE: PRT
<213> ORGANISM: Homo sapiens

<400> SEQUENCE: 101

Lys Ile Ala Lys Glu Thr Asn Asn Lys
1               5

<210> SEQ ID NO 102
<211> LENGTH: 10
<212> TYPE: PRT
<213> ORGANISM: Homo sapiens

<400> SEQUENCE: 102

Asp Leu Ala Gln Cys Phe Phe Cys Phe Lys
1               5                   10

<210> SEQ ID NO 103
<211> LENGTH: 10
<212> TYPE: PRT
<213> ORGANISM: Homo sapiens

<400> SEQUENCE: 103

Lys Ile Ala Lys Glu Thr Asn Asn Lys Lys
1               5                   10

<210> SEQ ID NO 104
<211> LENGTH: 11
<212> TYPE: PRT

```
<213> ORGANISM: Homo sapiens

<400> SEQUENCE: 104

Arg Ile Ser Thr Phe Lys Asn Trp Pro Phe Leu
 1               5                  10

<210> SEQ ID NO 105
<211> LENGTH: 11
<212> TYPE: PRT
<213> ORGANISM: Homo sapiens

<400> SEQUENCE: 105

Phe Leu Ser Val Lys Lys Gln Phe Glu Glu Leu
 1               5                  10
```

CANCER STEM CELL ANTIGEN VACCINES AND METHODS

CROSS-REFERENCE TO RELATED APPLICATIONS

This application is a continuation of U.S. application Ser. No. 11/862,135, filed on Sep. 26, 2007, which claims the benefit of priority to U.S. Provisional Patent Application Ser. No. 60/826,955, filed on Sep. 26, 2006; each of these prior applications is incorporated herein by reference in their entirety.

BACKGROUND

Over the past 30 years, a wealth of information has been generated concerning the in vivo and in vitro properties of brain tumors and rodent models of brain tumor. The 9L gliosarcoma, which was generated from inbred Fisher rats, is a widely used syngeneic rat model for brain tumors. Originally produced by N-methyl-nitrosourea mutagenesis in Fisher rats, the tumor was cloned and designated 9L gliosarcoma because of its dual appearance of a glioblastoma and a sarcoma (Benda et al., J. Neurosurg., 34:310-323, 1971; Schmidek et al., J. Neurosurg., 34:335-340, 1971). The tumor could be proliferated under in vivo and in vitro conditions, making it a useful candidate as a glioma tumor model. The 9L gliosarcoma model clinically mimics rapidly growing and fatal intracerebral tumors, making it the most widely used rat brain tumor model.

Stem cells have been defined as multipotent, self-renewing cells with the potential to differentiate into multiple cell types. Systems have been developed to identify the first neural stem cells in a defined media, whereby striatal embryonic progenitors could be harvested and grown in culture as undifferentiated neurospheres (clonally derived aggregates of cells derived from a single stem cell) under the influence of the mitogens EGF and bFGF. Many of these cells expressed nestin (an intermediate filament found in neuroepithelial stem cells), but not markers for the more differentiated principal cell types of the CNS—neuronal and glial cells. However, when grown on coverslips treated with poly-L-ornithine, a substrate that allows cellular adhesion, many of the cells within the neurospheres differentiated into neurons and astrocytes with discontinued nestin expression. The isolated striatal cells fulfilled the critical features expected from neural stem cells: an unlimited capacity for self-renewal and capacity to differentiate into the principal mature neural cells (Potten et al., Development, 110:1001-1020, 1990; Lee et al., Nat. Neurosci., 8:723-729, 2005; Maric et al., J. Neurosci., 23:240-251, 2003; Weissman et al., Annu. Rev. Cell. Dev. Biol., 17:387-403, 2001; Seaberg et al., Trends Neurosci., 26:125-131, 2003; Reya et al., Nature, 414:105-111, 2001). Under similar circumstances "cancer stem cells" appear to have the same characteristics of self-renewal and multipotentcy.

Malignant brain tumors carry a poor prognosis even in the midst of surgical, radio-, and chemotherapy. With the poor prognosis of brain tumors amidst the available therapeutic treatments, there exists a significant need for more effective therapies to treat such tumors.

SUMMARY

This invention is based, inter alia, on the discovery that vaccines based on cancer stem cell antigens are exceptionally useful for therapy of cancer. Immunization of animals with dendritic cells pulsed with antigens from isolated cancer stem cells provided a significant survival benefit as compared to immunization with dendritic cells pulsed with differentiated tumor cells. Cancer stem cells were found to express major histocompatibility (MHC), indicating that they can display antigens. Further, proteins differentially expressed in cancer stem cells as compared to differentiated tumor cells were identified. These proteins can be useful in providing antigenic compositions for treatment of cancers (e.g., neural cancers such as gliomas).

Accordingly, this application provides methods and compositions for cancer vaccines that target cancer stem cells. Cancer stem cells are important in tumor maintenance, proliferation, and resistance to chemotherapy and radiation therapy. Thus, the new vaccines that target cancer stem cells provide for greater therapeutic and/or prophylactic effect, particularly in cancers that are resistant to conventional treatments.

In one aspect, this application provides methods of treating cancer (e.g., neural cancer) in a patient that include administering to the patient a composition that includes antigen presenting cells (e.g., dendritic cells) that present cancer stem cell antigens (e.g., neural stem cell antigens).

In another aspect, this application provides methods of treating cancer (e.g., neural cancer) in a patient that include the steps of: obtaining a population of antigen presenting cells (e.g., dendritic cells); contacting the antigen presenting cells with a cancer stem cell antigen composition (e.g., a neural cancer stem cell antigen composition) under conditions such that the antigen presenting cells present cancer stem cell antigens (e.g., neural cancer stem cell antigens); and administering to a patient a composition that includes the antigen presenting cells.

In a further aspect, this application provides methods of inducing or stimulating an immune response in a patient, and methods of generating antibodies specific for cancer stem cell antigens, that include administering to the patient a composition that includes antigen presenting cells (e.g., dendritic cells) that present cancer stem cell antigens (e.g., neural stem cell antigens).

In another aspect, this application provides methods of inducing or stimulating an immune response in a patient, and methods of generating antibodies specific for cancer stem cell antigens, by obtaining a population of antigen presenting cells (e.g., dendritic cells); contacting the dendritic cells with a cancer stem cell antigen composition (e.g., a neural cancer stem cell antigen composition) under conditions such that the antigen presenting cells present cancer stem cell antigens (e.g., neural cancer stem cell antigens); and administering to a patient a composition that includes the antigen presenting cells.

In a further aspect, this application provides methods of preparing a cancer vaccine (e.g., a neural cancer vaccine), that include the steps of: obtaining a population of antigen presenting cells (e.g., dendritic cells), and contacting the antigen presenting cells with a cancer stem cell antigen composition (e.g., a neural cancer stem cell antigen composition) under conditions such that the antigen presenting cells present cancer stem cell antigens (e.g., neural cancer stem cell antigens), thus preparing a cancer vaccine. In some embodiments, the methods further include administering the vaccine to a patient.

In another aspect, this application provides methods of preparing a cell vaccine for treating a cancer (e.g., a neural cancer) by obtaining mononuclear cells from a subject; culturing the mononuclear cells in vitro under conditions in which mononuclear cells differentiate into antigen presenting cells; isolating cancer stem cells (e.g., neural cancer stem cells) from the same or different subject; preparing a cancer stem cell antigen composition (e.g., a neural cancer stem cell antigen composition) from the cancer stem cells; and culturing the antigen presenting cells in the presence of the cancer stem cell antigen composition, thus preparing a cell vaccine. In some embodiments, the methods further include administering the vaccine to a patient.

In some embodiments of any of the above aspects, the antigen presenting cells are autologous to the subject or patient. In some embodiments, the antigen presenting cells are allogeneic to the subject or patient.

In some embodiments of any of the above aspects, the cancer stem cell antigen composition is a lysate of cancer stem cells (e.g., neural stem cells). In other embodiments, the cancer stem cell antigen composition is an acid eluate of cancer stem cells (e.g., neural cancer stem cells).

In some embodiments of any of the above aspects, the neural cancer stem cell antigen composition is obtained from a brain tumor (e.g., a glioma). In some embodiments of any of the above aspects, the cancer stem cells express CD133. In some embodiments of any of the above aspects, the cancer stem cell antigen composition includes one or more isolated peptides of CD133, CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, or survivin. In some embodiments, the peptides are synthetic.

In another aspect, this application provides kits for preparing a cell vaccine for inducing an immune response or treating a cancer (e.g., a brain cancer) that include one or more isolated peptides of CD133, CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, or survivin.

In a further aspect, this application provides compositions (e.g., immunomodulatory compositions) that include antigen presenting cells (e.g., dendritic cells) that present cancer stem cell antigens (e.g., neural cancer stem cell antigens). In some embodiments, the cancer stem cell antigens include peptides of one or more of CD133, CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, or survivin. In some embodiments, the compositions are produced by methods described herein.

In another aspect, this application provides for the use of compositions (e.g., immunomodulatory compositions) that include antigen presenting cells (e.g., dendritic cells) that present cancer stem cell antigens (e.g., neural cancer stem cell antigens) in the preparation of a medicament for modulating an immune response or treating cancer in a subject. In some embodiments, the cancer stem cell antigens include peptides of one or more of CD133, CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, or survivin. In certain embodiments, the compositions are produced by methods described herein.

This application also provides immunogenic compositions that include, or encode cancer stem cell antigens, and methods of using the compositions. For example, preparations of cancer stem cell antigens, for use as cancer vaccines (e.g., peptide vaccines, DNA vaccines) are provided.

"Beneficial results" may include, but are in no way limited to, lessening or alleviating the severity of a disease condition, inhibiting the disease condition from worsening, improving symptoms of a disease condition, and prolonging a patient's life or life expectancy.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas.

"Conditions" and "disease conditions," as used herein may include, but are in no way limited to any form of neoplastic cell growth and proliferation, whether malignant or benign, pre-cancerous and cancerous cells and tissues; in particular, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term. The terms "patient" and "subject" are used herein interchangeably, and cover mammals, including humans.

"Pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stem-like" or "stem," as used herein refers to cells that are able to self renew from a single clone, differentiate into terminal cell types, and be serially transplantable in immunodeficient animals.

"Treatment" and "treating," as used herein refer to both therapeutic treatment and prophylactic or preventative measures, wherein the object is to prevent or slow down (lessen) the targeted pathologic condition or disorder even if the treatment is ultimately unsuccessful. Those in need of treatment include those already diagnosed as having the disorder as well as those prone to have the disorder or those in whom the disorder is to be prevented. For example, in tumor (e.g., cancer) treatment, a therapeutic agent may directly decrease the pathology of tumor cells, or render the tumor cells more susceptible to treatment by other therapeutic agents or by the subject's own immune system.

"Tumor," as used herein refers to all neoplastic cell growth and proliferation, whether malignant or benign, and all precancerous and cancerous cells and tissues.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference herein in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE FIGURES

FIGS. 5A-5E are a set of micrographs of tumors formed by implantation of neurospheres. (5A) neurospheres formed high grade gliomas with necrosis as seen on H&E; (5B) large and well circumferential tumors grew as evidenced in non-stained sections; (5C) large and well circumferential tumors grew as evidenced in sections stained for the nuclear marker DAPI; (5D) & (5E) comparison of non-tumor area (5D) and tumor area (5E) stained for reticulin reveals the high levels of reticulin formed in tumor engulfed regions, showing the histological sarcomatous component of the gliosarcoma. Scale bar=3000 µm (5A) Scale bar=1250 µm (5B, 5C); Scale bar=250 µm (5D, 5E).

FIGS. 10A-10D are line graphs depicting drug sensitivity of CD133 positive cancer stem cells derived from patient No. 66. Tumor cells of No. 66 were cultured in FBS/F-12/DMEM medium for 4 passages. Both CD133 positive and negative tumor cells were collected by FACS sorting. $1\times10^4$ cells/well were plated in 96-well plate and treated with the indicated concentrations of VP-16, Taxol, temozolomide, and carboplatin for 48 hours in FBS/F-12/DMEM medium. * indicates $p<0.05$ compared to autologous CD133 negative cells. Data are representative of two independent experiments. (10A) VP16; (10B) Taxol; (10C) temozolomide; (10D) carboplatin.

FIGS. 11A-11C are a set of line graphs depicting drug sensitivity of CD133 positive cancer stem cells derived from patient Nos. 377 and 1049. Tumor cells of patient No. 377 and No. 1049 were cultured in FBS/F-12/DMEM medium for 3 passages. Both CD133 positive and negative tumor cells were collected by FACS sorting. $1\times10^4$ cells/well were plated in 96-well plate and treated with the indicated concentrations of carboplatin (11A and 11C) or VP-16 (11B) for 48 hours in FBS/F-12/DMAEM medium. * indicates $p<0.05$ compared to autologous CD133 negative cells. Data are representative of two independent experiments.

DC), 9L neurospheres (9L-NS), and dendritic cells alone (CONTROL). Kaplan-Meier survival curve showed that the 9L-DC group had significantly longer survival than the other groups (p=0.0015).

FIG. 14 is a bar graph depicting IFNγ production of splenocytes harvested from tumor bearing rats that were re-stimulated and by either re-exposure to a 9L tumor cell target (Target) or to no target (NO Target). The re-stimulated splenocytes from NS vaccinated rats released high level of IFNγ when re-exposed to NS, whereas splenocytes from rats vaccinated with AC or DtC had no detectable IFNγ in response to re-exposure to AC or DC.

FIGS. 15A and 15B are a pair of micrographs of tumor slices from rats vaccinated with dendritic cells pulsed with daughter cells (17A) and neurospheres (17B) and stained with anti-CD4 antibody. Greater infiltration of CD4+ cells was observed in the tumors of rats vaccinated with neurosphere-pulsed dendritic cells. (Magnification ×40).

Figure 16:
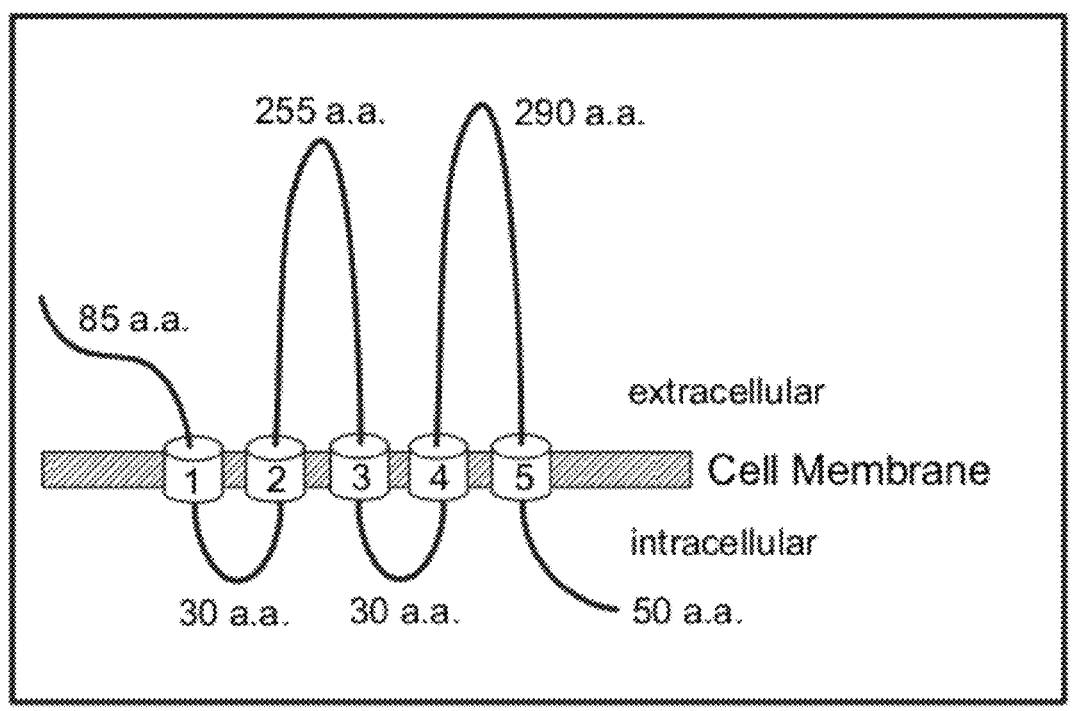

FIG. 16 is a structural diagram of CD133 depicting extracellular, intracellular, and transmembrane regions of CD133.

FIGS. 17A and 17B are cell plots and histograms depicting expression of isotype control (17A) and MHC class I expression (17B) in human cancer stem cells.

FIGS. 18A and 18B are cell plots and histograms depicting expression of isotype control (18A) and MHC class I expression (18B) in human neural stem cells.

DETAILED DESCRIPTION

The present application describes compositions useful as vaccines for treating cancer (e.g., neural cancers, e.g., gliomas) that include dendritic cells pulsed with antigens obtained from cancer stem cells (e.g., neurospheres); methods of producing vaccines that include dendritic cells pulsed with antigens obtained from cancer stem cells; methods of treating cancer with vaccines that include dendritic cells pulsed with antigens obtained from cancer stem cells; and kits for treating cancer that include dendritic cells pulsed with antigens obtained from cancer stem cells.

Greater tumor infiltration of cytotoxic T cells was observed in animals vaccinated against cancer stem cell antigens, and a stronger response against tumor cells was observed in T cells isolated from animals vaccinated with cancer stem cell antigens, than in responses in which antigens were not prepared from stem cell enriched cell populations. Cancer stem cells obtained from brain tumors were capable of self-renewal and proliferation, and could recapitulate the tumor when injected into rats. Isolated cancer stem cells formed more aggressive tumors as compared to differentiated tumor cells in vitro, and the cancer stem cells showed a higher resistance to chemotherapeutic agents. Similarly, CD133-positive cancer stem cells were obtained from human tumors. These cells were similarly resistant to chemotherapeutic agents and CD133-positive cells were found at a higher level in patients in whom tumors had recurred following resection.

Vaccination Methods

Figure 1:
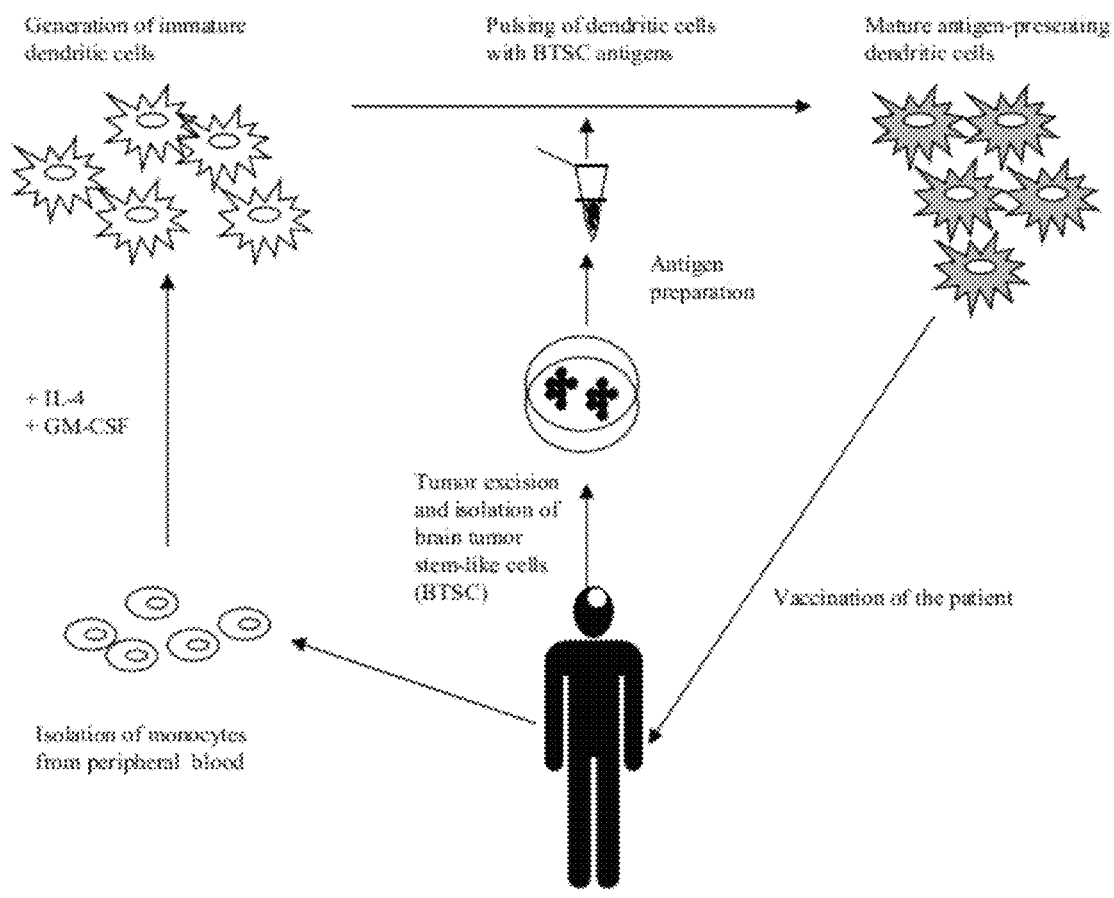
FIG. 1 is a schematic diagram of an exemplary process for vaccination of a patient with tumor antigen-pulsed dendritic cells. Monocytes are isolated from a patient and used to generate immature dendritic cells. After excision of a tumor or a portion of the tumor, brain tumor stem-like cells are isolated and used to prepare antigens for vaccination. The dendritic cells are pulsed with the antigens derived from the brain tumor stem-like cells. The mature antigen-presenting dendritic cells are then used to vaccinate the patient, providing an increased immune response against the tumor or residual tumor cells.

Described herein are methods of vaccinating a subject, e.g., to treat cancer (e.g., neural cancer, e.g., gliomas) with antigen-presenting cells ("APC"), e.g., dendritic cells ("DC"), that include antigens from cancer stem cells, e.g., presented on the surface of the antigen-presenting cells. Dendritic cells (e.g., autologous or allogeneic dendritic cells) are contacted with cancer stem cell antigens as a cell lysate, acid elution, cell extract, partially purified antigens, purified antigens, isolated antigens, partially purified peptides, purified peptides, isolated peptides, synthetic peptides, or a combination of two or more of the above. The antigen-presenting cells are then administered to a subject in need of cancer vaccination (e.g., a subject diagnosed with or at risk for cancer) to treat the cancer. FIG. 1 is a schematic diagram of an exemplary process for vaccination of a patient with cancer stem cell antigen-pulsed dendritic cells.

Cancer Stem Cells

The "cancer stem cell" hypothesis proposes that only a small portion of a tumor is represented by the "cancer stem cell," which allows the tumor to proliferate and self renew, and eventually differentiate into the phenotypically diverse and heterogeneous tumor cell population (Bjerkvig et al., Nat. Rev. Cancer, 5:899-904, 2005). Cancer stem cells can be isolated from any type of cancers, e.g., leukemias (Bonnet and Dick, Nat. Med., 3:730-737, 1997), breast cancers (Al-Hajj et al., Proc. Natl. Acad. Sci. USA, 100:3983-88, 2003), colon cancers (O'Brien et al., Nature, 445:106-110, 2007), and brain cancers (Singh et al., Nature, 432:396-401, 2004; Hemmati et al., Proc. Natl. Acad. Sci. USA, 100:15178-83, 2003; Singh et al., Cancer Res., 63:5821-28, 2003; Sanai et al., N. Engl. J. Med., 353:811-822, 2005; Tunici et al., Mol. Cancer, 3:25, 2004). Cancer stem cells are characterized by their ability to self-renew and proliferate, and recapitulate through differentiation the tumor from which it is isolated. Additionally, neural cancer stem cells form clonally derived neurospheres in culture.

Cancer stem cells can be isolated by dissociating tumor cells and culturing them under conditions that promote proliferation of stem cells (e.g., conditions that inhibit differentiation of the stem cells). Methods and conditions for isolating stem cells are known in the art. Exemplary methods and conditions can be found in U.S. Pat. Nos. 5,589,376, 5,643,741, 5,650,299, 5,824,489, 5,849,553, 5,928,947, 5,981,708, 6,337,184, 6,645,763, 6,800,790, 6,875,607, 6,984,522, 7,109,03, 7,115,267, and 7,115,360.

Additionally, cancer stem cells can be identified or isolated (e.g., isolated from non-stem tumor cells) on the basis of expression (e.g., nucleic acid or protein expression) of molecular markers, e.g., molecular markers described in the U.S. patents referred to in the above paragraph. Exemplary molecular markers include CD133, Bmi-1, Notch, Sonic hedgehog, and Wnt. Additionally, exemplary molecular markers of neural cancer stem cells include CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, and survivin.

Isolation or identification of cancer stem cells can be performed by standard means, e.g., cell sorting (e.g., fluorescence activated cell sorting (FACS) or magnetic cell sorting (MACS)).

Antigens

Antigenic peptides useful for loading DCs for vaccination are peptides that stimulate a T cell mediated immune response (e.g., a cytotoxic T cell response) by presentation to T cells on MHC molecules. Useful antigenic peptides and proteins include those derived from cancer stem cells (e.g., neural cancer stem cells, CD133+ tumor cells, or neurospheres derived from tumors). In some embodiments, the cancer stem cell antigens are presented as a lysate of the cancer stem cells. In other embodiments, the cancer stem cell antigens are obtained by acid elution of peptides presented on MHC molecules of the cancer stem cells. In an exemplary method, cancer stem cells are washed with an isotonic solution (e.g., Hank's buffered saline solution) to remove media components. The cells are then treated with acid (e.g., citrate phosphate buffer, pH 3.2) to dissociate peptides from surface MHCs, and the cells removed from the solution containing the soluble peptides. The acid-eluted cancer stem cell peptide antigens can be further purified (e.g., on a C18 column) and frozen for storage prior to use.

Specific antigens that can be used in the methods described herein include portions of the amino acid sequences of CD133, CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, and survivin that bind to MHC molecules and are presented to T cells. Peptides that bind to MHC class I molecules are generally 8-10 amino acids in length. Peptides that bind to MHC class II molecules are generally 13 amino acids or longer (e.g., 13-17 amino acids long).

CD133 is a 120 kDa, five-transmembrane domain glycoprotein expressed on neural and hematopoietic stem and progenitor cells (Yin et al., Blood, 90:5002-12, 1997). Table 1 provides an amino acid sequence of CD133 (also available in GenBank under accession number NP_006008.1, GI:5174387). The structure of CD133 includes an extracellular N-terminus, two short intracellular loops, two large extracellular loops, and an intracellular C-terminus (FIG. 18). Exemplary CD133 T cell epitopes include 8-10 or 13-20 contiguous amino acid residues of amino acid residues 325-350 of SEQ ID NO:53. An alternately spliced version of CD133 is described in Yu et al., J. Biol. Chem., 277:20711-16, 2002.

CD90 is a cell surface glycoprotein found on T cells and neurons. Table 1 provides an amino acid sequence of CD90 (also available in GenBank under accession number NP_006279.2, GI:19923362).

CD44 is a cell surface glycoprotein that may be involved in matrix adhesion. Table 1 provides an amino acid sequence of CD44 (also available in GenBank under accession number NP_000601.3, GI:48255935). Several isoforms of CD44 are produced, primarily by alternative splicing (see Marhaba et al., J. Mol. Histol., 35:211-31, 2004; Zoeller, Cancer Immunol. Immunother., 53:567-79, 2004).

CXCR4 is a chemokine receptor that has been found to be expressed in breast cancers (Muller et al., Nature, 410:50-56, 2001). Table 1 provides an amino acid sequence of CXCR4 (also available in GenBank under accession number NP_001008540.1, GI:56790927). An alternative spliced variant is available in GenBank under accession number NP_003458.1, GI:4503175.

Nestin is an intermediate filament protein expressed in neural progenitor cells (Dahlstrand et al., J. Cell Sci., 103:589-597, 1992). Table 1 provides an amino acid sequence of Nestin (also available in GenBank under accession number NP_006608.1, GI:38176300).

Musashi-1 (Msi1) is an RNA-binding protein expressed in neural progenitor cells (Good et al., Genomics, 52:382-384, 1998; Siddall et al., Proc. Nat. Acad. Sci. USA, 103:84-8407, 2006; Okano et al., Exp. Cell Res., 306:349-356, 2005). Table 1 provides an amino acid sequence of Musashi-1 (also available in GenBank under accession number NP_002433.1, GI:4505255).

Maternal embryonic leucine zipper kinase (MELK) is a protein kinase expressed in multiple cancers (Gray et al., Cancer Res., 65:9751-61, 2005). Table 1 provides an amino acid sequence of MELK (also available in GenBank under accession number NP_055606.1, GI:7661974).

GLI1 is a zinc-finger transcription factor upregulated in cancers, including gliomas (Kinzler et al., Science, 236:70-73, 1987; Kinzler et al., Nature, 332:371-374, 1988; Kasper et al., Eur. J. Cancer, 42:437-445, 2006). Table 1 provides an amino acid sequence of GLI1 (also available in GenBank under accession number NP_005260.1, GI:4885279).

PTCH1 is a transmembrane protein that is believed to function as a tumor suppressor (Katoh et al., Cancer Biol. Ther., 4:1050-54, 2005). Table 1 provides an amino acid sequence of PTCH1 (also available in GenBank under accession number NP_000255.2, GI:134254446). Five isoforms of PTCH1 are produced by alternative splicing (Nagao et al., Genomics, 85:462-71, 2005).

Bmi-1 is a polycomb ring finger protein involved in proliferation of progenitor cells (Lessard et al., Nature, 423:255-260, 2003; Park et al., Nature, 423:302-305, 2003; Molofsky et al., Nature, 425:962-967, 2003). Bmi-1 can play a role in the malignant transformation of the HOX A9/MEIS-induced murine leukemia model (Lessard et al., Nature, 423:255-260, 2003) as well as in tumors of neural origin (van Lohuizen et al., Nature, 353:353-355, 1991). Table 1 provides an amino acid sequence of Bmi-1 (also available in GenBank under accession number NP_005171.4, GI:27883842). Exemplary Bmi-1 T cell epitopes include TLQDIVYKL (SEQ ID NO:86), CLPSPSTPV (SEQ ID NO:87), VRYLETSKY (SEQ ID NO:88), KRYLRCPAA (SEQ ID NO:89), YEEEPLKDY (SEQ ID NO:90), and KEEVNDKRY (SEQ ID NO:91) (Steele et al., Br. J. Cancer 95:1202-11, 2006).

Phosphoserine phosphatase (PSP) is an enzyme that catalyzes the hydrolysis of O-phosphoserine. Table 1 provides an amino acid sequence of PSP (also available in GenBank under accession number NP_004568.2, GI:46249388).

Snail is a zinc-finger transcription factor and anti-apoptotic protein (Vega et al., Genes Dev., 18:1131-1143, 2004). Table 1 provides an amino acid sequence of Snail (also available in GenBank under accession number NP_005976.2, GI:18765741).

OCT4 is a POU homeodomain-containing transcription factor expressed in pluripotent cells (Nichols et al., Cell, 95:379-391, 1998). Table 1 provides an amino acid sequence of OCT4 (also available in GenBank under accession number NP_002692.2, GI:42560248). An alternate isoform of OCT4 is available in GenBank under accession number NP_976034.3, GI:116235491.

BCRP1 is an ATP-binding cassette (ABC) transporter protein involved in multidrug resistance of tumors (Doyle et al., Proc. Nat. Acad. Sci. USA, 95:1566570, 1998). Table 1 provides an amino acid sequence of BCRP1 (also available in GenBank under accession number NP_004818.2, GI:62526033).

MGMT is an O-6-methylguanine-DNA methyltransferase DNA-mismatch repair protein that can provide resistance to some methylating and chloroethylating agents, such as temozolomide (Rabik et al., Cancer Treat. Rev., 32:261-276, 2006; Cai et al., Cancer Res., 65:3319-27, 2005). Table 1 provides an amino acid sequence of MGMT (also available in GenBank under accession number NP_002403.1, GI:4505177).

BCL-2 is a mitochondrial anti-apoptotic protein correlated with chemotherapy resistant cancers and decreased overall survival (Campos et al., Blood, 81:3091-3096, 1993). Table 1 provides an amino acid sequence of BCL-2 (also available in GenBank under accession number NP_000624.2, GI:72198189). An alternatively spliced isoform of BCL-2 is available in GenBank under accession number NP_000648.2, GI:72198346.

FLIP is an anti-apoptotic protein (Irmler et al., Nature, 388:190-195, 1997). Table 1 provides an amino acid sequence of FLIP (also available in GenBank under accession number NP_003870.3, GI:21361769).

BCL-XL is an anti-apoptotic protein related to BCL-2, which may be involved in chemoresistance (Boise et al., Cell, 74:597-608, 1993; Andreeff et al., Leukemia, 13:1881-92, 1999). Table 1 provides an amino acid sequence of BCL-XL (also available in GenBank under accession number NP_612815.1, GI:20336335). Exemplary T cell epitopes of BCL-XL include Bcl-xL118-126 (TAYQSFEQV; SEQ ID NO:92), Bcl-xL173-182 (YLNDHLEPWI; SEQ ID NO:93), and Bcl-xL169-178 (WMATYLNDHL; SEQ ID NO:94) (Andersen et al., J. Immunol., 175:2709-14, 2005).

XIAP is a member of the inhibitor of apoptosis protein (IAP) family (Deveraux et al., Nature, 388:300-304, 1997). Table 1 provides an amino acid sequence of XIAP (also available in GenBank under accession number NP_001158.2, GI:32528299).

cIAP1 is a member of the IAP family of apoptosis inhibitors (Rothe et al., Cell, 83: 1243-1252, 1995; Liston et al., Nature, 379:349-353, 1996). Table 1 provides an amino acid sequence of cIAP1 (also available in GenBank under accession number NP_001157.1, GI:4502141).

cIAP2 is a member of the IAP family of apoptosis inhibitors (Liston et al., Nature, 379:349-353, 1996). Table 1 provides an amino acid sequence of cIAP2 (also available in GenBank under accession number NP_031490.1, GI:6680696).

NAIP is a member of the IAP family of apoptosis inhibitors (Roy et al., Cell, 80:167-178, 1995). Table 1 provides an amino acid sequence of NAIP (also available in GenBank under accession number NP_004527.2, GI:119393878). An alternatively spliced isoform of NAIP is available in GenBank under accession number NP_075043.1, GI:119393876.

Survivin is a member of the IAP family of apoptosis inhibitors (Li et al., Nature, 396:580-584, 1998). Table 1 provides an amino acid sequence of NAIP (also available in GenBank under accession number NP_001159.2, GI:59859878). Alternatively spliced isoforms of survivin have been identified (see Wheatley et al., Int. Rev. Cytol., 247:35-88, 2005; Noton et al., J. Biol. Chem., 281:1286-95, 2006; and Taubert et al., Oncogene, 24:5258-61, 2005). Sequences of exemplary alternative isoforms are available in GenBank under accession numbers NP_001012270.1, GI:59859880, and NP_001012271.1, GI:59859882. Exemplary T cell epitopes of survivin include Sur20-28 (STFKNWPFL; SEQ ID NO:95), Sur96-104 (LTLGEFLKL; SEQ ID NO:96), Sur133-141 (RAIEQLAAM; SEQ ID NO:97), and Sur126-135 (ETAKKVRRAI; SEQ ID NO:98) (Bachinsky et al., Cancer Immun., 5:6, 2005). Other exemplary T cell epitopes of survivin include Sur92-101 (QFEELTLGEF; SEQ ID NO:99), Sur54-62 (LAQCFFCFK; SEQ ID NO:100), Sur112-120 (KIAKETNNK; SEQ ID NO:101), Sur53-62 (DLAQCFFCFK; SEQ ID NO:102), Sur112-121 (KIAKETNNKK; SEQ ID NO:103), Sur18-28 (RISTFKNWPFL; SEQ ID NO:104), Sur86-96 (FLSVKKQFEEL; SEQ ID NO:105), and the modified peptides Sur92T2 (QTEELTLGEF; SEQ ID NO: 67), Sur93T2 (FTELTLGEF; SEQ ID NO: 68), Sur93S2 (FSELTLGEF; SEQ ID NO: 69), Sur38Y9 (MAEAGFIHY; SEQ ID NO: 70), Sur47Y10 (PTENEPDLAY; SEQ ID NO: 71), Sur5K9 (TLPPAWQPK; SEQ ID NO: 72), Sur54L2 (LLQCFFCFK; SEQ ID NO: 73), and Sur18K10 (RISTFKNWPK; SEQ ID NO: 74) (Reker et al., Cancer Biol. Ther., 3:173-179, 2004). Other exemplary T cell epitopes of survivin include ELTLGEFLKL (SEQ ID NO:75) and TLPPAWQPFL (SEQ ID NO: 76) (Schmitz et al., Cancer Res. 60:4845-4849, 2000). Additional survivin epitopes are described in Siegel et al., Br. J. Haematol., 122:911-914, 2003.

TABLE 1

Sequences of Human Antigens

| Antigen | Amino acid sequence |
|---|---|
| CD133 | MALVLGSLLLLGLCGNSFSGGQPSSTDAPKAWNYELPATNYETQDSHKAGPIGILFELVHI FLYVVQPRDFPEDTLRKFLQKAYESKIDYDKPETVILGLKIVYYEAGIILCCVLGLLFIIL MPLVGYFFCMCRCCNKCGGEMHQRQKENGPFLRKCFAISLLVICIIISIGIFYGFVANHQV RTRIKRSRKLADSNFKDLRTLLNETPEQIKYILAQYNTTKDKAFTDLNSINSVLGGGILDR LRPNIIPVLDEIKSMATAIKETKEALENMNSTLKSLHQQSTQLSSSLTSVKTSLRSSLNDP LCLVHPSSETCNSIRLSLSQLNSNPELRQLPPVDAELDNVNNVLRTDLDGLVQQGYQSLND IPDRVQRQTTTVVAGIKRVLNSIGSDIDNVTQRLPIQDILSAFSVYVNNTESYIHRNLPTL EEYDSYWWLGGLVICSLLTLIVIFYYLGLLCGVCGYDRHATPTTRGCVSNTGGVFLMVGVG LSFLFCWILMIIVVLTFVFGANVEKLICEPYTSKELFRVLDTPYLLNEDWEYYLSGKLFNK SKMKLTFEQVYSDCKKNRGTYGTLHLQNSFNISEHLNINEHTGSISSELESLKVNLNIFLL GAAGRKNLQDFAACGIDRMNYDSYLAQTGKSPAGVNLLSFAYDLEAKANSLPPGNLRNSLK RDAQTIKTIHQQRVLPIEQSLSTLYQSVKILQRTGNGLLERVTRILASLDFAQNFITNNTS SVIIEETKKYGRTIIGYFEHYLQWIEFSISEKVASCKPVATALDTAVDVFLCSYIIDPLNL FWEGIGKATVFLLPALIFAVKLAKYYRRMDSEDVYDDVETIPMKNMENGNNGYHKDHVYGI HNPVMTSPSQH (SEQ ID NO: 53) |
| CD90 | MNLAISIALLLTVLQVSRGQKVTSLTACLVDQSLRLDCRHENTSSSPIQYEFSLTRETKKH VLFGTVGVPEHTYRSRTNFTSKYNMKVLYLSAFTSKDEGTYTCALHHSGHSPPISSQNVTV LRDKLVKCEGISLLAQNTSWLLLLLLSLSLLQATDFMSL (SEQ ID NO: 54) |
| CD44 | MDKFWWHAAWGLCLVPLSLAQIDLNITCRFAGVEHVEKNGRYSISRTEAADLCKAFNSTLP TMAQMEKALSIGFETCRYGFIEGHVVIPRIHPNSICAANNTGVYILTSNTSQYDTYCFNAS APPEEDCTSVTDLPNAFDGPITITIVNRDGTRYVQKGEYRTNPEDIYPSNPTDDDVSSGSS SERSSTSGGYIFYTFSTVHPIPDEDSPWITDSTDRIPATTLMSTSATATETATKRQETWDW FSWLFLPSESKNHLHTTTQMAGTSSNTISAGWEPNEENEDERDRHLSFSGSGIDDDEDFIS STISTTPRAFDHTKQNQDWTQWNPSHSNPEVLLQTTTRMTDVDRNGTTAYEGNWNPEAHPP LIHHEHHEEEETPHSTSTIQATPSSTTEETATQKEQWFGNRWHEGYRQTPKEDSHSTTGTA AASAHTSHPMQGRTTPSPEDSSWTDFFNPISHPMGRGHQAGRRMDMDSSHSITLQPTANPN TGLVEDLDRTGPLSMTTQQSNSQSFSTSHEGLEEDKDHPTTSTLTSSNRNDVTGGRRDPNH SEGSTTLLEGYTSHYPHTKESRTFIPVTSAKTGSFGVTAVTVGDSNSNVNRSLSGDQDTFH PSGGSHTTHGSESDGHSHGSQEGGANTTSGPIRTPQIPEWLIILASLLALALILAVCIAVN SRRRCGQKKKLVINSGNGAVEDRKPSGLNGEASKSQEMVHLVNKESSETPDQFMTADETRN LQNVDMKIGV (SEQ ID NO: 55) |

TABLE 1-continued

Sequences of Human Antigens

| Antigen | Amino acid sequence |
|---|---|
| CXCR4 | MSIPLPLLQIYTSDNYTEEMGSGDYDSMKEPCFREENANFNKIFLPTIYSIIFLTGIVGNG<br>LVILVMGYQKKLRSMTDKYRLHLSVADLLFVITLPFWAVDAVANWYFGNFLCKAVHVIYTV<br>NLYSSVLILAFISLDRYLAIVHATNSQRPRKLLAEKVVYVGVWIPALLLTIPDFIFANVSE<br>ADDRYICDRFYPNDLWVVVFQFQHIMVGLILPGIVILSCYCIIISKLSHSKGHQKRKALKT<br>TVILILAFFACWLPYYIGISIDSFILLEIIKQGCEFENTVHKWISITEALAFFHCCLNPIL<br>YAFLGAKFKTSAQHALTSVSRGSSLKILSKGKRGGHSSVSTESESSSFHSS (SEQ ID NO: 56) |
| Nestin | MEGCMGEESFQMWELNRRLEAYLARVKALEEQNELLSAELGGLRAQSADTSWRAHADDELA<br>ALRALVDQRWREKHAAEVARDNLAEELEGVAGRCQQLRLARERTTEEVARNRRAVEAEKCA<br>RAWLSSQVAELERELEALRVAHEEERVGLNAQAACAPRCPAPPRGPPAPAPEVEELARRLG<br>EAWRGAVRGYQERVAHMETSLGQARERLGRAVQGAREGRLELQQLQAERGGLLERRAALEQ<br>RLEGRWQERLRATEKFQLAVEALEQEKQGLQSQIAQVLEGRQQLAHLKMSLSLEVATYRTL<br>LEAENSRLQTPGGGSKTSLSFQDPKLELQFPRTPEGRRLGSLLPVLSPTSLPSPLPATLET<br>PVPAFLKNQEFLQARTPTLASTPIPPTPQAPSPAVDAEIRAQDAPLSLLQTQGGRKQAPEP<br>LRAEARVAIPASVLPGPEEPGGQRQEASTGQSPEDHASLAPPLSPDHSSLEAKDGESGGSR<br>VFSICRGEGEGQIWGLVEKETAIEGKVVSSLQQEIWEEEDLNRKEIQDSQVPLEKETLKSL<br>GEEIQESLKTLENQSHETLERENQECPRSLEEDLETLKSLEKENKELLKDVEVVRPLEKEA<br>VGQLKPTGKEDTQTLQSLQKENQELMKSLEGNLETFLFPGTENQELVSSLQENLESLTALE<br>KENQEPLRSPEVGDEEALRPLTKENQEPLRSLEDENKEAFRSLEKENQEPLKTLEEEDQSI<br>VRPLETENHKSLRSLEEQDQETLRTLEKETQQRRRSLGEQDQMTLRPPEKVDLEPLKSLDQ<br>EIARPLENENQEFLKSLKEESVEAVKSLETEILESLKSAGQENLETLKSPETQAPLWTPEE<br>INQGAMNPLEKEIQEPLESVEVNQETFRLLEEENQESLRSLGAWNLENLRSPEEVDKESQR<br>NLEEEENLGKGEYQESLRSLEEEGQELPQSADVQRWEDTVEKDQELAQESPPGMAGVENED<br>EAELNLREQDGFTGKEEVVEQGELNATEEVWIPGEGHPESPEPKEQRGLVEGASVKGGAEG<br>LQDPEGQSQQVGAPGLQAPQGLPEAIEPLVEDDVAPGGDQASPEVMLGSEPAMGESAAGAE<br>PGPGQGVGGLGDPGHLTREEVMEPPLEEESLEAKRVQGLEGPRKDLEEAGGLGTEFSELPG<br>KSRDPWEPPREGREESEAEAPRGAEEAFPAETLGHTGSDAPSPWPLGSEEAEEDVPPVLVS<br>PSPTYTPILEDAPGPQPQAEGSQEASWGVQGRAEALGKVESEQEELGSGEIPEGPQEEGEE<br>SREESEEDELGETLPDSTPLGFYLRSPTSPRWDPTGEQRPPPQGETGKEGWDPAVLASEGL<br>EAPPSEKEEGEEGEEECGRDSDLSEEFEDLGTEAPFLPGVPGEVAEPLGQVPQLLLDPAAW<br>DRDGESDGFADEEESGEEGEEDQEEGREPGAGRWGPGSSVGSLQALSSSQRGEFLESDSVS<br>VSVPWDDSLRGAVAGAPKTALETESQDSAEPSGSEEESDPVSLEREDKVPGPLEIPSGMED<br>AGPGADIIGVNGQGPNLEGKSQHVNGGVMNGLEQSEEVGQGMPLVSEGDRGSPFQEEEGSA<br>LKTSWAGAPVHLGQGQFLKFTQREGDRESWSSGED (SEQ ID NO: 57) |
| Msi1 | METDAPQPGLASPDSPHDPCKMFIGGLSWQTTQEGLREYFGQFGEVKECLVMRDPLTKRSR<br>GFGFVTFMDQAGVDKVLAQSRHELDSKTIDPKVAFPRRAQPKMVTRTKKIFVGGLSVNTTV<br>EDVKQYFEQFGKVDDAMLMFDKTTNRHRGFGFVTFESEDIVEKVCEIHFHEINNKMVECKK<br>AQPKEVMSPTGSARGRSRVMPYGMDAFMLGIGMLGYPGFQATTYASRSYTGLAPGYTYQFP<br>EFRVERTPLPSAPVLPELTAIPLTAYGPMAAAAAAAVVRGTGSHPWTMAPPPGSTPSRTG<br>GFLGTTSPGPMAELYGAANQDSGVSSYISAASPAPSTGFGHSLGGPLIATAFTNGYH (SEQ ID NO: 58) |
| MELK | MKDYDELLKYYELHETIGTGGFAKVKLACHILTGEMVAIKIMDKNTLGSDLPRIKTEIEAL<br>KNLRHQHICQLYHVLETANKIFMVLEYCPGGELFDYIISQDRLSEEETRVVFRQIVSAVAY<br>VHSQGYAHRDLKPENLLFDEYHKLKLIDFGLCAKPKGNKDYHLQTCCGSLAYAAPELIQGK<br>SYLGSEADVWSMGILLYVLMCGFLPFDDDNVMALYKKIMRGKYDVPKWLSPSSILLLQQML<br>QVDPKKRISMKNLLNHPWIMQDYNYPVEWQSKNPFIHLDDDCVTELSVHHRNNRQTMEDLI<br>SLWQYDHLTATYLLLLAKKARGKPVRLRLSSFSCGQASATPFTDIKSNNWSLEDVTASDKN<br>YVAGLIDYDWCEDDLSTGAATPRTSQFTKYWTESNGVESKSLTPALCRTPANKLKNKENVY<br>TPKSAVKNEEYFMFPEPKTPVNKNQHKREILTTPNRYTTPSKARNQCLKETPIKIPVNSTG<br>TDKLMTGVISPERRCRSVELDLNQAHMEETPKRKGAKVFGSLERGLDKVITVLTRSKRKGS<br>ARDGPRRLKLHYNVTTTRLVNPDQLLNEIMSILPKKHVDFVQKGYTLKCQTQSDFGKVTMQ<br>FELEVCQLQKPDVVGIRRQRLKGDAWVYKRLVEDILSSCKV (SEQ ID NO: 59) |
| GLI1 | MENSMTPPPISSYGEPCCLRPLPSQGAPSVGTEGLSGPPFCHQANLMSGPHSYGPARETNS<br>CTEGPLFSSPRSAVKLTKKRALSISPLSDASLDLQTVIRTSPSSLVAFINSRCTSPGGSYG<br>HLSIGTMSPSLGFPAQMNHQKGPSPSFGVQPCGPHDSARGGMIPHPQSRGPFPTCQLKSEL<br>DMLVGKCREEPLEGDMSSPNSTGIQDPLLGMLDGREDLEREEKREPESVYETDCRWDGCSQ<br>EFDSQEQLVHHINSEHIHGERKEFVCHWGGCSRELRPFKAQYMLVVHMRRHTGEKPHKCTF<br>EGCRKSYSRLENLKTHLRSHTGEKPYMCEHEGCSKAFSNASDRAKHQNRTHSNEKPYVCKL<br>PGCTKRYTDPSSLRKHVKTVHGPDAHVTKRHRGDGPLPRAPSISTVEPKREREGGPIREES<br>RLTVPEGAMKPQPSPGAQSSCSSDHSPAGSAANTDSGVEMTGNAGGSTEDLSSLDEGPCIA<br>GTGLSTLRRLENLRLDQLHQLRPIGTRGLKLPSLSHTGTTVSRRVGPPVSLERRSSSSSSI<br>SSAYTVSRRSSLASPFPPPGSPPENGASSLPGLMPAQHYLLRARYASARGGGTSPTAASSLD<br>RIGGLPMPPWRSRAEYPGYNPNAGVTRRASDPAQAADRPAPARVQRFKSLGCVHTPPTVAG<br>GGQNFDPYLPTSVYSPQPPSITENAAMDARGLQEEPEVGTSMVGSGLNPYMDFPPTDTLGY<br>GGPEGAAAEPYGARGPGSLPLGPGPPTNYGPNPCPQQASYPDPTQETWGEFPSHSGLYPGP<br>KALGGTYSQCPRLEHYGQVQVKPEQGCPVGSDSTGLAPCLNAHPSEGPPHPQPLFSHYPQP<br>SPPQYLQSGPYTQPPPDYLPSEPRPCLDFDSPTHSTGQLKAQLVCNYVQSQQELLWEGGGR<br>EDAPAQEPSYQSPKFLGGSQVSPSRAKAPVNTYGPGFGPNLPNHKSGSYPTPSPCHENFVV<br>GANRASHRAAAPPRLLPPLPTCYGPLKVGGTNPSCGHPEVGRLGGGPALYPPPEGQVCNPL<br>DSLDLDNTQLDFVAILDEPQGLSPPPSHDQRGSSGHTPPPSGPPNMAVGNMSVLLRSLPGE<br>TEFLNSSA (SEQ ID NO: 60) |

TABLE 1-continued

Sequences of Human Antigens

| Antigen | Amino acid sequence |
|---|---|
| PTCH1 | MASAGNAAEPQDRGGGGSGCIGAPGRPAGGGRRRRTGGLRRAAAPDRDYLHRPSYCDAAFA<br>LEQISKGKATGRKAPLWLRAKFQRLLFKLGCYIQKNCGKFLVVGLLIFGAFAVGLKAANLE<br>TNVEELWVEVGGRVSRELNYTRQKIGEEAMFNPQLMIQTPKEEGANVLTTEALLQHLDSAL<br>QASRVHVYMYNRQWKLEHLCYKSGELITETGYMDQIIEYLYPCLIITPLDCFWEGAKLQSG<br>TAYLLGKPPLRWTNFDPLEFLEELKKINYQVDSWEEMLNKAEVGHGYMDRPCLNPADPDCP<br>ATAPNKNSTKPLDMALVLNGGCHGLSRKYMHWQEELIVGGTVKNSTGKLVSAHALQTMFQL<br>MTPKQMYEHFKGYEYVSHINWNEDKAAAILEAWQRTYVEVVHQSVAQNSTQKVLSFTTTL<br>DDILKSFSDVSVIRVASGYLLMLAYACLTMLRWDCSKSQGAVGLAGVLLVALSVAAGLGLC<br>SLIGISFNAATTQVLPFLALGVGVDDVFLLAHAFSETGQNKRIPFEDRTGECLKRTGASVA<br>LTSISNVTAFFMAALIPIPALRAFSLQAAVVVVFNFAMVLLIFPAILSMDLYRREDRRLDI<br>FCCFTSPCVSRVIQVEPQAYTDTHDNTRYSPPPPYSSHSFAHETQITMQSTVQLRTEYDPH<br>THVYYTTAEPRSEISVQPVTVTQDTLSCQSPESTSSTRDLLSQFSDSSLHCLEPPCTKWTL<br>SSFAEKHYAPPLLKPKAKVVVIFLFLGLLGVSLYGTTRVRDGLDLTDIVPRETREYDFIAA<br>QFKYFSFYNMYIVTQKADYPNIQHLLYDLHRSFSNVKYVMLEENKQLPKMWLHYFRDWLQG<br>LQDAFDSDWETGKIMPNNYKNGSDDGVLAYKLLVQTGSRDKPIDISQLTKQRLVDADGIIN<br>PSAFYIYLTAWVSNDPVAYAASQANIRPHRPEWVHDKADYMPETRLRIPAAEPIEYAQFPF<br>YLNGLRDTSDFVEAIEKVRTICSNYTSLGLSSYPNGYPFLFWEQYIGLRHWLLLFISVVLA<br>CTFLVCAVFLLNPWTAGIIVMVLALMTVELFGMMGLIGIKLSAVPVVILIASVGIGVEFTV<br>HVALAFLTAIGDKNRRAVLALEHMFAPVLDGAVSTLLGVLMLAGSEFDFIVRYFFAVLAIL<br>TILGVLNGLVLLPVLLSFFGPYPEVSPANGLNRLPTPSPEPPPSVVRFAMPPGHTHSGSDS<br>SDSEYSSQTTVSGLSEELRHYEAQQGAGGPAHQVIVEATENPVFAHSTVVHPESRHHPPSN<br>PRQQPHLDSGSLPPGRQGQQPRRDPPREGLWPPPYRPRRDAFEISTEGHGSPSNRARWGPR<br>GARSHNPRNPASTAMGSSVPGYCQPITTVTASASVTVAVHPPPVPGPGRNPRGGLCPGYPE<br>TDHGLFEDPHVPFHVRCERRDSKVEVIELQDVECEERPRGSSSN (SEQ ID NO: 61) |
| Bmi-1 | MHRTTRIKITELNPHLMCVLCGGYFIDATTIIECLHSFCKTCIVRYLETSKYCPICDVQVH<br>KTRPLLNIRSDKTLQDIVYKLVPGLFKNEMKRRRDFYAAHPSADAANGSNEDRGEVADEDK<br>RIITDDEIISLSIEFFDQNRLDRKVNKDKEKSKEEVNDKRYLRCPAAMTVMHLRKFLRSKM<br>DIPNTFQIDVMYEEEPLKDYYTLMDIAYIYTWRRNGPLPLKYRVRPTCKRMKISHQRDGLT<br>NAGELESDSGSDKANSPAGGIPSTSSCLPSPSTPVQSPHPQFPHISSTMNGTSNSPSGNHQ<br>SSFANRPRKSSVNGSSATSSG (SEQ ID NO: 62) |
| PSP | MVSHSELRKLFYSADAVCFDVDSTVIREEGIDELAKICGVEDAVSEMTRRAMGGAVPFKAA<br>LTERLALIQPSREQVQRLIAEQPPHLTPGIRELVSRLQERNVQVFLISGGFRSIVEHVASK<br>LNIPATNVFANRLKFYFNGEYAGFDETQPTAESGGKGKVIKLLKEKFHFKKIIMIGDGATD<br>MEACPPADAFIGFGGNVIRQQVKDNAKWYITDFVELLGELEE (SEQ ID NO: 63) |
| Snail | MPRSFLVRKPSDPNRKPNYSELQDSNPEFTFQQPYDQAHLLAAIPPPEILNPTASLPMLIW<br>DSVLAPQAQPIAWASLRLQESPRVAELTSLSDEDSGKGSQPPSPPSPAPSSFSSTSVSSLE<br>AEAYAAFPGLGQVPKQLAQLSEAKDLQARKAFNCKYCNKEYLSLGALKMHIRSHTLPCVCG<br>TCGKAFSRPWLLQGHVRTHTGEKPFSCPHCSRAFADRSNLRAHLQTHSDVKKYQCQACART<br>FSRMSLLHKHQESGCSGCPR (SEQ ID NO: 64) |
| OCT4 | MAGHLASDFAFSPPPGGGGDGPGGPEPGWVDPRTWLSFQGPPGGPGIGPGVGPGSEVWGIP<br>PCPPPYEFCGGMAYCGPQVGVGLVPQGGLETSQPEGEAGVGVESNSDGASPEPCTVTPGAV<br>KLEKEKLEQNPEESQDIKALQKELEQFAKLLKQKRITLGYTQADVGLTLGVLFGKVFSQTT<br>ICRFEALQLSFKNMCKLRPLLQKWVEEADNNENLQEICKAETLVQARKRKRTSIENRVRGN<br>LENLFLQCPKPTLQQISHIAQQLGLEKDVVRVWFCNRRQKGKRSSSDYAQREDFEAAGSPF<br>SGGPVSFPLAPGPHFGTPGYGSPHFTALYSSVPFPEGEAFPPVSVTTLGSPMHSN (SEQ<br>ID NO: 65) |
| BCRP1 | MSSSNVEVFIPVSQGNTNGFPATASNDLKAFTEGAVLSFHNICYRVKLKSGFLPCRKPVEK<br>EILSNINGIMKPGLNAILGPTGGGKSSLLDVLAARKDPSGLSGDVLINGAPRPANFKCNSG<br>YVVQDDVVMGTLTVRENLQFSAALRLATTMTNHEKNERINRVIQELGLDKVADSKVGTQFI<br>RGVSGGERKRTSIGMELITDPSILFLDEPTTGLDSSTANAVLLLLKRMSKQGRTIIFSIHQ<br>PRYSIFKLFDSLTLLASGRLMFHGPAQEALGYFESAGYHCEAYNNPADFFLDIINGDSTAV<br>ALNREEDFKATEIIEPSKQDKPLIEKLAEIYVNSSFYKETKAELHQLSGGEKKKKITVFKE<br>ISYTTSFCHQLRWVSKRSFKNLLGNPQASIAQIIVTVVLGLVIGAIYFGLKNDSTGIQNRA<br>GVLFFLTTNQCFSSVSAVELFVVEKKLFIHEYISGYYRVSSYFLGKLLSDLLPMRMLPSII<br>FTCIVYFMLGLKPKADAFFVMMFTLMMVAYSASSMALAIAAGQSVVSVATLLMTICFVFMM<br>IFSGLLVNLTTIASWLSWLQYFSIPRYGFTALQHNEFLGQNFCPGLNATGNNPCNYATCTG<br>EEYLVKQGIDLSPWGLWKNHVALACMIVIFPLTIAYLKLLFLKKYS (SEQ ID NO: 66) |
| MGMT | MDKDCEMKRTTLDSPLGKLELSGCEQGLHEIKLLGKGTSAADAVEVPAPAAVLGGPEPLMQ<br>CTAWLNAYFHQPEAIEEFPVPALHHPVFQQESFTRQVLWKLLKVVKFGEVISYQQLAALAG<br>NPKAARAVGGAMRGNPVPILIPCHRVVCSSGAVGNYSGGLAVKEWLLAHEGHRLGKPGLGG<br>SSGLAGAWLKGAGATSGSPPAGRN (SEQ ID NO: 77) |
| BCL-2 | MAHAGRTGYDNREIVMKYIHYKLSQRGYEWDAGDVGAAPPGAAPAPGIFSSQPGHTPHPAA<br>SRDPVARTSPLQTPAAPGAAAGPALSPVPPVVHLTLRQAGDDFSRRYRRDFAEMSSQLHLT<br>PFTARGRFATVVEELFRDGVNWGRIVAFFEFGGVMCVESVNREMSPLVDNIALWMTEYLNR<br>HLHTWIQDNGGWDAFVELYGPSMRPLFDFSWLSLKTLLSLALVGACITLGAYLGHK (SEQ<br>ID NO: 78) |

TABLE 1-continued

Sequences of Human Antigens

Antigen  Amino acid sequence

FLIP     MSAEVIHQVEEALDTDEKEMLLFLCRDVAIDVVPPNVRDLLDILRERGKLSVGDLAELLYR
         VRRFDLLKRILKMDRKAVETHLLRNPHLVSDYRVLMAEIGEDLDKSDVSSLIFLMKDYMGR
         GKISKEKSFLDLVVELEKLNLVAPDQLDLLEKCLKNIHRIDLKTKIQKYKQSVQGAGTSYR
         NVLQAAIQKSLKDPSNNFRLHNGRSKEQRLKEQLGAQQEPVKKSIQESEAFLPQSIPEERY
         KMKSKPLGICLIIDCIGNETELLRDTFTSLGYEVQKFLHLSMHGISQILGQFACMPEHRDY
         DSFVCVLVSRGGSQSVYGVDQTHSGLPLHHIRRMFMGDSCPYLAGKPKMFFIQNYVVSEGQ
         LENSSLLEVDGPAMKNVEFKAQKRGLCTVHREADFEWSLCTADMSLLEQSHSSPSLYLQCL
         SQKLRQERKRPLLDLHIELNGYMYDWNSRVSAKEKYYVWLQHTLRKKLILSYT (SEQ ID
         NO: 79)

BCL-XL   MSQSNRELVVDFLSYKLSQKGYSWSQFSDVEENRTEAPEGTESEMETPSAINGNPSWHLAD
         SPAVNGATGHSSSLDAREVIPMAAVKQALREAGDEFELRYRRAFSDLTSQLHITPGTAYQS
         FEQVVNELFRDGVNWGRIVAFFSEGGALCVESVDKEMQVLVSRIAAWMATYLNDHLEPWIQ
         ENGGWDTFVELYGNNAAAESRKGQERFNRWFLTGMTVAGVVLLGSLFSRK (SEQ ID
         NO: 80)

XIAP     MTENSFEGSKTCVPADINKEEEFVEEFNRLKTFANFPSGSPVSASTLARAGFLYTGEGDTV
         RCFSCHAAVDRWQYGDSAVGRHRKVSPNCRFINGFYLENSATQSTNSGIQNGQYKVENYLG
         SRDHFALDRPSETHADYLLRTGQVVDISDTIYPRNPAMYSEEARLKSFQNWPDYAHLTPRE
         LASAGLYYTGIGDQVQCFCCGGKLKNWEPCDRAWSEHRRHFPNCRFVLGRNLNIRSESDAV
         SSDRNFPNSTNLPRNPSMADYEARIFTGTWIYSVNKEQLARAGFYALGEGDKVKCFHCGG
         GLTDWKPSEDPWEQHAKWYPGCKYLLEQKGQEYINNIHLTHSLEECLVRTTEKTPSLTRRI
         DDTIFQNPMVQEAIRMGESFKDIKKIMEEKIQISGSNYKSLEVLVADLVNAQKDSMQDESS
         QTSLQKEISTEEQLRRLQEEKLCKICMDRNIAIVEVPCGHLVTCKQCAEAVDKCPMCYTVI
         TFKQKIFMS (SEQ ID NO: 81)

cIAP1    MHKTASQRLFPGPSYQNIKSIMEDSTILSDWTNSNKQKMKYDFSCELYRMSTYSTFPAGVP
         VSERSLARAGFYYTGVNDKVKCFCCGLMLDNWKLGDSPIQKHKQLYPSCSFIQNLVSASLG
         STSKNTSPMRNSFAHSLSPTLEHSSLFSGSYSSLSPNPLNSRAVEDISSSRTNPYSYAMST
         EEARFLTYHMWPLTELSPSELARAGFYYIGPGDRVACFACGGKLSNWEPKDDAMSEHRRHF
         PNCPFLENSLETLRFSISNLSMQTHAARMRTFMYWPSSVPVQPEQLASAGFYYVGRNDDVK
         CFCCDGGLRCWESGDDPWVEHAKWFPRCEFLIRMKGQEFVDEIQGRYPHLLEQLLSTSDTT
         GEENADPPIIHFGPGESSSEDAVMMNTPVVKSALEMGFNRDLVKQTVQSKILTTGENYKTV
         NDIVSALLNAEDEKREEEKEKQAEEMASDDLSLIRKNRMALFQQLTCVLPILDNLLKANVI
         NKQEHDIIKQKTQIPLQARELIDTILVKGNAAANIFKNCLKEIDSTLYKNLFVDKNMKYIP
         TEDVSGLSLEEQLRRLQEERTCKVCMDKEVSVVFIPCGHLVVCQECAPSLRKCPICRGIIK
         GTVRTFLS (SEQ ID NO: 82)

cIAP2    MVQDSAFLAKLMKSADTFELKYDFSCELYRLSTYSAFPRGVPVSERSLARAGFYYTGANDK
         VKCFCCGLMLDNWKQGDSPMEKHRKLYPSCNEVQTLNPANSLEASPRPSLPSTAMSTMPLS
         FASSENTGYFSGSYSSFPSDPVNFRANQDCPALSTSPYHFAMNTEKARLLTYETWPLSFLS
         PAKLAKAGFYYIGPGDRVACFACDGKLSNWERKDDAMSEHQRHFPSCPFLKDLGQSASRYT
         VSNLSMQTHAARIRTFSNWPSSALVHSQELASAGFYYTGHSDDVKCFCCDGGLRCWESGDD
         PWVEHAKWFPRCEYLLRIKGQEFVSQVQAGYPHLLEQLLSTSDSPEDENADAAIVHFGPGE
         SSEDVVMMSTPVVKAALEMGFSRSLVRQTVQRQILATGENYRTVSDLVIGLLDAEDEMREE
         QMEQAAEEEESDDLALIRKNKMVLFQHLTCVTPMLYCLLSARAITEQECNAVKQKPHTLQA
         STLIDTVLAKGNTAATSFRNSLREIDPALYRDIFVQQDIRSLPTDDIAALPMEEQLRKLQE
         ERMCKVCMDREVSIVFIPCGHLVVCKDCAPSLRKCPICRGTIKGTVRTFLS (SEQ ID
         NO: 83)

NAIP     MATQQKASDERISQFDHNLLPELSALLGLDAVQLAKELEEEEQKERAKMQKGYNSQMRSEA
         KRLKTFVTYEPYSSWIPQEMAAAGFYFTGVKSGIQCFCCSLILFGAGLTRLPIEDHKRFHP
         DCGFLLNKDVGNIAKYDIRVKNLKSRLRGGKMRYQEEEARLASFRNWPFYVQGISPCVLSE
         AGFVFTGKQDTVQCFSCGGCLGNWEEGDDPWKEHAKWFPKCEFLRSKKSSEEITQYIQSYK
         GFVDITGEHFVNSWVQRELPMASAYCNDSIFAYEELRLDSFKDWPRESAVGVAALAKAGLF
         YTGIKDIVQCFSCGGCLEKWQEGDDPLDDHTRCFPNCPFLQNMKSSAEVTPDLQSRGELCE
         LLETTSESNLEDSIAVGPIVPEMAQGEAQWFQEAKNLNEQLRAAYTSASFRHMSLLDISSD
         LATDHLLGCDLSIASKHISKPVQEPLVLPEVFGNLNSVMCVEGEAGSGKTVLLKKIAFLWA
         SGCCPLLNRFQLVFYLSLSSTRPDEGLASIICDQLLEKEGSVTEMCVRNIIQQLKNQVLFL
         LDDYKEICSIPQVIGKLIQKNHLSRTCLLIAVRTNRARDIRRYLETILEIKAFPFYNTVCI
         LRKLFSHNMTRLRKFMVYFGKNQSLQKIQKTPLFVAAICAHWFQYPFDPSFDDVAVFKSYM
         ERLSLRNKATAEILKATVSSCGELALKGFFSCCFENDDDLAEAGVDEDEDLTMCLMSKFT
         AQRLRPFYRFLSPAFQEFLAGMRLIELLDSDRQEHQDLGLYHLKQINSPMMTVSAYNNFLN
         YVSSLPSTKAGPKIVSHLLHLVDNKESLENISENDDYLKHQPEISLQMQLLRGLWQICPQA
         YFSMVSEHLLVLALKTAYQSNTVAACSPFVLQFLQGRTLTLGALNLQYFFDHPESLSLLRS
         IHFPIRGNKTSPRAHFSVLETCFDKSQVPTIDQDYASAFEPMNEWERNLAEKEDNVKSYMD
         MQRRASPDLSTGYWKLSPKQYKIPCLEVDVNDIDVVGQDMLEILMTVFSASQRIELHLNHS
         RGFIESIRPALELSKASVTKCSISKLELSAAEQELLLTPSLESLEVSGTIQSQDQIFPNL
         DKFLCLKELSVDLEGNINVFSVIPEEFPNFHHMEKLLIQISAEYDPSKLVKLIQNSPNLHV
         FHLKCNFFSDFGSLMTMLVSCKKLTEIKFSDSFFQAVPPFVASLPNFISLKILNLEGQQFPD
         EETSEKFAYILGSLSNLEELILPTGDGIYRVAKLIIQQCQQLHCLRVLSFFKTLNDDSVVE
         IAKVAISGGFQKLENLKLSINHKITEEGYRNFFQALDNMPNLQELDISRHFTECIKAQATT
         VKSLSQCVLRLPRLIRLNMLSWLLDADDIALLNVMKERHPQSKYLTILQKWILPFSPIIQK
         (SEQ ID NO: 84)

TABLE 1-continued

Sequences of Human Antigens

Antigen Amino acid sequence

Survivin MGAPTLPPAWQPFLKDHRISTFKNWPFLEGCACTPERMAEAGFIHCPTENEPDLAQCFFCF
KELEGWEPDDDPIEEHKKHSSGCAFLSVKKQFEELTLGEFLKLDRERAKNKIAKETNNKKK
EFEETAEKVRRAIEQLAAMD (SEQ ID NO: 85)

T cell epitopes can be identified by a number of different methods. Naturally processed MHC epitopes can be identified by mass spectrophotometric analysis of peptides eluted from antigen-loaded APC (e.g., APC that have taken up antigen, or that have been engineered to produce the protein intracellularly). After incubation at 37° C., cells are lysed in detergent and the MHC protein is purified (e.g., by affinity chromatography). Treatment of the purified MHC with a suitable chemical medium (e.g., under acidic conditions) results in the elution of peptides from the MHC. This pool of peptides is separated and the profile compared with peptides from control APC treated in the same way. The peaks unique to the protein expressing/fed cells are analyzed (for example by mass spectrometry) and the peptide fragments identified. This protocol identifies peptides generated from a particular antigen by antigen processing.

Alternatively, epitopes can be identified by screening a synthetic library of peptides that overlap and span the length of the antigen in an in vitro assay. For example, peptides that are 9 amino acids in length and which overlap by 5 amino acids may be used. The peptides are tested in an antigen presentation system that includes antigen presenting cells and T cells. T cell activation in the presence of APCs presenting the peptide can be measured (e.g., by measuring T cell proliferation or cytokine production) and compared to controls, to determine whether a particular epitope is recognized by the T cells.

T cell epitopes can be predicted in silico, e.g., using the methods described in Parker et al., J. Immunol., 152:163, 1994 and Rammensee et al., Irnmunogenet., 50:213-219, 1999.

Antigenic peptides can be obtained by chemical synthesis using a commercially available automated peptide synthesizer. Synthetic peptides can be precipitated and further purified, for example by high performance liquid chromatography (HPLC). Alternatively, isolated peptides can be obtained by purification and/or recombinant methods using host cell and vector expression systems.

Preparation of Antigen Presenting Cells

Antigen presenting cells (APC), such as DCs, suitable for administration to subjects (e.g., glioma patients) can be isolated or obtained from any tissue in which such cells are found, or may be otherwise cultured and provided using standard techniques. Methods of preparing antigen presenting cells are well-known to those of skill in the art. Mature dendritic cells are typically identified as having the following cell surface marker phenotype: MAG3$^-$, CD80$^+$, CD86$^+$, CD40$^{low}$, CD54$^+$, MHC Class I and MHC Class II, and are capable of FITC-dextran uptake.

APCs (e.g., DCs) can be found, by way of example, in the bone marrow or PBMCs of a mammal, in the spleen of a mammal or in the skin of a mammal (i.e., Langerhan's cells, which possess certain qualities similar to that of DC, may be found in the skin). For instance, bone marrow can be harvested from a mammal and cultured in a medium that promotes the growth of DCs. GM-CSF, IL-4 and/or other cytokines (e.g., TNF-α), growth factors and supplements may be included in this medium.

After a suitable amount of time in culture in medium containing appropriate cytokines (e.g., time suitable to expand and differentiate the DCs into mature DCs, e.g., 2, 4, 6, 8, 10, 12, or 15 days), clusters of DCs are cultured in the presence of a sufficient number of antigens of interest (e.g., in the presence of cancer stem cell lysate, acid eluted peptides of cancer stem cells, peptides of CD133, CD90, CD44, CXCR4, Nestin, Musashi-1 (Msi1), maternal embryonic leucine zipper kinase (MELK), GLI1, PTCH1, Bmi-1, phosphoserine phosphatase (PSP), Snail, OCT4, BCRP1, MGMT, Bcl-2, FLIP, BCL-XL, XIAP, cIAP1, cIAP2, NAIP, or survivin, or a combination of two or more of the above antigens) and harvested for use in a cancer vaccine. For example, peptide antigens can be added to the culture medium at a concentration of about 1.0 to 50, e.g., 5, 10, 15, 20, or 30 µg/ml (per antigen).

Alternately, or in combination, antigens can be transgenically expressed in DCs, e.g., by transfection of nucleic acids encoding one or more of the antigens or portions of antigens.

In one exemplary method, APCs are isolated from a subject (e.g., a human) according to the following exemplary procedure. Mononuclear cells are isolated from blood using leukapheresis (e.g., using a COBE Spectra Apheresis System). The mononuclear cells are allowed to become adherent by incubation in tissue culture flasks for 2 hours at 37° C. Nonadherent cells are removed by washing. Adherent cells are cultured in medium supplemented with granulocyte macrophage colony stimulating factor (GM-CSF) and interleukin-4 (IL-4) for five days. On day five, TNF-α is added to the culture medium for another 3-4 days. On day 8 or 9, cells are harvested and washed, and incubated with peptide antigens for 16-20 hours on a tissue rotator. Peptide antigens are added to the cultures at a concentration of ~10 µg/ml (per antigen).

Various other methods can be used to isolate the APCs, as would be recognized by one of skill in the art. DCs occur in low numbers in all tissues in which they reside, making isolation and enrichment of DCs a requirement. Any of a number of procedures entailing repetitive density gradient separation, fluorescence activated cell sorting techniques, positive selection, negative selection or a combination thereof are routinely used to obtain enriched populations or isolated DCs. Guidance on such methods for isolating DCs can be found in O'Doherty et al., J. Exp. Med., 178:1067-78, 1993; Young and Steinman, J. Exp. Med., 171:1315-32, 1990; Freudenthal and Steinman, Proc. Nat. Acad. Sci. USA, 57:7698-7702, 1990; Macatonia et al., 67:285-289, 1989; Markowicz and Engleman, J. Clin. Invest., 85:955-961, 1990; Mehta-Damani et al., J. Immunol., 153:996-1003, 1994; and Thomas et al., J. Immunol., 151:6840-6852, 1993. One method for isolating DCs from human peripheral blood is described in U.S. Pat. No. 5,643,786. Methods of producing DCs from embryonic stem cells are described in U.S. Pat. No. 7,247,480.

Administration of Cancer Vaccines

The APC-based cancer vaccine may be delivered to a recipient by any suitable delivery route, which can include injection, infusion, inoculation, direct surgical delivery, or any combination thereof. In some embodiments, the cancer vaccine is administered to a human in the deltoid region or axillary region. In some embodiments, the vaccine is administered to a subject locally to the site of a tumor, within the tumor, or to an area from which a tumor has been surgically resected.

An appropriate carrier for administering the cells may be selected by one of skill in the art by routine techniques. For example, the pharmaceutical carrier can be a buffered saline solution, e.g., cell culture media.

The quantity of APC appropriate for administration to a patient as a cancer vaccine to effect the methods of the present invention and the most convenient route of such administration may be based upon a variety of factors, as may the formulation of the vaccine itself. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in connection with an overall treatment regimen. Notwithstanding the variety of factors one should consider in implementing the methods of the present invention to treat a disease condition, a mammal can be administered with from about $10^5$ to about $10^9$ APC (e.g., $10^7$ APC) in from about 0.05 mL to about 5 mL solution (e.g., saline) in a single administration. Additional administrations can be carried out, depending upon the above-described and other factors, such as the severity of tumor pathology. In one embodiment, from about one to about five administrations of about $10^6$ APC is performed at two-week intervals.

DC vaccination can be accompanied by other treatments. For example, a patient receiving DC vaccination may also be receiving chemotherapy, radiation, and/or surgical therapy concurrently. Methods of treating cancer using DC vaccination in conjunction with chemotherapy are described in Wheeler et al., U.S. Pat. Pub. No. 2007/0020297. In some embodiments, a patient receiving DC vaccination has already received chemotherapy, radiation, and/or surgical treatment for the cancer. In one embodiment, a patient receiving DC vaccination is treated with a COX-2 inhibitor, as described in Yu and Akasaki, WO 2005/037995.

Pharmaceutical Compositions

In various embodiments, the present invention provides pharmaceutical compositions including a pharmaceutically acceptable excipient along with a therapeutically effective amount of the inventive vaccine comprising dendritic cells pulsed with cancer stem cell antigens as described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, transmucosal, transdermal, or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins PA, USA) (2000).

Kits

Kits to treat cancer are also contemplated. The kits are useful for practicing the inventive method of treating cancer with a vaccine comprising dendritic cells pulsed with cancer stem cell antigens as described herein. The kit is an assemblage of materials or components, including at least one of the inventive compositions. Thus, in some embodiments the kit contains a composition including a vaccine comprising dendritic cells pulsed with cancer stem cell antigens as described herein.

The exact nature of the components configured in the inventive kit depends on its intended purpose. For example, some embodiments are configured for the purpose of treating a particular cancer. In one embodiment, the kit is configured for the purpose of treating brain tumors. In one particular embodiment, the brain tumor is a glioma. In another embodiment, the brain tumor is GBM. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as induction of an immune response against a tumor, to treat a cancer. For example, the instructions may comprise instructions to administer a vaccine comprising dendritic cells pulsed with cancer stem cell antigens to the patient.

Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in cancer treatments or in vaccinations. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing for example, a vaccine comprising dendritic cells pulsed with cancer stem cell antigens as described herein. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

The 9L Gliosarcoma Cell Line Contains Self-Renewing Cells

Figure 2:
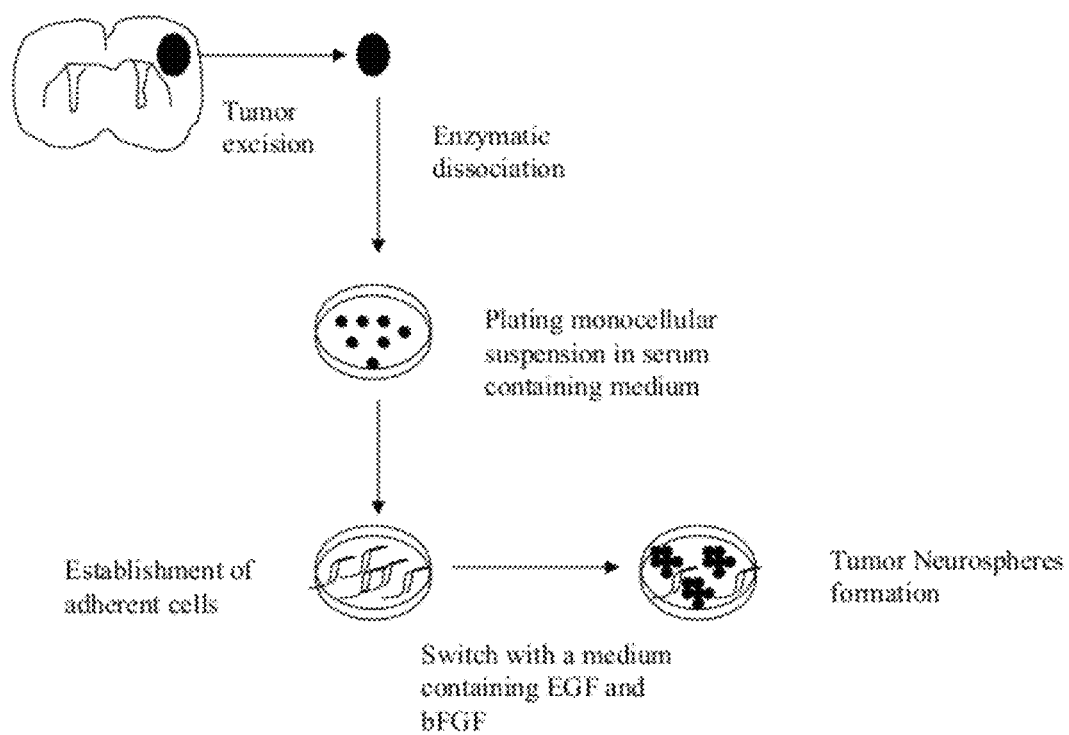
FIG. 2 is a schematic diagram depicting an exemplary method of isolation and generation of tumor neurospheres.

To determine if a population of self-renewing stem cells exist within the phenotypically heterogeneous 9L gliosarcoma tumor, the cells were grown as monolayers in the presence of 10% FBS and subsequently grew them in serum free media containing mitogens. A schematic diagram of culturing of tumor stem cells is presented in FIG. 2. 9L gliosarcomas were resuspended in Dulbecco's modified Eagle's medium/F-12 medium containing 10% fetal bovine serum (FBS) and plated at a density of $1 \times 10^6$ live cells per 75 $cm^2$ flask. The cells attached and grew as monolayers and were passaged upon confluency. Spheres were derived by placing the 9L gliosarcomas cells grown as monolayers into a defined serum-free NSC medium (Reynolds et al., J. Neurosci., 12: 4565-74, 1992; Reynolds et al., Science, 255:1707-10, 1992) consisting of Dulbecco's modified Eagle's medium/F-12 medium supplemented with 20 ng/mL of both epidermal growth factor (EGF; Peprotech, Rocky Hill, N.J.) and basic fibroblast growth factor (bFGF; Peprotech, Rocky Hill, N.J.). Cells were fed every 2 days by adding fresh NSC media supplemented with growth factors. After primary spheres formed and reached 10-200 cells per sphere, the cells were harvested, dissociated into single cells using trypsin and EDTA (GIBCO BRL) and mechanical pipetting, strained through a cell strainer, and plated at a clonal density of 1,000 cells/mL in neurosphere-conditioned medium to generate clonally derived subspheres (Geschwind et al., Neuron, 29:325-339, 2001; Groszer et al., Science, 294: 2186-89, 2001). The cells were fed every 2 days by adding fresh NSC media supplemented with mitogens. Cells and subsequent spheres were observed daily for 18 days, and passaged into fresh media. Subspheres ranging from approximately 15 cells to 40 cells were evident after 18 days and displayed the self-renewing and proliferative capacity of the 9L spheres.

Figure 8A:
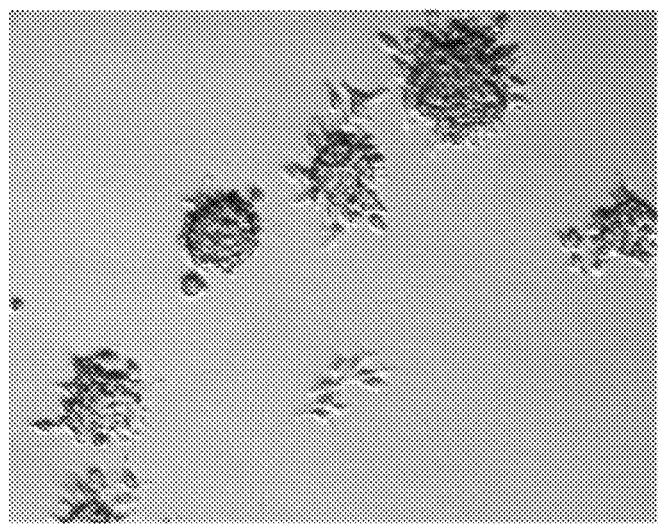
FIGS. 8A-8C are micrographs depicting primary culture of adult human glioblastoma cells. (8A) Neurosphere-like tumor cells were found in glioblastoma primary cell culture in F-12/DMEM 10% FBS medium. Scale bar=200 µm. (8B) Neurosphere derived from a single isolated CD133$^+$ cell cultured in serum free medium with EGF/FGF. Scale bar=200 µm. (8C) CD133 expression on a neurosphere derived from a single isolated CD133$^+$ cell in serum free medium with EGF/FGF. Staining indicates CD133 expression. Scale bar=50 µm.

Subtle differences were observed in surface adhesion properties between the two cell populations when using different coating solutions. It was found that poly-L-lysine proved less effective in binding to neurospheres than did laminin. Even after 2 days, only a small portion of the cells adhered (~5%). However, when neurospheres were allowed to adhere to chamber slides coated with laminin, nearly all the cells (~70%) adhered within the first 3 hours. As a consequence, poly-L-lysine was not used as an adhesive substrate in further studies. A similar trend was observed when comparing adhesion of monolayers to chamber slides coated with either poly-L-lysine or laminin—cellular morphology was more apparent in monolayers grown on laminin coated chamber slides within a 6 hour time period. Furthermore, a distinct morphological characteristic was apparent in the differentiated neurospheres, where arms of differentiated cells originating from one neurosphere homed to arms formed by another nearby neurosphere (FIG. 8A). These examples of extracellular adhesion and cellular homing can be used to distinguish cancer stem-like cells (CSLCs) from non-CSLCs within a tumor.

Example 2

9L Neurospheres Express NSC Markers and can Generate Both Neuronal and Glial Cells in Culture To determine the expression of markers for stem cells, neurospheres were immunostained for NSC markers nestin and Sox2. Neurospheres were also stained for the lineage markers for astrocytes, GFAP, neurons, beta-tubulin III and MAP2, and oligodendrocytes, myelin/oligodendrocyte. Cells in the outer region of the neurosphere labeled for nestin, while cells throughout the neurosphere were labeled for Sox2. A large number of cells within the tumor spheres were also found to be positive for the lineage marker GFAP, while relatively few cells expressed the neuronal lineage markers β-tubulin III, MAP2, and myelin/oligodendrocyte.

To test whether spheres have multipotent capabilities and produce progenies of different lineages, spheres were seeded into chamber slides (Lab-TekII, Nalge Nunc International) for differentiation assay. The cells were grown for 14 days in medium devoid of growth factors bFGF and EGF but permissive for differentiation, and processed for immunocytochemistry as described below. The medium included Dulbecco's modified Eagle's medium/F-12 medium containing 10% fetal bovine serum (FBS).

To examine the expression of NSC markers and lineage markers, immuncyto- and immunohistochemical staining was performed. For staining of differentiated spheres, spheres and 9L monolayers, cells growing in chamber slides were fixed with 4% paraformaldehyde for 15 minutes at 4° C., treated with 5% NHS (normal horse serum)/0.1% Triton-X, and then stained with the following antibodies: rabbit anti-nestin (1:200, Chemicon), rabbit anti-Sox2 (1:1,000, Chemicon), rabbit anti-MAP2 (1:1,000, Sigma), mouse anti-β-tubulin III (1:200, Chemicon), rabbit anti-GFAP (1:1000, Chemicon), mouse anti-myelin/oligodendrocyte (1:1,000, Chemicon). The primary antibodies were detected with Cy3 or FITC-conjugated anti-mouse or anti-rabbit IgG antibody (1:200, Jackson Immuno Research). The cells were counterstained with 4',6-diamidino-2-phenylindole (DAPI; Vector Laboratories) to identify all nuclei. The stained sections were examined and photographed using a QED cell scanner program and Nikon Eclipse TE2000-E microscope, and analyzed using Image J (NIH). For immunostaining of spheres, the spheres where allowed to adhere to precoated (with laminin) chamber slides for 3 hours before fixation, while monolayers were allowed to adhere overnight in non-fixed chamber slides.

Figure 3A:
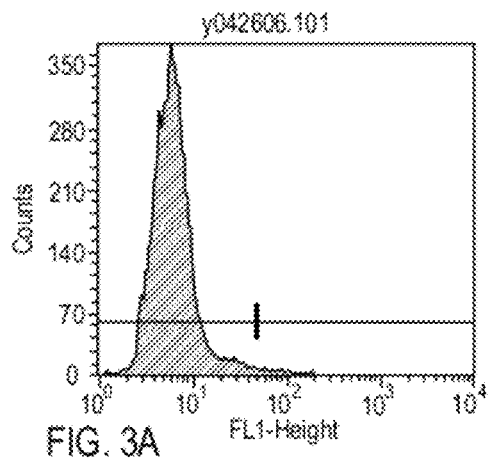
FIGS. 3A-3F are a set of histograms depicting FACS analysis of neurospheres differentiated for 2 weeks. Neurospheres differentiated for 2 weeks show (3B) 96% of cells positive for the astrocyte marker GFAP; (3C) 88% of cells positive for the NSC marker nestin; (3D) 29% of cells positive for the neuronal marker MAP2; (3E) 0% of cells positive for the neuronal marker beta-tubulin III; (3F) 6% of cells positive for the oligodendrocyte marker myelin/oligodendroctye. The samples were compared to a negative control as shown (3A).
Figure 3B:
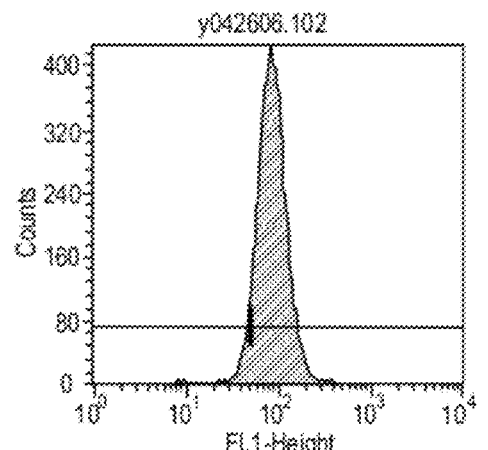
Figure 3C:
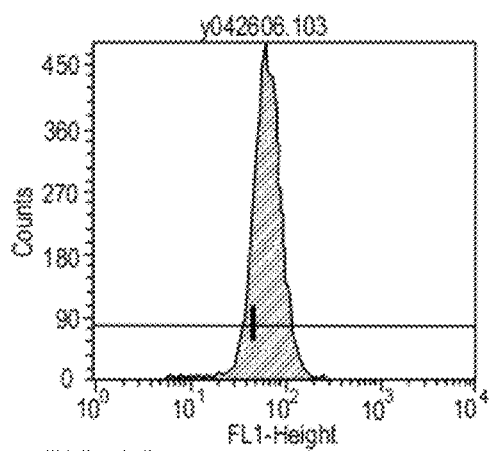
Figure 3D:
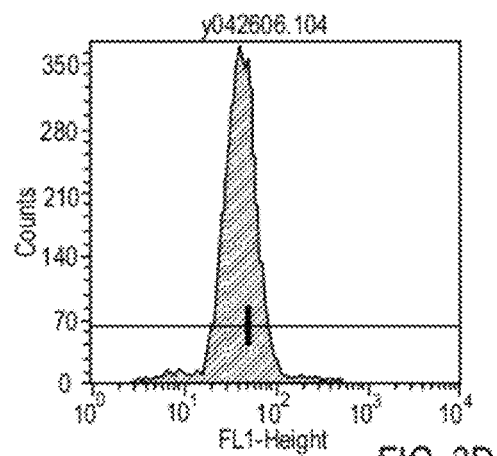
Figure 3E:
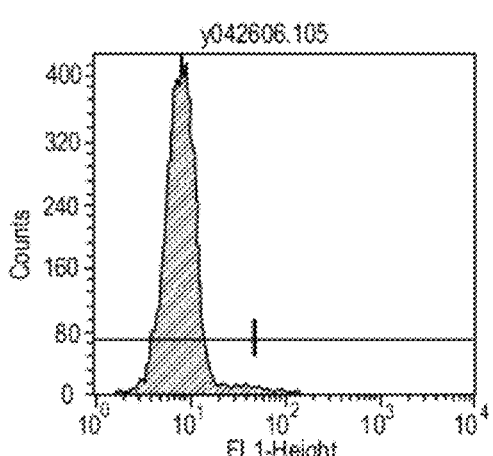
Figure 3F:
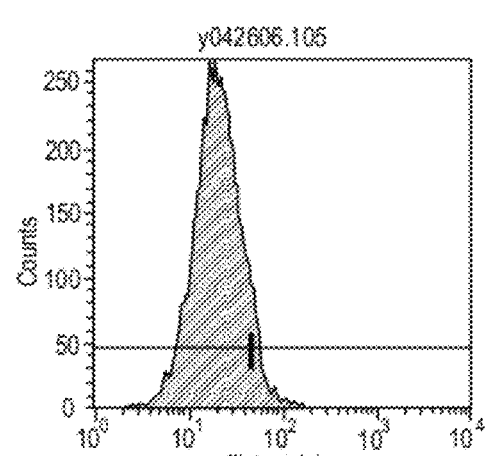

Cells stained positive for the NSC markers nestin and Sox2, as well as the lineage markers for astrocytes, GFAP, neurons, MAP2, and oligodendrocytes, myelin/oligodendrocyte. However, no cells were labeled with the neuronal marker beta-tubulin III. FACS analysis showed similar results to those derived via immunocytochemistry, which showed differentiated cells labeled for nestin (88%; FIG. 3C), Sox2 (24%), GFAP (96%; FIG. 3B), MAP2 (29%; FIG. 3D), and myelin/oligodendrocyte (6%; FIG. 3F), but not for β-tubulin III (0%; FIG. 3E). For FACS analysis, cells were fixed with 4% paraformaldehyde for 15 minutes at 4° C., treated with 5% NHS (normal horse serum)/0.1% Triton™-X, and then stained with the following antibodies: rabbit anti-nestin (1:1,000, Chemicon), rabbit anti-Sox2 (1:1,000, Chemicon), rabbit anti-MAP2 (1:1,000, Sigma), mouse anti-β-tubulin III (1:500, Chemicon), rabbit anti-GFAP (1:1000, Chemicon), and mouse anti-myelin/oligodendrocyte (1:1,000, Chemicon). The primary antibodies were detected with FITC-conjugated anti-mouse or anti-rabbit IgG antibody (1:200, Jackson Immuno Research) using $10^4$ cells in a FACSVantage™ fluorescence activated cell sorter (Becton Dickinson). These results indicate that these cancer stem-like cells (CSLCs), unlike normal stem cells, differentiate into aberrant cells that are positive for multiple differentiation markers, notably GFAP and MAP2. Such a dual nature is apparent in the majority of cells differentiated from neurospheres. Furthermore, many cells still remained highly positive for nestin and Sox2. The expression pattern of the differentiated progeny was similar in profile to that of primary cultured tumor cells from which the spheres had originally been isolated and predominantly differentiated into GFAP and MAP2 positive cells that recapitulated the parental tumor phenotype. Additionally, the level of labeling for the NSC markers nestin and Sox2 still remained high, even after 14 days of differentiation. The staining pattern for the monolayer population was similar to neurospheres differentiated for 14 days, except for the expression of Sox2, which was greater in neurospheres differentiated for 14 days. These results reveal that 9L spheres are multipotent for the three neural cell types and differentiate into cells found in the original tumor from which they were obtained.

Example 3

The Aggressiveness of 9L Cells in vivo is Reliant on the Neurosphere Cancer Stem-Like Cells To determine if 9L cells grown as monolayer or neurospheres differ in their ability to grow as a tumor after implantation 5,000 cells from both populations of cells were injected into rats and survival and tumor volume were assayed.

Fisher F344 rats 6-8 weeks old (Harlan Sprague-Dawley, Indianapolis, Ind.) were anesthetized with i.p. ketamine and xylazine, and stereotactically implanted in the right striatum (from bregma in mm: anterior-posterior +1 mm; medial-lateral −3 mm; dorsal-ventral −5 mm) with either isolated 9L sphere cells containing the luciferase gene (5,000 cells) or non-sphere-forming monolayer cells containing the luciferase gene (5,000 cells) in 4 μL of 1.2% methylcellulose/PBS (Rehemtulla et al., Neoplasia, 2:491-495, 2000). Rats were portioned to either the tumor volume group (n=10) or the survival group (n=18), with control rats (n=6) receiving 4 μL of 1.2% methylcellulose/PBS only.

Figure 4A:
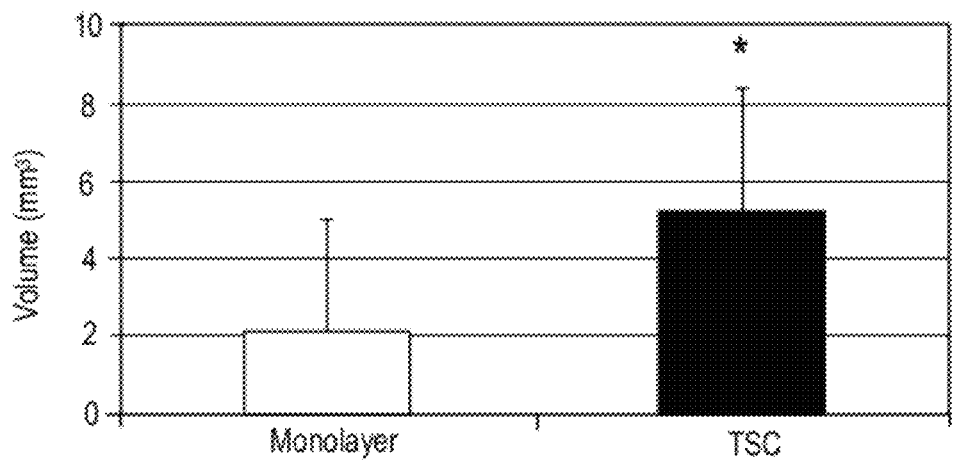
FIG. 4A is a graph depicting volume of tumors induced by neurospheres (n=4) and monolayer cells (n=4) at day 18. Tumors induced by neurospheres were significantly larger ($p<0.02$) than those from the monolayer group.

Because half of each group consisted of either animals implanted with spheres or monolayers, tumor aggression could be determined. Animals in the tumor volume group were sacrificed 18 days after tumor implantation. Tumor volume was assessed by using the formula for an ellipsoid, (length×width×height)/2 (Advani et al., Cancer Res., 59:2055-58, 1999), with the height and the width of the tumor being approximately equal because of the well-defined circumference of the tumors generated by the 9L gliosarcoma (see Sibenaller et al., Neurosurg. Focus, 19:E1, 2005). A significantly (P<0.02) greater tumor volume was observed in the rats implanted with neurosphere cells as compared to rats implanted with monolayer cells (FIG. 4A).

Animals in the survival group were followed for survival and euthanized via $CO_2$ asphyxiation when terminal neurological signs developed (e.g., inability to access food, water, seizure activity, weakness, and paralysis) or if animals exceeded a survival period of 40 days. Following euthanization, brains were harvested and frozen in 2-methylbutane (Sigma), cooled to −20° C., and stored at −80° C. until sectioning. For H&E staining, 20 μm coronal brain sections described above were mounted on slide and stained with Harris hematoxylin for 2 minutes and then counterstained with alcoholic eosin. Reticulin stains were performed on 12 μm coronal brain sections.

Figure 4B:
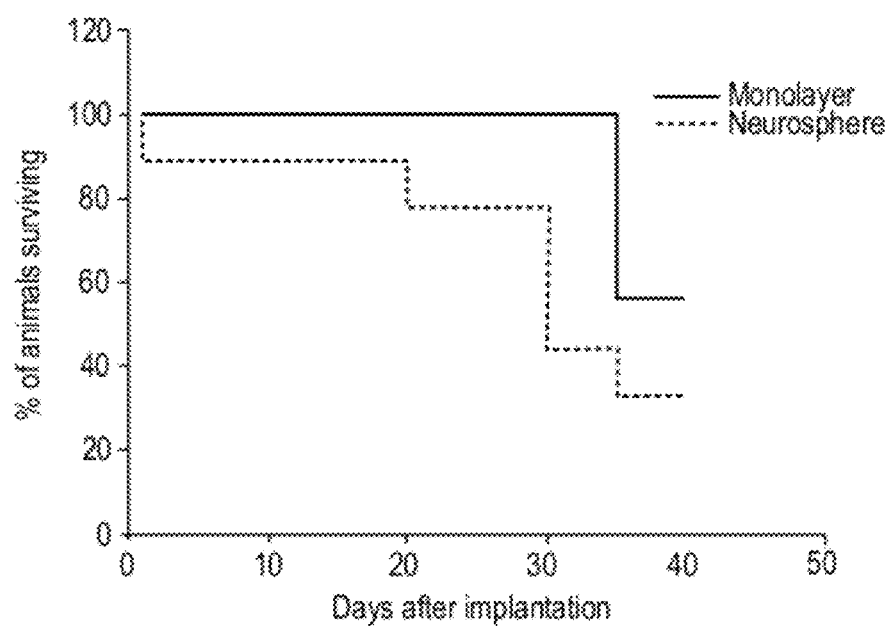
FIG. 4B is a line chart depicting survival of rats with tumors induced by neurospheres (n=9) and monolayer cells (n=9). On average, animals in the neurosphere group died at a significantly ($p<0.02$) earlier time point compared to those in the monolayer group.

Similar to the results seen in the tumor size groups, rats implanted with neurospheres on average had shorter survival times than rats implanted with monolayer cells (FIG. 4B). Six rats in the neurosphere group had large tumors that lead to terminal neurological symptoms, whereas 3 showed evidence of small tumors after 40 days of survival as seen by H&E staining of brain sections. In contrast, only 4 rats had tumors large enough to create terminal neurological symptoms in the monolayer group, whereas 5 showed evidence of small tumor or engraftment after 40 days of survival as determined by H&E staining. Furthermore, the rats in the monolayer group which developed terminal neurological signs of tumor did so at a later time (36 days compared to 29 days in the neurosphere group), which was significant when analyzed using the Kaplan-Meier test (P<0.02).

To determine the establishment of tumor in vivo, 150 mg/kg of the luciferase substrate D-luciferin (Biosynth, International, Inc., Naperville, Ill.) was administered i.p. to animals in the survival group, and luciferase scans were taken 15 minutes later. Luciferase scans generated at 14 days post implantation demonstrated a greater proportion of animals with tumor burden in the neurosphere group compared to the monolayer group, even though a higher expression level of luciferase in vitro was observed in monolayer cells as compared to neurosphere cells.

To determine if the 9L neurospheres could recapitulate the 9L sarcoma in vivo, histological analysis of the tumors was performed. The tumor-cell-implanted rat brains were cut with a cryostat into 20 μm coronal sections and fixed in 4% paraformaldehyde, washed with PBS, and air dried. To characterize the brain tissue by immunohistochemistry, free-floating sections were blocked with 5% NHS (normal horse serum) for 30 minutes at room temperature and then stained with the following antibodies: rabbit anti-nestin (1:200, Chemicon), rabbit anti-Sox2 (1:1,000, Chemicon), rabbit anti-MAP2 (1:1,000, Sigma), mouse anti-β-tubulin III (1:200, Chemicon), rabbit anti-GFAP (1:1000, Chemicon), mouse anti-myelin/oligodendrocyte (1:1000; Chemicon). The primary antibodies were detected as in Example 1. The cells were counterstained with 4',6-diamidino-2-phenylindole (DAPI; Vector Laboratories) to identify all nuclei. The stained sections were examined and photographed using the Zeiss Axiovision 3.1 program in conjunction with Zeiss Axioskop™ 2 microscope, and analyzed using Image J (NIH).

Tumors from the neurosphere cell population were large and well-circumferential, and showed cells positive for the NSC marker nestin, as well as cells positive for the lineage markers GFAP, β-tubulin III, and myelin/oligodendrocytes. Most of the labeling within the tumor volume was directed against GFAP, and a lesser degree of labeling was observed for β-tubulin III, myelin/oligodendrocyte, and nestin. A significant portion (>75%) of the tumor volume stained positive for reticulin, consistent with a sarcomatous component. Additionally, H&E staining revealed a high grade glioma with necrosis consistent with a glioblastoma, displaying the dual nature of the gliosarcoma. Neurospheres formed high grade gliomas with necrosis as seen on H&E (FIG. 5A). The tumors were large and well circumferential as evidenced in non-stained sections (FIG. 5B) and stained for the nuclear marker DAPI (FIG. 5D). A comparison of non-tumor area (FIG. 5D) with tumor area (FIG. 5E) stained for reticulin revealed high levels of reticulin in tumor engulfed regions, showing the histological sarcomatous component of the gliosarcoma. The staining patterns suggest that 9L neurospheres recapitulated the original tumor by differentiating into both neural and glial lineages in vivo.

Example 4

Proliferation Rate and Drug Sensitivity of 9L Neurospheres

To compare the differential proliferation rates and resistance to chemotherapeutic agents, 2,000 healthy 9L sphere and monolayer cells were exposed to either Dulbecco's modified Eagle's medium/F-12 medium containing 10% fetal bovine serum (FBS), or 100 μM stock solution of Temozolamide or Carboplatin dissolved in PBS at concentrations of 1,000 μM, 500 μM, 250 μM, and 125 μM for 2 days. The viability of the cells was scored by measurement of the absorption of formazan dye (the amount of formazan dye formed directly correlates to the number of metabolically active cells) using the cellular proliferation assay WST-1 (Roche Molecular Biochemicals, Mannheim, Germany). Formazan was measured with the use of a microplate reader (Tecan) and spectrophotometer set at a wavelength of 440 nm and a reference wavelength of 890 nm. Cellular viability was determined by exposing cells to WST-1 for 4 hours, and calculating the percentage of viable cells. Proliferation was also assessed by using manual cell counting after 7 days in culture, with an initial cellular concentration of 100,000 cells/mL in a 25 mm² flask.

Figure 6A:
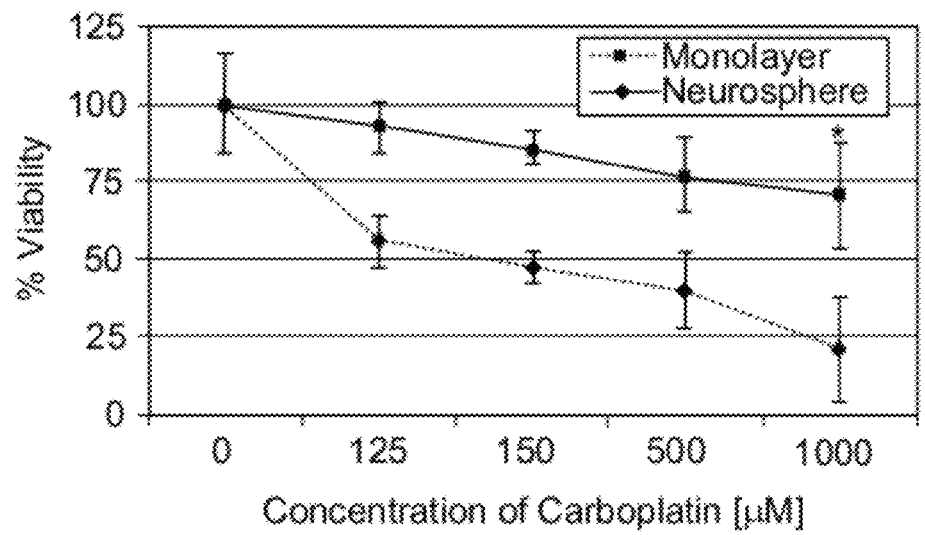
FIGS. 6A-6B are line graphs depicting chemoresistance of neurospheres and monolayer cells to the indicated concentrations of carboplatin (6A) and Temodar (6B). Each value represents the mean of three independent trials. Neurospheres were significantly more resistant ($p<0.05$) to both chemotherapeutic agents as compared to monolayer cells.
Figure 6B:
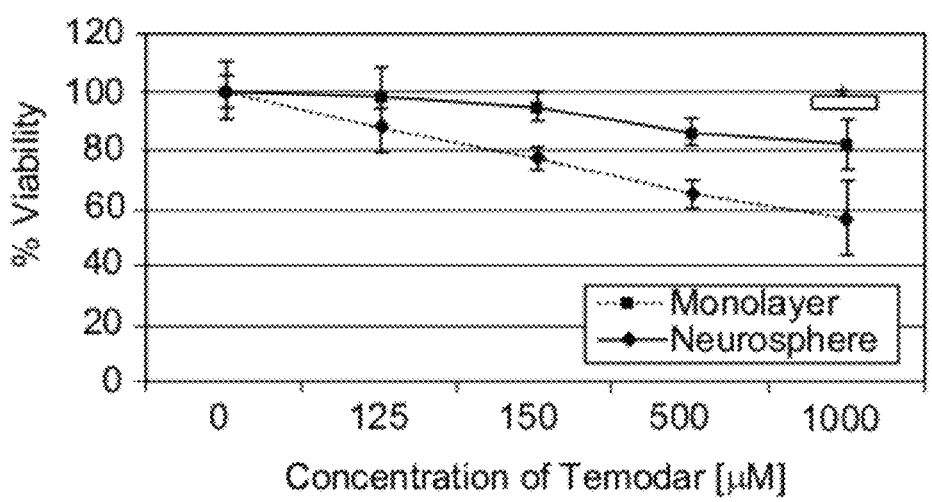
Figure 7:
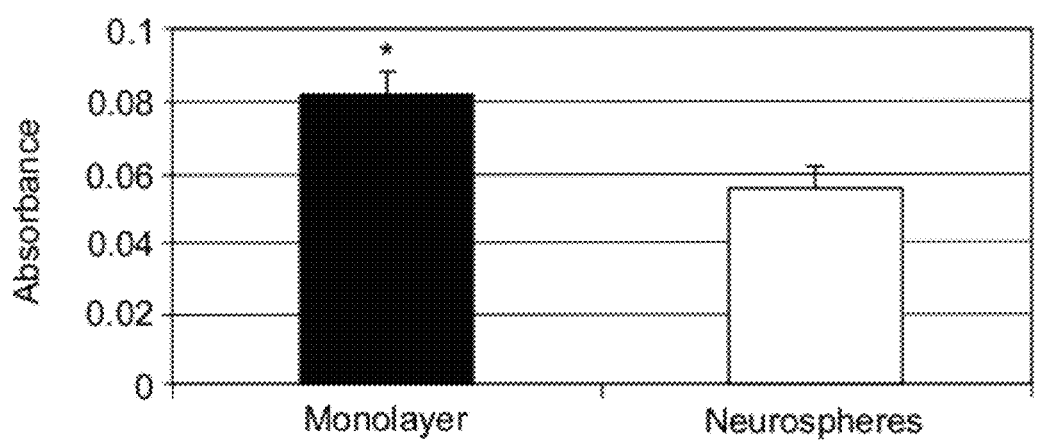
FIG. 7 is a bar graph depicting proliferation rates of neurospheres and monolayer cells in serum-containing media for 2 days. The WST-1 proliferation assay was used to measure absorbance, which directly correlates to the cell number. The monolayer cells proliferated at a significantly ($p>0.05$) greater rate than the neurosphere cells.

The neurospheres demonstrated significantly ($P<0.05$) greater resistance to temozolamide (FIG. 6B) and carboplatin (FIG. 6A) when compared to the 9L cells grown as a monolayer under the same conditions. When the cells were not treated with the chemotherapeutic agents and simply grown in medium, there was a significantly ($P<0.05$) greater increase in cell number in the monolayer group by a factor of 1.48 when using the WST-1 proliferation assay when the cells were not treated with the chemotherapeutic agents. The results of the proliferation assays are depicted in FIG. 7, which is a bar graph that shows a greater increase in cells in the monolayer group. A similar trend in the untreated cells was also observed using the manual cell count method, which showed a greater increase in monolayers by a factor of 1.35. This example demonstrates that neurosphere cells have a greater resistance to chemotherapeutic agents.

Example 5

Isolation of Human CD133-Positive Cancer Stem Cells

Glioblastoma specimens were obtained from patients (with informed consent) via the Brain Tumor Registry and were reviewed and released by a pathologist in the operating room. Independent pathologists classified the tumors by type and grade in accordance with the WHO histological grading of central nervous system tumors. IRB certified technicians processed the glioma tissues under sterile conditions in a laminar flow hood. Tumor cells were cultured in the following complete medium: Ham's F-12/DMEM with high glucose (Irvine scientific, Santa Ana, Calif.), 10 mM HEPES (Invitrogen, Carlsbad, Calif.), 0.1 mg/ml Gentamicin (Invitrogen) and 10% heat-inactivated FBS (Irvine Scientific, Santa Ana, Calif.). The cultured cells were maintained for 3-4 passages. Floating neurosphere-like cells were obtained that were capable of forming new spheres in medium containing FBS for 3-4 passages.

Figure 9A:
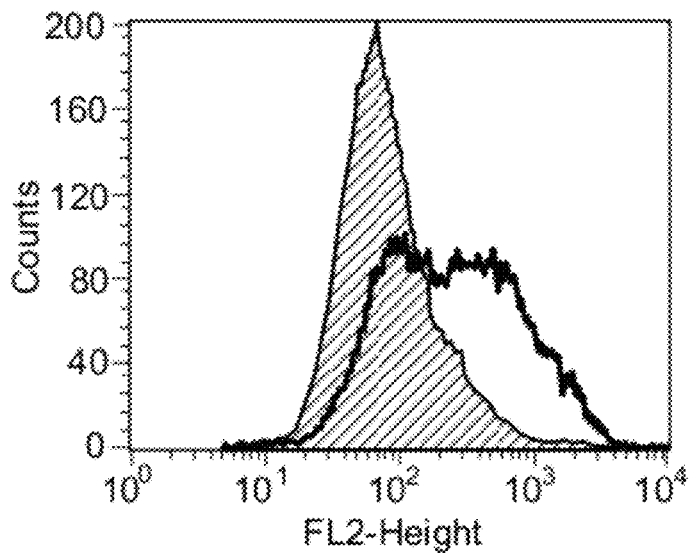
FIGS. 9A-9C are histograms depicting CD133 protein expression on primary cultured tumor cells. Tumor cells were cultured in F-12/DMEM 10% FBS medium for 3-4 passages and stained with specific mAb to CD133 and isotype control-matched mAb. Results are given as the percentage of CD133 positive cells in the total population. In the histograms, the thick lines represent staining with CD133 mAb, and the thin lines represent the isotype control-matched mAb. (9A) tumor cells from patient No. 1049; (9B) tumor cells from patient No. 377; (9C) tumor cells from patient No. 66.
Figure 9B:
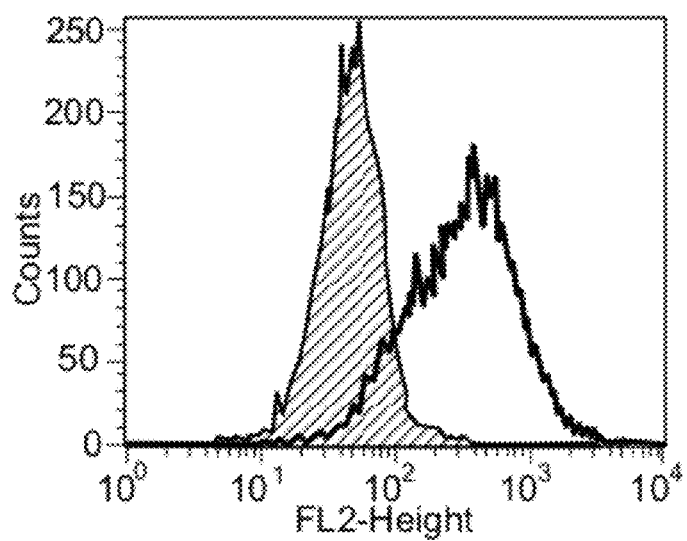
Figure 9C:
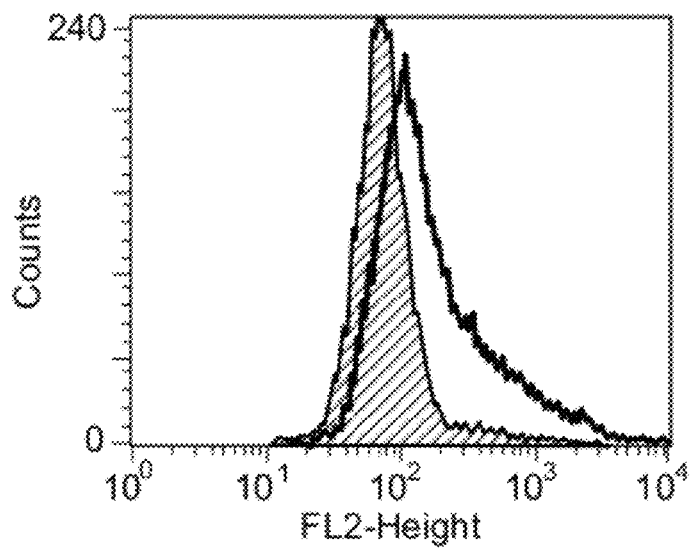

Three adult glioblastoma primary tumor cell lines (Nos. 1049, 377, and 66) were derived by the above method and analyzed by FACS for CD133 expression. Tumor cells were collected and stained with anti-CD133 antibody (mouse monoclonal IgG1; 1:10; Milteny Biotec) or IgG1 isotype control antibody (BD Pharmingen, San Diego, Calif.). After PE-anti-mouse IgG1 (BD Pharmingen) staining for 30 minutes, CD133 staining was analyzed by flow cytometry using a FACSCalibur™ fluorescence activated cell sorter (Becton Dickinson, San Jose, Calif.). CD133 expression was observed in 10.2% (No. 66; FIG. 9C), 27% (No. 1049, FIG. 9A) and 69.7% (No. 377; FIG. 9B) of the total population examined.

Figure 8B:
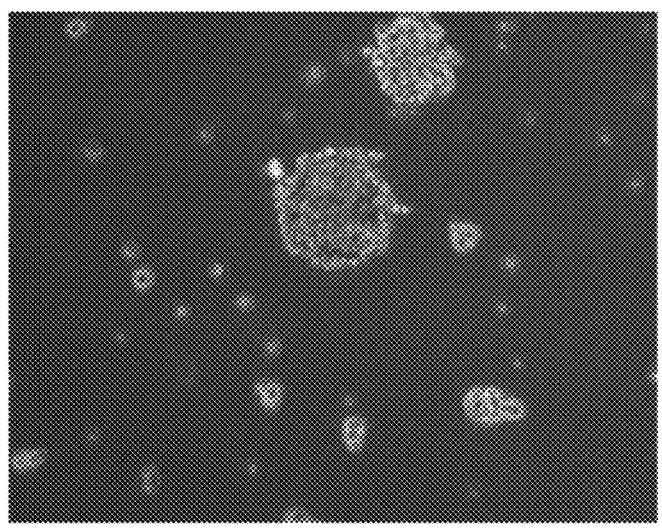
Figure 8C:
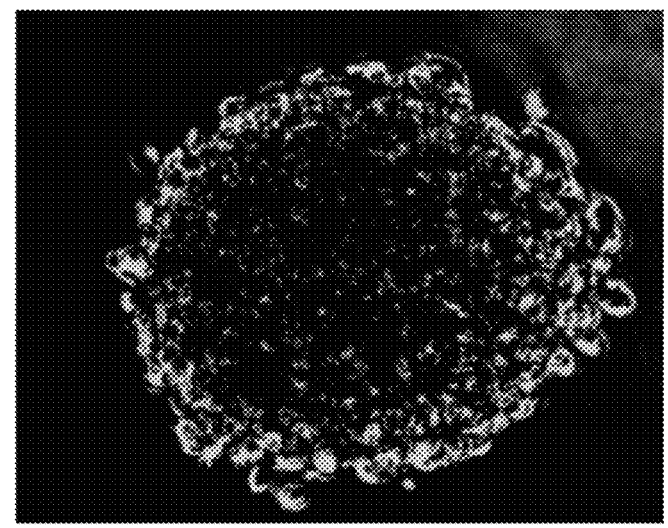

To investigate the capacity of self-renewal and clonogenic potential of $CD133^+$ cell, a single isolated CD133 positive cancer stem cell was isolated by DAKOcytomation™ (DAKO, Carpinteria, Calif.) sorting and cultured in a defined serum-free NSC medium (Kabos et al., Exp. Neurol., 178: 288-293, 2002) containing 20 ng/ml of basic fibroblast growth factor (bFGF, Peprotech, Rocky Hill, N.J.), 20 ng/ml of epidermal growth factor (EGF, Peprotech) and 20 ng/ml leukemia inhibitory factor (LIF, Chemicon, Temecula, Calif.). Single isolated CD133 positive cancer stem cells were able to form neurospheres (FIG. 8A), and were demonstrated to have the capacity for self-renewal and clonogenic potential (FIG. 8B), and sustained expression of CD133 in serum-free medium containing EGF/FGF (FIG. 8C).

Example 6

Human CD133 Positive Tumor Cells Express Markers Associated with Neural Precursors To determine the expression of other genes in CD133 positive cells, CD133 positive cells and CD133 negative cells were obtained by FACS sorting as described in Example 5 and real-time PCR was used to analyze some markers associated with neural precursors in these two populations. Total RNA was extracted from the isolated CD133 positive and CD133 negative cells using an RNA4PCR™ kit (Ambion, Austin, Tex.) according to the manufacturer's protocol. For cDNA synthesis, ~1 μg total RNA was reverse-transcribed into cDNA using Oligo dT primer and iScript™ cDNA synthesis kit reverse transcriptase. cDNA was stored at −20° C. Gene expression was quantified by real-time quantitative RT-PCR using QuantiTect™ SYBR Green dye (Qiagen, Valencia, Calif.). DNA amplification was carried out using Icycler™ (BIO-RAD, Hercules, Calif.), and the detection was performed by measuring the binding of the fluorescence dye SYBR Green I to double-stranded DNA. All the primer sets were obtained from Qiagen (see Table 1).

TABLE 2

Oligonucleotide primers sequences used for SYBR Green real-time PCR

| Gene | Forward | Reverse |
| --- | --- | --- |
| Beta-actin | 5'-TTCTACAATGAGCTGCGTGTG-3' (SEQ ID NO: 1) | 5'-GGGGTGTTGAAGGTCTCAAA-3' (SEQ ID NO: 2) |
| CD133 | 5'-GCATTGGCATCTTCTATGGTT-3' (SEQ ID NO: 3) | 5'-CGCCTTGTCCTTGGTAGTGT-3' (SEQ ID NO: 4) |
| MSI1 | 5'-GAGACTGACGCGCCCCAGCC-3' (SEQ ID NO: 5) | 5'-CGCCTGGTCCATGAAAGTGACG-3' (SEQ ID NO: 6) |
| MELK | 5'-CTTGGATCAGAGGCAGATGTTTGGAG-3' (SEQ ID NO: 7) | 5'-GTTGTAATCTTGCATGATCCAGG-3' (SEQ ID NO: 8) |
| PSP | 5'-GGCGGGGCAGTGCCTTTCAAA-3' (SEQ ID NO: 9) | 5'-TGTTGGCTGCGTCTCATCAAAACC-3' (SEQ ID NO: 10) |
| CD90 | 5'-CGCTCTCCTGCTAACAGTCTT-3' (SEQ ID NO: 11) | 5'-CAGGCTGAACTCGTACTGGA-3' (SEQ ID NO: 12) |
| NESTIN | 5-ATCGCTCAGGTCCTGGAA-3' (SEQ ID NO: 13) | 5'-AAGCTGAGGGAAGTCTTGGA-3' (SEQ ID NO: 14) |
| CD44 | 5'-AGAAGGTGTGGGCAGAAGAA-3' (SEQ ID NO: 15) | 5'-AAATGCACCATTTCCTGAGA-3' (SEQ ID NO: 16) |
| GLI1 | 5'-AGGGAGGAAAGCAGACTGAC-3' (SEQ ID NO: 17) | 5'-CCAGTCATTTCCACACCACT-3' (SEQ ID NO: 18) |
| CXCR4 | 5'-GATCAGCATCGACTCCTTCA-3' (SEQ ID NO: 19) | 5'-GGCTCCAAGGAAAGCATAGA-3' (SEQ ID NO: 20) |
| Bmi-1 | 5'-GGAGACCAGCAAGTATTGTCCTTTTG-3' (SEQ ID NO: 21) | 5'-CATTGCTGCTGGGCATCGTAAG-3' (SEQ ID NO: 22) |
| PTCH1 | 5'-CGCCTATGCCTGTCTAACCATGC-3' (SEQ ID NO: 23) | 5'-AAATGGCAAAACCTGAGTTG-3' (SEQ ID NO: 24) |
| Snail | 5'-ACCACTATGCCGCGCTCTT-3' (SEQ ID NO: 25) | 5'-GGTCGTAGGGCTGCTGGAA-3' (SEQ ID NO: 26) |
| SIRT1 | 5'-ACTTGTACGACGAAGACGAC-3' (SEQ ID NO: 27) | 5'-CAGAAGGTTATCTCGGTACC-3' (SEQ ID NO: 28) |
| Survivin | 5'-TGCCTGGCAGCCCTTTC-3' (SEQ ID NO: 29) | 5'-CCTCCAAGAAGGGCCAGTTC-3' (SEQ ID NO: 30) |
| CIAP1 | 5'-CAGCCTGAGCAGCTTGCAA-3' (SEQ ID NO: 31) | 5'-CAAGCCACCATCACAACAAAA-3' (SEQ ID NO: 32) |
| CIAP2 | 5'-TCCGTCAAGTTCAAGCCAGTT-3' (SEQ ID NO: 33) | 5'-TCTCCTGGGCTGTCTGATGTG-3' (SEQ ID NO: 34) |
| NAIP | 5'-GCTTCACAGCGCATCGAA-3' (SEQ ID NO: 35) | 5'-GCTGGGCGGATGCTTTC-3' (SEQ ID NO: 36) |
| XIAP | 5'-AGTGGTAGTCCTGTTTCAGCATCA-3' (SEQ ID NO: 37) | 5'-CCGCACGGTATCTCCTTCA-3' (SEQ ID NO: 38) |
| BCL-2 | 5'-CATGCTGGGGCCGTACAG-3' (SEQ ID NO: 39) | 5'-GAACCGGCACCTGCACAC-3' (SEQ ID NO: 40) |
| BCL-$X_L$ | 5'-TGCATTGTTCCCATAGAGTTCCA-3' (SEQ ID NO: 41) | 5'-CCTGAATGACCACCTAGAGCCTT-3' (SEQ ID NO: 42) |

TABLE 2-continued

Oligonucleotide primers sequences used for SYBR Green real-time PCR

| Gene | Forward | Reverse |
|------|---------|---------|
| FLIP | 5'-CATCCACAGAATAGACCTGAAGACAA-3' (SEQ ID NO: 43) | 5'-GCTTGGAGAACATTCCTGTAACTTG-3' (SEQ ID NO: 44) |
| BAX | 5'-TGG AGCTGCAGAGGATGATTG-3' (SEQ ID NO: 45) | 5'-GAAGTTGCCGTCAGAAAACATG-3' (SEQ ID NO: 46) |
| BCRP-1 | 5'-TGGCTGTCATGGCTTCAGTA-3' (SEQ ID NO: 47) | 5'-GCCACGTGATTCTTCCACAA-3' (SEQ ID NO: 48) |
| MGMT | 5'-CTGGCTGAATGCCTACTTCC-3' (SEQ ID NO: 49) | 5'-CAACCTTCAGCAGCTTCCAT-3' (SEQ ID NO: 50) |
| OCT4 | 5'-CCTGAAGCAGAAGAGGATCA-3' (SEQ ID NO: 51) | 5'-CCGCAGCTTACACATGTTCT-3' (SEQ ID NO: 52) |

Quantification of target gene mRNA as compared to an internal control (beta-actin) was performed by following a $\Delta C_T$ method. An amplification plot that had been the plot of fluorescence signal vs. cycle number was drawn. The difference ($\Delta C_T$) between the mean values in the duplicated samples of target gene and those of beta-actin were calculated by Microsoft Excel and the relative quantified value (RQV) was expressed as $2^{-\Delta C_T}$. The relative expression of each gene was compared to autologous CD133 negative cells. The results of the QT-PCT analysis are presented in Table 3.

TABLE 3

Relative Expression of Genes in CD133+ Cancer Stem Cells

| | No. 66 | | No. 377 | | No. 1049 | |
|---|---|---|---|---|---|---|
| Gene name | CD133− | CD133+ | CD133− | CD133+ | CD133− | CD133+ |
| CD90 | 1 | 15.6 ± 0.66 | 1 | 12.8 ± 0.94 | 1 | 13.5 ± 0.75 |
| CD44 | 1 | 5.7 ± 0.48 | 1 | 2.5 ± 0.22 | 1 | 2.8 ± 0.19 |
| CXCR4 | 1 | 337.8 ± 29.2 | 1 | 251.5 ± 22.1 | 1 | 264.9 ± 22.9 |
| Nestin | 1 | 21.4 ± 1.25 | 1 | 23.2 ± 1.65 | 1 | 22.1 ± 1.54 |
| MSI | 1 | 84 ± 7.6 | 1 | 75.4 ± 7.03 | 1 | 53.5 ± 6.2 |
| MELK | 1 | 1351 ± 95.8 | 1 | 467.7 ± 40.5 | 1 | 514.6 ± 45.6 |
| GLI-1 | 1 | 46 ± 3.8 | 1 | 43 ± 4.5 | 1 | 49 ± 5.9 |
| PTCH | 1 | 16 ± 1.48 | 1 | 13.5 ± 0.85 | 1 | 14.3 ± 1.24 |
| MGMT | 1 | 32.4 ± 2.5 | 1 | 34.7 ± 2.9 | 1 | 56.3 ± 4.2 |
| BCRP1 | 1 | 6.5 ± 0.43 | 1 | 4.3 ± 0.25 | 1 | 4.8 ± 0.24 |
| SIRT1 | 1 | 4.9 ± 0.34 | 1 | 4.2 ± 0.26 | 1 | 5.4 ± 0.29 |
| FLIP | 1 | 294 ± 25.5 | 1 | 157.6 ± 14.2 | 1 | 145.6 ± 13.7 |
| BCL-2 | 1 | 13.9 ± 0.95 | 1 | 4.9 ± 0.54 | 1 | 3.8 ± 0.54 |
| BCL-XL | 1 | 5.6 ± 0.39 | 1 | 3.2 ± 0.16 | 1 | 2.5 ± 0.14 |
| cIAP1 | 1 | 39.0 ± 3.5 | 1 | 4.3 ± 0.53 | 1 | 5.6 ± 0.65 |
| cIAP2 | 1 | 3 ± 0.25 | 1 | 1.9 ± 0.12 | 1 | 1.7 ± 0.14 |
| XIAP | 1 | 21.9 ± 2.2 | 1 | 9.7 ± 0.68 | 1 | 10.3 ± 0.91 |
| NAIP | 1 | 12.1 ± 0.75 | 1 | 6.4 ± 0.43 | 1 | 4.5 ± 0.62 |
| Survivin | 1 | 1.6 ± 0.08 | 1 | 2.3 ± 0.18 | 1 | 2.4 ± 0.18 |
| BAX | 1 | 0.33 ± 0.03 | 1 | 0.49 ± 0.06 | 1 | 0.21 ± 0.05 |

CD90, CD44, CXCR4, Nestin, Musashi-1 (Msi1), and maternal embryonic leucine zipper kinase (MELK) mRNA expression on CD133 positive cancer stem cells was upregulated by an average of 15.6, 5.7, 337.8, 2.14, 84, and 1351 fold, respectively, compared to the levels found on autologous CD133 negative tumor cells. mRNA levels for GLI1 and PTCH1 were upregulated an average of 46 and 16 times, respectively, in CD133 positive cells, as compared to CD133 negative cells. Furthermore, Bmi-1, phosphoserine phosphatase (PSP), SHH, OCT4 and Snail mRNA were expressed in CD133 positive cells derived from the three cell lines; none of the five genes were detectable on CD133 negative cells. Additionally, anti-apoptotic genes were also upregulated (see Example 8).

Example 7

CD133 Positive Cancer Stem Cells are Resistant to Chemotherapeutic Agents

To determine whether CD133 positive cancer stem cells were resistant to chemotherapeutic agents, the WST-1 Cell Proliferation Assay was used to examine the drug sensitivity of CD133 positive cells and CD133 negative cells (both collected by FACS sorting from the three glioblastoma patients' primary cultured tumor cells as described above). CD133 positive and negative cells were exposed to conventional chemotherapeutic agents, temozolomide, carboplatin, VP-16 or taxol at various concentrations, for up to 48 hours in 10% FBS/F-12/DMEM culture medium. Temozolomide was supplied by the Schering-Plough Research Institute (Kenilworth, N.J.) and was dissolved in DMSO (Sigma Chemical Co., St Louis, Mo.) at 100 mM stock solution. Carboplatin, etoposide (VP-16) and paclitaxel (Taxol) were obtained from Sigma-Aldrich (St. Louis, Mo.). CD133 positive cells isolated from No. 66 showed dramatic drug resistance to the above four agents including temozolomide (FIG. 10C), carboplatin (FIG. 10D), VP-16 (FIG. 10A), and Taxol (FIG. 10B) as compared to autologous CD133 negative cells. CD133 positive cells isolated from No. 377 showed significant resistance to carboplatin at all concentrations tested (FIG. 11A) and to VP-16 at 200 µM (FIG. 11B). CD133 positive cells isolated from No. 1049 showed significant resistance to carboplatin at 200 µM compared to autologous CD133 negative cells (FIG. 11C). This example demonstrates increased drug resistance of CD133 positive cancer stem cells as compared to autologous CD133 negative cells.

Example 8

Anti-Apoptotic Genes are Upregulated in CD133 Positive Cancer Stem Cells

Real-time PCR of FACs-sorted CD133 positive and CD133 negative cells was used to investigate the relative expression of multi-drug resistance genes and genes related to inhibiting cell apoptosis between these two populations. BCRP1 has been demonstrated to play an important role in the drug resistance of normal stem cells and tumor stem cells (Zhou et al., Nat. Med., 7:1028-34, 2001; Hirschmann-Jax et al., Proc. Natl. Acad. Sci. USA, 101:14228-33, 2004). Higher expression of BCRP1 (6.5 fold) was found in CD133 positive cells as compared to that of autologous CD133 negative cells. Furthermore, anti-apoptotic genes, such as FLIP, BCL-2, and BCL-XL, were found at significantly higher levels (294, 13.9 and 5.6 times higher) in CD133 positive cells than in CD133 negative cells. Also, inhibitor of apoptosis protein (IAPs) family members, XIAP, cIAP1, cIAP2, NAIP, and survivin were found at higher expression levels on CD133 positive cells 21.9, 39.04, 3.03, 12.1, 6.73, and 1.6 times higher, respectively, than in CD133 negative cells. It has been demonstrated that SIRT1 deacetylates the DNA repair factor Ku70, causing it to sequester the pro-apoptotic factor, Bax, away from mitochondria, thereby inhibiting stress-induced apoptotic cell death (Cohen et al., Science, 305:390-392, 2004). SIRT1 deacetylase mRNA expression was increased 4.92 times in CD133 positive cells. The pro-apoptotic gene BAX was decreased 3 times in CD133 positive cells as compared to autologous CD133 negative cells. Thus, gene expression differences were observed in CD133 positive cells as compared to CD133 negative cells.

Example 9

Recurrent Glioblastomas Express Higher Levels of CD133

Figure 12:
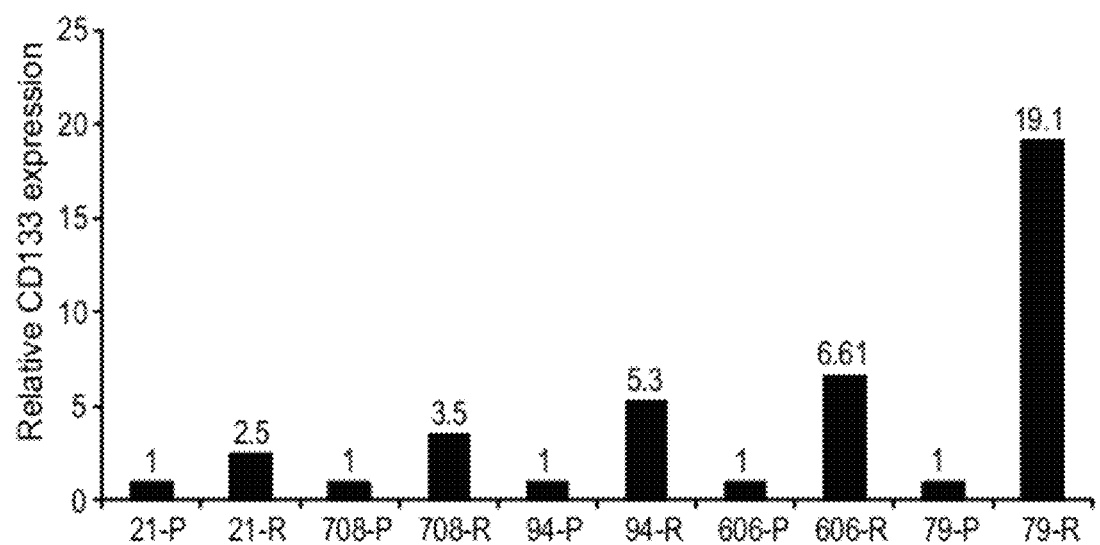
FIG. 12 is a bar graph depicting CD133 mRNA expression in primary (P) and recurrent (R) tumor tissue. Total RNA was extracted from both primary and recurrent tumor tissue derived from five patients, and CD133 mRNA expression was measured by real-time qPCR. The relative CD133 mRNA level of recurrent tumor was presented as the fold increase compared to that of autologous primary tumor tissue. Data are representative of two independent experiments.

Malignant glioma is a highly recurrent tumor even after surgery, chemotherapy, radiation and immunotherapy. To address the potential role of CD133 positive tumor cells in glioblastoma recurrence, the CD133 expression upon first and second resection of tumor tissue from the same patient were compared. We obtained primary tumor tissue from five pathological confirmed grade IV astrocytoma (GBM) patients, and then re-operated following radiation, chemotherapy, and/or immunotherapy to obtain recurrent tumor tissue. RNA extraction and RT-PCR was performed for CD133 as described above. For all tested patients, CD133 expression was significantly higher in recurrent tumor tissue (relative expression ~2.5-19.1) than that in autologous primary tumor tissue (relative expression ~1)(FIG. 12). This example implicates a resistant CD133 positive tumor population in tumor recurrence.

Example 10

Immunization with Cancer Stem Cell Antigens Increased Survival

A dendritic cell vaccine was generated using antigens from neurospheres, daughter cells, and monolayer cells. Immature dendritic cells were generated from the bone marrow of 6-12-week-old Fisher F344 rats as previously described (Talmor et al., Eur. J. Immunol., 28:811-817, 1998). Briefly, bone marrow was harvested from the femoral and tibial marrow cavities and cultured in RPMI 1640 media supplemented with 10% fetal bovine serum (Gemini Biotechnologies, Calabasas, Calif.), 1% Penicillin/Streptomycin (Invitrogen, Carlsbad, Calif.), 50 ng/ml recombinant rat GM-CSF and 100 ng/ml recombinant rat IL-4 (R & D Systems, Minneapolis, Minn.). Cultures were fed every 2 days by removing 75% of the media and replacing it with fresh media containing cytokines (this washed away most of the lymphocytes and granulocytes). To determine the percentage of immature dendritic cells generated and cultured from the bone marrow of Fisher rats after 1 week of exposure to GM-CSF and IL-4, FACS analysis was run on cells immunostained with antibodies for CD86 (co-stimulatory marker B7-1; DC marker), CD80 (costimulatory marker B7-2; DC marker), CD3 (T cell marker), or MHC II (DC marker). The dendritic cell populations obtained were positive for CD86, CD80, and MHC II, while negative for CD3.

Soluble peptides were generated for dendritic cell pulsing by cell lysis. 9L neurospheres, daughter cells, and monolayer (adherent) cells were processed in the laboratory to produce a single cell suspension. The cells were then lysed by 4 to 5 freeze cycles (on liquid nitrogen) and thaw cycles (room temperature). Lysis was monitored by light microscopy, and larger particles were removed by centrifugation (10 minutes at 600×g). The supernatants were passed through a 0.2 µm filter, and protein concentration was determined by BioRad protein assay and aliquots frozen at −80° C. until use.

To establish intracranial tumors, adult Fisher F344 rats were stereotactically inoculated in the right corpus striatum (from bregma in mm: anterior-posterior +1 mm; medial-lateral −3 mm; dorsal-ventral −5 mm) with 25,000 9L-luciferase tumor cells as described above. For vaccination of the rats, freshly cultured immature dendritic cells were cocultured overnight for 24 hours with 80-100 µg of cell lysate one day prior to the vaccination at days 7, 14, and 21 post-operatively. Vaccinations were given subcutaneously in the flanks on days 7, 14, and 21 with 50,000 DCs pulsed with antigens from either 9L neurospheres (NS), daughter cells (DtC), monolayer (adherent) cells (AC), or saline control. The animals were followed for survival and euthanized when terminal neurological signs developed, for example, inability to access food, water, seizure activity, weakness, and paralysis.

Figure 13:
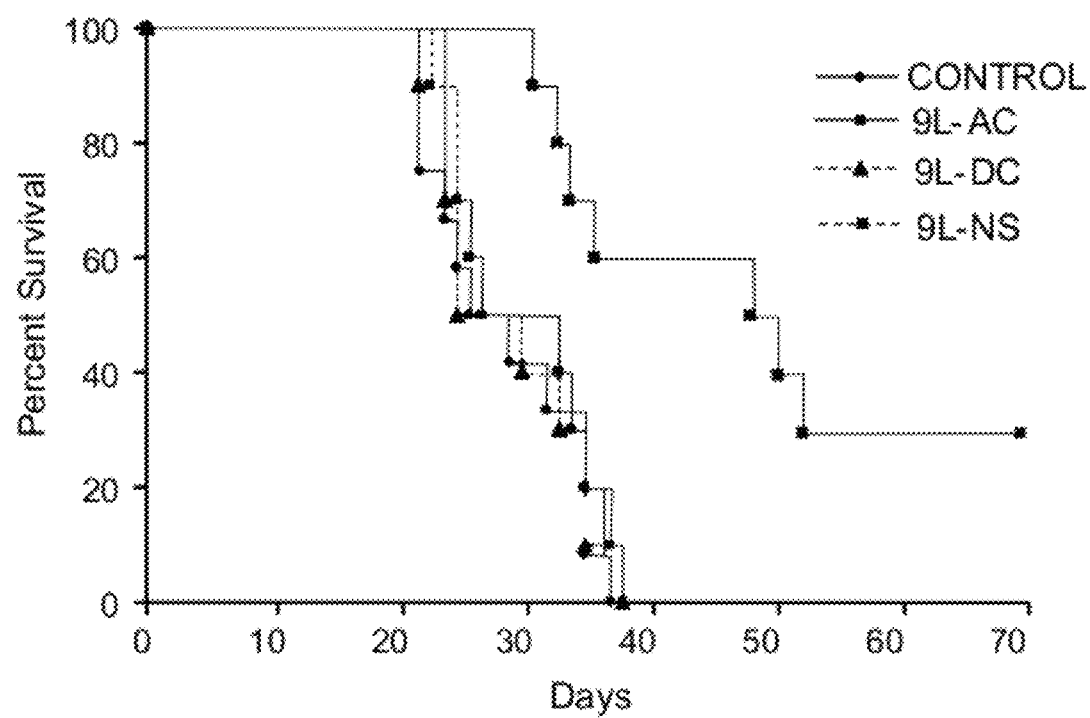
FIG. 13 is a line graph depicting survival of 9L tumor-bearing rats vaccinated with dendritic cells pulsed with antigens from 9L adherent cells (9L-AC), 9L daughter cells (9L-

Tumor bearing rats injected with three successive vaccines (once per week) of dendritic cells pulsed with control, AC, DtC, or NS antigens, had median survival dates of 26.5, 32, 29 and 50 days, respectively (FIG. 13). Kaplan-Meier analysis showed that rats treated with 9L neurosphere lysate-pulsed DC had significantly longer survival time than each of the other groups (p=0.0015).

Example 11

DCs Pulsed with Cancer Stem Cell Antigens Induced a Strong Cytotoxic T Cell Response Against 9L Tumor Cells To determine whether the relative protective effect of NS-DC vaccination on survival is due to tumor-specific immunity, a cytotoxic T lymphocyte (CTL) assay was performed. Spleens were removed on day 28 post-intracranial 9L-luciferase tumor cells implantation from groups of rats treated with either control or 9L peptide-pulsed dendritic cells. Splenocytes were isolated and re-stimulated in vitro, as described (Wunderlich et al., "Assays for T-cell function," In: Coligan et al., eds., *Current Protocols in Immunology*, New York, N.Y., John Wiley & Sons, Inc; 1997:3.11.1-3.11.20; Ehtesham et al., J. Immunother., 26:107-116, 2003) with either irradiated (10,000 rads) 9L adherent cells (AC), daughter cells (DtC) or neurospheres (NS). The effector: target (E:T) ratio was 6:1. Re-stimulated cells were cultured in RPMI-1640 with 10% fetal bovine serum, 1% penicillin-streptomycin, and 1% HEPES in 6-well flat-bottom plates in a humidified 37° C., 5% $CO_2$ incubator. Cells were incubated for 11 days with addition of IL-2 (300 units/mL) every 3 days. After 11 days of re-stimulation, the cells were re-exposed to their initial target (i.e., irradiated 9L AC, DtC, or NS). 24 hours later, culture media was harvested from the remaining cells and used for IFNγ protein quantification by ELISA (Ehtesham et al., J. Immunother., 26:107-116, 2003). Re-stimulated splenocytes from rats treated with NS pulsed DCs showed significantly higher IFNγ release in response to exposure to tumor cell targets than re-stimulated splenocytes from rats treated with AC or DtC (FIG. 14), indicating that a higher cytotoxic T cell response was obtained in the NS-DC vaccinated rats. These data were also confirmed by PCR for IFNγ levels (data not shown). The higher IFNγ response in the NS-DC vaccinated group corresponds to the higher survival rate observed in the same group. These data show that a cancer stem cell antigen vaccine targets tumor cells more potently than vaccines based on tumor antigens from daughter cells, or cell populations that are not enriched for cancer stem cells.

Example 12

Intracranial T-Cell Infiltration is Associated with Prolonged Survival

A representative number of brains from DC-DtC and DC-NS vaccinated rats were carefully removed and post-fixed in 4% paraformaldehyde. Coronal sections of 20 μm were cut on a cryostat and blocked with normal horse serum for 1 hour. Slides were then incubated with anti-CD4 (clone OX-38 monoclonal antibody diluted in 1:200 in PBS) for 2 hours at room temperature, followed by a 20 minute incubation at room temperature with the linking antibody (BioGenex biotinylated anti-mouse immunoglobulin). After washing in PBS, the labeled moiety (BioGenex Horse Radish Peroxidase-conjugated streptavidin) was added for 20 minutes at room temperature. DAB (3,3'-diaminobenzidine) was used as the chromogen. For analysis of CD8 expression, slides were incubated overnight with Anti-CD8 alpha Chain, clone OX-8 antibody (Chemicon).

Immunohistochemical assessment of brain sections from rats vaccinated with dendritic cells pulsed with NS vaccinated showed that there was a robust infiltration of $CD4^+$ (FIG. 15B) and $CD8^+$ lymphocytes that was not observed in the brain sections obtained from rats vaccinated with dendritic cells pulsed with daughter cell antigens (FIG. 15A). This infiltration of T cells correlates with increased survival of rats vaccinated with NS pulsed DCs.

Example 13

Cancer Stem Cells Express MHC, Unlike Normal Stem Cells

Five glioblastoma multiforme (GBM) cancer stem cells (CSC) were generated by the methods described in Yuan et al. (Oncogene, 23:9392-9400, 2004). Briefly, tumor specimens were obtained within half an hour of surgical resection from five adult GBM patients, as approved by the Institutional Review Boards at the Cedars-Sinai Medical Center. Tumor tissue was washed, minced, and enzymatically dissociated (Reynolds et al., Science, 255:1707-10, 1992). Tumor cells were resuspended in DMEM/F12 medium containing 10% fetal bovine serum (FBS) as growth medium and plated at a density of $2\times10^6$ live cells per 75 $cm^2$ flask. The cells attached and grew as a monolayer in flasks. All the five monolayer growing adult GBM cells were switched into a defined serum-free NSC medium (Reynolds et al., Science, 255:1707-10, 1992) containing 20 ng/ml of basic fibroblast growth factor (bFGF, Peprotech, Rocky Hill, N.J.) and 20 ng/ml of epidermal growth factor (EGF, Peprotech). Normal human fetal neural stem cells (NSC) were cultured in the same defined serum-free medium as for cancer stem cells. CSC and NSC cells were stained by FITC-HLA-A,B,C antibody and isotype control antibody (BD Bioscience, San Diego, Calif.) and analyzed by flow cytometry. Representative CSC and NSC results were shown in the FIGS. 17A-17B and 18A-18B, respectively.

HLA expression was seen in 5 of 5 cancer stem cells from different patients. CSCs expressed high levels of HLA-A,B, C, however, NSC did not expression MHC class I (HLA-A, B,C) antigens on the surface. This unexpected result indicates that specific cancer stem cell antigens on cancer stem cells can be targeted using vaccines that generate T cells that recognize and kill cancer stem cell antigens in the context of MHC. Therefore cancer stem cells will be targeted, whereas normal stem cells will not.

Example 14

Isolation of CD133 T Cell Epitopes

A nucleic acid encoding a portion of CD133 extracellular domain 1 (amino acid residues 116-270 of SEQ ID NO:53) is used in cloning and expression on the surface of DC. DC are transfected with CD133-1 cDNA construct or empty vector (mock) for 48 hours. The successful transfection of DC-CD133 cells is identified either by anti-CD133 monoclonal antibody using flow cytometry or by EGFP cloned vector under fluorescent microscopy.

Antigen presenting cells with CD133 receptor are stimulated by CD133 T cell epitopes. Overlapping peptides of 8-10 amino acids of residues 325-350 of SEQ ID NO:53 are produced as MHC class I epitopes. Similarly, overlapping peptides of 13-20 amino acid of residues 325-350 are produced as MHC class II epitopes. Stimulated APC using the peptide epitopes lead to enhanced production of CD8 T cells targeted to CD133 molecular on stem/progenitor cells in brain tumors.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a glioma in a patient, the method comprising:
   obtaining a population of dendritic cells;
   contacting the dendritic cells with one or more isolated peptides of CD133 under conditions such that the dendritic cells present the one or more isolated peptides of CD133, wherein the one or more isolated peptides of CD133 are peptides of 8 to 10 contiguous amino acid residues of amino acid residues 325-350 of SEQ ID NO: 53; and
   administering to the patient a composition comprising the dendritic cells.

2. The method of claim 1, wherein the dendritic cells are autologous.

3. The method of claim 1, wherein the dendritic cells are allogeneic.

4. The method of claim 1, wherein the one or more isolated peptides of CD133 are synthetic.

5. The method of claim 1, wherein the patient is human.

6. The method of claim 5, wherein the patient's tumor is resistant to treatment with a chemotherapeutic agent.

7. The method of claim 5, wherein the patient's tumor has recurred following resection.

8. The method of claim 5, wherein the patient is concurrently receiving, or has received, at least one of chemotherapy, radiation therapy, and surgical therapy.

9. The method of claim 1, further comprising measuring the cytotoxic T cell response to the glioma tumor cells after the administration of the dendritic cells.

10. A method of treating a glioma in a patient, the method comprising:
    administering to the patient a composition of dendritic cells that present CD133 peptides, wherein the CD133 peptides are peptides of 8 to 10 contiguous amino acid residues of amino acid residues 325-350of SEQ ID NO:53.

11. The method of claim 10, wherein the patient is human.

12. The method of claim 11, wherein the patient's tumor is resistant to treatment with a chemotherapeutic agent.

13. The method of claim 11, wherein the patient's tumor has recurred following resection.

14. The method of claim 11, wherein the patient is concurrently receiving, or has received, at least one of chemotherapy, radiation therapy, and surgical therapy.

15. The method of claim 10, wherein the dendritic cells are allogeneic.

16. A method of treating a glioma in a patient, the method comprising:
    obtaining a population of dendritic cells;
    contacting the dendritic cells with one or more isolated peptides of CD133 under conditions such that the dendritic cells present the one or more isolated peptides of CD133, wherein the one or more isolated peptides of CD133 are peptides of 13 to 20 contiguous amino acid residues of amino acid residues 325-350 of SEQ ID NO:53; and
    administering to the patient a composition comprising the dendritic cells.

17. The method of claim 16, wherein the dendritic cells are autologous.

18. The method of claim 16, wherein the one or more isolated peptides of CD133 are synthetic.

19. The method of claim 16, wherein the patient is human.

20. The method of claim 19, wherein the patient's tumor is resistant to treatment with a chemotherapeutic agent.

21. The method of claim 19, wherein the patient's tumor has recurred following resection.

22. The method of claim 19, wherein the patient is concurrently receiving, or has received, at least one of chemotherapy, radiation therapy, and surgical therapy.

23. The method of claim 16, further comprising measuring the cytotoxic T cell response to the glioma tumor cells after the administration of the dendritic cells.

24. The method of claim 16, wherein the dendritic cells are allogeneic.

25. A method of treating a glioma in a patient, the method comprising:
    administering to the patient a composition of dendritic cells that present CD133 peptides, wherein the CD133 peptides are peptides of 13 to 20 contiguous amino acid residues of amino acid residues 325-350 of SEQ ID NO:53.

26. The method of claim 25, wherein the patient is human.

27. The method of claim 26, wherein the patient's tumor is resistant to treatment with a chemotherapeutic agent.

28. The method of claim 26, wherein the patient's tumor has recurred following resection.

29. The method of claim 26, wherein the patient is concurrently receiving, or has received, at least one of chemotherapy, radiation therapy, and surgical therapy.

30. The method of claim 25, wherein the dendritic cells are allogeneic.

* * * * *

UNITED STATES PATENT AND TRADEMARK OFFICE
CERTIFICATE OF CORRECTION

PATENT NO.        : 9,023,338 B2                                Page 1 of 1
APPLICATION NO.   : 13/365666
DATED             : May 5, 2015
INVENTOR(S)       : Yu It is certified that error appears in the above-identified patent and that said Letters Patent is hereby corrected as shown below:

In the claims

Col. 131, Line 54, claim 10, delete "325-350of" and insert -- 325-350 of --.

Signed and Sealed this
Fifteenth Day of September, 2015

Michelle K. Lee
*Director of the United States Patent and Trademark Office*